United States Patent [19]

Barker et al.

[11] Patent Number: 5,428,147

[45] Date of Patent: *Jun. 27, 1995

[54] OCTOPINE T-DNA PROMOTERS

[75] Inventors: Richard F. Barker; John D. Kemp, both of Madison, Wis.

[73] Assignee: Mycogen Plant Science, Inc., San Diego, Calif.

[*] Notice: The portion of the term of this patent subsequent to Apr. 7, 2009 has been disclaimed.

[21] Appl. No.: 91,538

[22] Filed: Jul. 13, 1993

Related U.S. Application Data

[63] Continuation of Ser. No. 869,216, Apr. 13, 1992, abandoned, which is a continuation of Ser. No. 440,432, Nov. 21, 1989, abandoned, which is a continuation of Ser. No. 553,786, Nov. 19, 1983, abandoned, said Ser. No. 741,034, is a continuation-in-part, Aug. 6, 1991, abandoned, which is a continuation of Ser. No. 144,775, Jan. 20, 1988, Pat. No. 5,102,796, which is a continuation of Ser. No. 485,614, Apr. 15, 1983, abandoned, said Ser. No. 713,624, is a continuation-in-part, Jun. 10, 1991, which is a continuation of Ser. No. 260,574, Oct. 21, 1988, abandoned, which is a continuation-in-part of Ser. No. 848,733, Apr. 1986, abandoned, which is a continuation-in-part of Ser. No. 535,354, Sep. 26, 1983, abandoned.

[51] Int. Cl.$^6$ .................. C07H 21/04; C12N 5/00; C12N 15/00; C12P 21/04
[52] U.S. Cl. ............... 536/24.1; 435/69.1; 435/70.1; 435/172.3; 435/240.4; 435/252.3; 435/320.1
[58] Field of Search ............. 435/69.1, 70.1, 172.3, 435/240.4, 252.3, 320.1; 536/24.1

[56] References Cited

U.S. PATENT DOCUMENTS 5,102,796  4/1992  Hall et al. ............ 435/172.3

OTHER PUBLICATIONS

Murai et al. 1983. Science 222: 476–482.
Goodman et al. 1987. Science 236: 48–54.
Herrera–Estrella et al. 1983. Nature 303: 209–213.
DeGreve et al. 1982. J. Mol. Appl. Gen. 1: 499–511.
Herrera–Estrella et al. 1983. EMBO J 2(6): 987–995.
Lippincott et al. 1978. Science 199: 1075–1078.
Krens et al. 1982. Nature 296: 72–74.
Hernalsteens et al. 1984. EMBO J 3(13): 3039–3041.

Primary Examiner—David T. Fox
Attorney, Agent, or Firm—Saliwanchik & Saliwanchik

[57] ABSTRACT

The sequence of the T-DNA of the octopine-type Ti plasmid found in Agrobacterium tumefaciens ATCC 15955 is disclosed. Fourteen open reading frames bounded by eukaryotic promoters, ribosome binding sites, and polyadenylation sites were found. The use of promoters and polyadenylation sites from pTi15955 to control expression of foreign structural genes is taught, using as examples the structural genes for the Phaseolus vulgaris storage protein phaseolin, P. vulgaris lectin, thaumatin, and Bacillus thuringiensis crystal protein. Vectors useful for manipulation of sequences of the structural genes and T-DNA are also provided.

21 Claims, 22 Drawing Sheets

FIG. 1A

```
   1 GGATCCTGATTTACGACAAGGCCACTCAGGTCGATCATGTTATGAGGACA 50
  51 GAGGTAGCGGACTCCCATCAAGGCCACGAGCGTGATCGCTCCAGCGATAG 100
 101 GCCGGATAGATTCACACATCCAATGCCGAGTTGCCGCCAAATGTTCTTCT 150
 151 CGCCCGGGAGGCGTTTATAGATTATCGTAATGCCACGACTAGGCACGCCG 200
 201 CCGAAGACACGGAAGCCGTGCCAGTGCGCGTCAAAGAGCATCTCGTGTGT 250
 251 TTGCAACAAGTAGGCCCTGACCAGAGAAGCCCGACTGTGAGATAGTTTGA 300
 301 TATGTGCGACCTGGAGCTTCGTGCGATCGCCGCCGATCACGGCGTAGTCC 350
 351 TCACTCCAATCGAACTGGAATGCCTCACCAGGCCGGAAAGACAGCGGAAC 400
 401 AAATACGCCACGGCCGGTCGTCTGCTGCTCACGTAGCCGATCAGCTCGCC 450
 451 ACGCGCGGGCGAAGGCGGCCACCCGATCATACGAGCCAGTAAAACCGAGA 500
 501 GCCATCAGGCCGGCATGAAGGTGCTTCAAGGTCCGGCGCTGCTTGCGCGA 550
 551 CTTTCCGGTCTTTGTCTTCAGCCAAGCCGCCAGTTTGTTGGAAAAGGGAT 600
 601 CAAGCTTGCTTGGTCGTTCCGGTACCGTGAACGTCGGCTCGATTGTACCT 650
 651 GCGTTCAAATACTTTGCGATCGTGTTGCGCGCCTGCCCGGTGCGTCGGCT 700
 701 GATCTCACGGATCGACTGCTTCTCTCGCAACGCCATCCGACGGATGATGT 750
 751 TTAAAAGTCCCATGTGGATCACTCCGTTGCCCCGTCGCTCACCGTGTTGG 800
 801 GGGGAAGGTGCACATGGCTCAGTTCTCAATGGAAATTATCTGCCTAACCG 850
 851 GCTCAGTTCTGCGTAGAAACCAACATGCAAGCTCCACCGGGTGCAAAGCG 900
 901 GCAGCGGCGGCAGGATATATTCAATTGTAAATGGCTTCATGTCCGGGAAA 950
 951 TCTACATGGATCAGCAATGAGTATGATGGTCAATATGGAGAAAAAGAAAG 1000
1001 AGTAATTACCAATTTTTTTTCAATTCAAAAATGTAGATGTCCGCAGCGTT 1050
1051 ATTATAAAATGAAAGTACATTTTGATAAAACGACAAATTACGATCCGTCG 1100
1101 TATTTATAGGCGAAAGCAATAAACAAATTATTCTAATTCGGAAATCTTTA 1150
1151 TTTCGACGTGTCTACATTCACGTCCAAATGGGGGCTTAGATGAGAAACTT 1200
1201 CACGATCGATGCCTTGATTTCGCCATTCCCAGATACCCATTTCATCTTCA 1250
1251 GATTGGTCTGAGATTATGCGAAAATATACACTCATATACATAAATACTGA 1300
```

FIG. 1B

```
1301 CAGTTTGAGCTACCAATTCAGTGTAGCCCATTACCTCACATAATTCACTC 1350
1351 AAATGCTAGGCAGTCTGTCAACTCGGCGTCAATTTGTCGGCCACTATACG 1400
1401 ATAGTTGCGCAAATTTTCAAAGTCCTGGCCTAACATCACACCTCTGTCGG 1450
1451 CGGCGGGTCCCATTTGTGATAAATCCACCATCACAATAGATAGTCTAATG 1500
1501 GACGAAAAAGGCGAATATTTCGATGCTGAGATTCGACGCAATTAATTCGA 1550
1551 GAAAAATCCCGTGATTGATGCTGTTGAGTTACCAATAATATGGGCAGCGA 1600
1601 AGGCCATTTAATTATAAGATCTAACAGAGTTTATATTCAAAAATCAGTCA 1650
1651 CTAATTCGATATGTATGACGGTCAGCCGATATTCAACATTATCGACAGCT 1700
1701 CGAATCTACAGGACCGGCGTGAACTTAAACTCGTCCTAATTCACACAGAG 1750
1751 AATGCTTATCGCAGTTCTGCACAAAGAAGTCTCATAGCTTCTCAACGCTC 1800
1801 GTGGATAAATTTCATCATTAATACTGATGTTCCCATTGATCCAGCTAAAG 1850
1851 ACGAAGTGGTCAAGTGCTCTCGCAAAGTTGCGTGCTGCCCAGACCCAACA 1900
1901 GATATACCCTTTGATATACTCAATGTATCTTTGCTGTACGTTTATTGCTC 1950
1951 GTTTCAAGAAATGCGAAGGTATGCACAACAGCGATTCTATGACGGCGTTT 2000
2001 CCGACGGAGGCGCAGTTATCTCCACCGTCCCACCCTATGCCGAAGGAATA 2050
2051 ACAAAACAAACTATGAGGTTGTGGCAGAAAAAAGTTTGGCAAAATACAAG 2100
2101 CAAAGAAACACATGATTTGGATGCTTACATTGCTCTTCTTCCGAATCTTC 2150
2151 GCTTCAAAATCCAAATTTCTCACATATGAAGATCGGCGGCAATAGCTTCT 2200
2201 TAGCGCCATCCCGGGTTGATCCTATCTGTGTTGAAATAGTTGCGGTGGGC 2250
2251 AAGGCTCTCTTTCAGAAAGACAGGCGGCCAAAGGAACCCAAGGTGAGGTG 2300
2301 GGCTATGGCTCTCAGTTCCTTGTGGAAGCGCTTGGTCTAAGGTGCAGAGG 2350
2351 TGTTAGCGGGGATGAAGCAAAAGTGTCCGATTGTAACAAGATATGTTGAT 2400
2401 CCTACGTAAGGATATTAAAGTATGTATTCATCATTAATATAATCAGTGTA 2450
2451 TTCCAATATGTACTACGATTTCCAATGTCTTTATTGTCGCCGTATGTAAT 2500
2501 CGGCGTCACAAAATAATCCCCGGTGACTTTCTTTTAATCCAGGATGAAAT 2550
2551 AATATGTTATTATAATTTTTGCGATTTGGTCCGTTATAGGAATTGAAGTG 2600
```

FIG. 1C

```
2601 TGCTTGAGCTCGGTCGCCACCACTCCCATTTCATAATTTTACATGTATTT 2650
2651 GAAAAATAAAAATTTATGGTATTCAATTTAAACACGTATACTTGTAAAGA 2700
2701 ATGATATCTTGAAAGAAATATAGTTTAAATATTTATTGATAAAATAACAA 2750
2751 GTCAGGTATTATAGTCCAAGCAAAAACATAAATTTATTGATGCAAGTTTA 2800
2801 AATTCAGAAATATTTCAATAACTGATTATATCAGCTGGTACATTGCCGTA 2850
2851 GATGAAAGACTGAGTGCGATATTATGTGTAATACATAAATTGATGATATA 2900
2901 GCTAGCTTAGCTCATCGATCCATGGGCTACTATGGGGTACAGAAATGGGC 2950
2951 GATTATGGCATCTCAGAAAGCCTTTCTCTGGATTTGAAACGCACAGGAAA 3000
3001 TAGTTGCTTTGAAAAATGGCGACATAATAAGTTAAATCACTTTGTTGCGC 3050
3051 CTTCATCTCAGCTGGCTTTATGGTAGTGAAGGATAATTCTTCCTTCTCCT 3100
3101 TAAATTTGAGGTGTGTGTCATGAATCCGCTGTGAGAGTGAACCTTTGCCA 3150
3151 TACAAATACAGCAGCCCATTGTTTGTTTGGATTACCTCTCCTGTTTCCAA 3200
3201 TTGTGGAGATGCACCATAAGTTTTGATAAACTCTTCGCATGCCCAGTCTA 3250
3251 GGTCGAGGGAGGCCAAGGGAGTATCTGCGAAATTCATGATGTGAGGTGTG 3300
3301 TTTGTGTAAGACAAACTATATTGGCGCTATATATAGATGCCGGGCTGGGA 3350
3351 CGACCTGTGGCGATGATTTCGGGGGGGGGCTTAATTTTCAAGCTTGAACT 3400
3401 AGTCTCATCTGAAGAAAATCCATAAAATGCTCGTCACGCTTGGCGGATTT 3450
3451 TGCGCTGGCTGCAATTGCTGACTTTTTGTAAGTCTGCGTTTATCTGTGTG 3500
3501 CCAAGTGGGCCGCCGACAGCGTAACGTCAATGGCTGACAATGATGATGTT 3550
3551 GTAGCAGGTGAGAGGTGCATCCAAATTAAAAGGTGGGTGCCTTCACGTCT 3600
3601 GTCCTCACACGGCGAGACAATTCAAAAAAGTCATTAATTTCATAATGCAG 3650
3651 ATTTGACAAATTTGTAAAGGATAGTGGACGGCAAATTATATATTATATAA 3700
3701 ATTGTATTAACTACTTTATGCCTAAATAGGATTGCTTGAACTTTAATTAT 3750
3751 ATTTCCCTATAATTTAGGAAAAATGTAATTTGCTTAAGATATATAATTTA 3800
3801 AATTCGAAAAAGAATTATTGTTATGTGAAGATGCCTATTCCAAGAAATAT 3850
3851 CTAAAGTTTATCACTGATAATAAAATTATTTATCGAACATGATTATTGCA 3900
```

FIG. 1D

```
3901 AAGACTTTTATTGGTTAAATCATAAATTAAAGTTTGTTCAAAATCTCCAT 3950
3951 CGCAAGTTATTATTCGATTTATAACATAAGGCACTGTTGTTCATAGACGC 4000
4001 AATACAAGGATTGATTGTCATCAATCTGAAAAATTGTAAAAACGAACATG 4050
4051 GTAGAAAGTTTAATTGGGTAAACCGGCAAAATATCGGAATCCAATGGCTT 4100
4101 CTTCCAATGCCCCCCCGATTGCTAACAGACGTTGGTCTGAATCCGCTAAT 4150
4151 CCATCGATCTCCATTCCAACAGGCAAGCGATCAGGTGTCAGGCAAACAGG 4200
4201 AATGCTCAAGCCAGGTAGGCCTGCGTTGCTGCTTGGGTCCACATTTCGCA 4250
4251 CGTAGATCTTGAATGTGTCCAGCATCGTGCCATTGTGGATAACTGAGGAA 4300
4301 TCCTGACCTATGGGTCTGGCCACCAAGGGTGCTGTTGGGAAGAGAATAGC 4350
4351 ATCTAATCTATTCAGTTTGAAGTAGTTGCGATAGGTGGCTTGAAGTCTTG 4400
4401 GTCTGAAGGAGTGGCGGGCCAGTTCATATTCAGCTTTGGAAATTTGATGT 4450
4451 CCATCAATTTGCGCATTGGCAATGTTGGCTACATCAGGGCTACGAATTCC 4500
4501 TTTGATGACGTCAGAAAAAGAAACAGTTTTTACAAAGTCGTCGAGATACT 4550
4551 GTTTTAGAGCGTGTGGAAATTCATAGAGTGCAACTGGGAAGCTGGCCCCT 4600
4601 TTATTCAGTTCGTCAAGGTGGGGAATGTTAGCTTCAACAAAAGTTACGCC 4650
4651 TTTGTTTGCTAGCAGGCGAATCGTTGTTTCAGCTGCTAGGGCCACATCAG 4700
4701 CATCAAGGTCATCATAAAAGTAGGTTGTAGGGAGGCCGATCCTTAGCCCC 4750
4751 TTCAGCGGCACGGGTGGTATTCTCTCCGGTGTGCCGGAAATTATCCGGTC 4800
4801 GAGGATTACAACATCGGCTACGCACTGCGCTATGATTCCGGGAGTGTCCC 4850
4851 GGGTAGGGCTAACCGGTATTATCCGATCTCCCGGATATCTACCAAGCGTC 4900
4901 GGTCGAAATCCTACTACGCCACACAGGGCTGCGGGTAGGCGAACAGATGC 4950
4951 ACCGGTATCGGTGCCTATGCCGCCTAACATCAATCGGCTTGCTACCGCAG 5000
5001 CAGCCACACCACCGCTTGAGCCCCCTGGTATCAGATCTGGATTCCACGGG 5050
5051 TTTCGCACCGCCCCGGTGGCATAGTTGTTGCTTGTAATTCCAAACGATAA 5100
5101 CTCATGCATATTTCCCGAGGCACCCGGCAGTGCTCCAGCTGAAAAAAGTC 5150
5151 TTTCTGCGACGCGGGATGGTATCTTTGGCAAGTGGTTTATCAGCGCCGGC 5200
```

FIG. 1E

```
5201 GTAGCGGCGCTTGTGGGAAATACGCCGGTAGCGATGTTCGCCTTAAAACA 5250
5251 GAGTGGAATGCCGCAAAGACCTACTCCGGCGTTTCCATGGCGATCAATTT 5300
5301 TTTTGGCGCTTCGCCGCAAACCATCCCAGTCTGTAGCCAGAAGGGCGTTT 5350
5351 AATGATTTTGCAGCTTCACAACGCGCTATCAGAGTTTCTACTAGTTCTAA 5400
5401 GCAGGAGTAGTCTTTCCGTTTCAGGTGTTCTAGGCTTTGGGCTAACGAGG 5450
5451 TAATGGCCACCATCTCTCTGAGTTGGAAATTTCAAACCCATTCAGACCAA 5500
5501 ATAAATATACCAAGCTTGAACCCAGCTTGCGCCATTATTGGTGGGAATTC 5550
5551 AGCAATCACGTCGTGTGATACGAATGACTGTAGGCACTAGGGTCGCTTTT 5600
5601 TCAAACGCAAACAGTATTGTATCAATTATCAATCAATATTCAACTTGATT 5650
5651 GAGCGGCGAGGTGGACCCGCATGAACATCATATTAAAGAAAGCCCAAATT 5700
5701 GTCGCTTTCCATTGGCATGTCAACGAACAGTATGTTCCCCGATTCTCAAC 5750
5751 TTAAATAGAAACGGTTGATGTGGTTATTTATCTACACAAAAACGAATCTT 5800
5801 TTCTAACAATGTCAGCTTCACCTCTCCTTGATAACCAGTGCGATCATCTC 5850
5851 CCAACCAAAATGGTGGATCTGACAATGGTCGATAAGGCGGATGAATTGGA 5900
5901 CCGCAGGGTTTCCGATGCCTTCTTAGAACGAGAAGCTTCTAGGGGAAGGA 5950
5951 GGATTACTCAAATCTCCACCGAGTGCAGCGCTGGGTTAGCTTGCAAAAGG 6000
6001 CTGGCCGATGGTCGCTTCCCCGAGATCTCAGCTGGTGGAAAGGTAGCAGT 6050
6051 TCTCTCCGCTTATATCTATATTGGCAAAGAAATTCTGGGGCGGATACTTG 6100
6101 AATCGAAACCTTGGGCGCGGGCAACAGTGAGTGGTCTCGTTGCCATCGAC 6150
6151 TTGGCACCATTTTGCATGGATTTCTCCGAAGCACAACTAATCCAAGCCCT 6200
6201 GTTTTTGCTGAGCGGTAAAAGATGTGCACCGATTGATCTTAGTCATTTCG 6250
6251 TGGCCATTTCAATCTCTAAGACTGCCGGCTTTCGAACCCTGCCAATGCCG 6300
6301 CTGTACGAGAATGGCACGATGAAATGCGTTACCGGGTTTACCATAACCCT 6350
6351 TGAAGGGGCCGTGCCATTTGACATGGTAGCTTATGGTCGAAACCTGATGC 6400
6401 TGAAGGGTTCGGCAGGTTCCTTTCCAACAATCGACTTGCTCTACGACTAC 6450
6451 AGACCGTTTTTTGACCAATGTTCCGATAGTGGACGGATCGGCTTCTTTCC 6500
```

FIG. 1F

```
6501 GGAGGATGTTCCTAAGCCGAAAGTGGCGGTCATTGGCGCTGGCATTTCCG 6550
6551 GACTCGTGGTGGCAAACGAACTGCTTCATGCTGGGGTAGACGATGTTACA 6600
6601 ATATATGAAGCAAGTGATCGTGTTGGAGGCAAGCTTTGGTCACATGCTTT 6650
6651 CAGGGACGCTCCTAGTGTCGTGGCCGAAATGGGGGCGATGCGATTTCCTC 6700
6701 CTGCTGCATTCTGCTTGTTTTTCTTCCTCGAGCGTTACGGCCTGTCTTCG 6750
6751 ATGAGGCCGTTCCCAAATCCCGGCACAGTCGACACTTACTTGGTCTACCA 6800
6801 AGGCGTCCAATACATGTGGAAAGCCGGGCAGCTGCCACCGAAGCTGTTCC 6850
6851 ATCGCGTTTACAACGGTTGGCGTGCGTTCTTGAAGGACGGTTTTCATGAG 6900
6901 CGAGATATTGTGTTGGCTTCGCCTGTCGCTATTACTCAGGCCTTGAAATC 6950
6951 AGGAGACATTAGGTGGGCTCATGACTCCTGGCAAATTTGGCTGAACCGTT 7000
7001 TCGGGAGGGAGTCCTTCTCTTCAGGGATAGAGAGGATCTTTCTGGGCACA 7050
7051 CATCCTCCTGGTGGTGAAACATGGAGTTTTCCTCATGATTGGGACCTATT 7100
7101 CAAGCTAATGGGAATAGGATCTGGCGGGTTTGGTCCAGTTTTTGAAAGCG 7150
7151 GGTTTATTGAGATCCTCCGCTTGGTCATCAACGGATATGAAGAAAATCAG 7200
7201 CGGATGTGCCCTGAAGGAATCTCAGAACTTCCACGTCGGATCGCATCTGA 7250
7251 AGTGGTTAACGGTGTGTCTGTGAGCCAGCGCATATGCCATGTTCAAGTCA 7300
7301 GGGCGATTCAGAAGGAAAAGACAAAAATAAAGATAAGGCTTAAGAGCGGG 7350
7351 ATATCTGAACTTTATGATAAGGTGGTGGTCACATCTGGACTCGCAAATAT 7400
7401 CCAACTCAGGCATTGCCTGACATGCGATACCAATATTTTTCAGGCACCAG 7450
7451 TGAACCAAGCGGTTGATAACAGCCATATGACAGGATCGTCAAAACTCTTC 7500
7501 CTGATGACTGAACGAAAATTCTGGTTAGACCATATCCTCCCGTCTTGTGT 7550
7551 CCTCATGGACGGGATCGCAAAAGCAGTGTATTGCCTGGACTATGAGTCGC 7600
7601 AGGATCCGAATGGTAAAGGTCTAGTGCTCATCAGTTATACATGGGAGGAC 7650
7651 GACTCCCACAAGCTGTTGGCGGTCCCCGACAAAAAAGAGCGATTATGTCT 7700
7701 GCTGCGGGACGCAATTTCGAGATCTTTCCCGGCGTTTGCCCAGCACCTAT 7750
7751 TTCCTGCCTGCGCTGATTACGACCAAAATGTTATTCAACATGATTGGCTT 7800
```

FIG. 1G

```
7801 ACAGACGAGAATGCCGGGGGAGCTTTCAAACTCAACCGGCGTGGTGAGGA 7850
7851 TTTTTATTCTGAAGAACTTTTCTTTCAAGCACTGGACACGGCTAATGATA 7900
7901 CCGGAGTTTACTTGGCGGGTTGCAGTTGTTCCTTCACAGGTGGATGGGTG 7950
7951 GAGGGTGCTATTCAGACCGCGTGTAACGCCGTCTGTGCAATTATCCACAA 8000
8001 TTGTGGAGGCATTTTGGCAAAGGGCAATCCTCTCGAACACTCTTGGAAGA 8050
8051 GATATAACTACCGCACTAGAAATTAGTCTATGGATCCTGTTACAAGTATT 8100
8101 GCAAGTTTTATAAATTGCATATTAATGCAATCTTGATTTTTAACAACGAA 8150
8151 CGTAATGGCGTAAAAAATGTATGTTATATTATTTATATTTAATTATATTG 8200
8201 GAGTGCGCCATAATATGATGATTTATAATTAAAAAATATTTACTGTCACA 8250
8251 TTGACTGAGATGGCACTGTTATTTCAACCATGAAATTTTGTTGATTTTTT 8300
8301 TACAATAACAATAATTGCAGGAAGTAAATAATAGACGCCGTTGTTAAAAA 8350
8351 ATTGCAATCATATGTGCCTAACTATAGGGACAATTAAGTCAATTGTAATA 8400
8401 GTCTCCCTTATTTTAACGACTCACCTAATCAAGTATTACAAAATATCTCA 8450
8451 CTTTTCGTCAGTAATGATGTAATCAGAACTGAATAGTACAAGTAAAACGT 8500
8501 GGAAAAACGTCATAGAGTGGCATGATTATATTCCTCTGCATTGCCAATTT 8550
8551 ATTCAGCTTTATTTGACTTAGGTGTGCCTTCGTTAGTGACAAATTGCTTT 8600
8601 CAAGGAGACAGCCATGCCCCACACTTTGTTGAAAAACAAGTTGCCTTTTG 8650
8651 GGATACGGTAAAGCCAGTTGCACTTCAATAATGAATTTCAAGGAGACAAT 8700
8701 ATAACCGCCTCTGATAACACAATTCTCTAATATAAAAATCAGTTTGTATT 8750
8751 CAATATACTGCAAAAAACTTATGGACCTGCATCTAATTTTCGGTCCAACT 8800
8801 TGCACAGGAAAGACGACGACCGCGATAGCTCTTGCCCAGCAGACAGGGCT 8850
8851 TCCAGTCCTTTCGCTTGATCGGGTCCAATGCTGTCCTCAACTATCAACCG 8900
8901 GAAGCGGACGACCAACAGTGGAAGAACTGAAAGGAACGACGCGTCTCTAC 8950
8951 CTTGATGATCGGCCTCTGGTGGAGGGTATCATCGCAGCCAAGCAAGCTCA 9000
9001 TCATAGGCTGATCGAGGAGGTGTATAATCATGAGGCCAACGGCGGGCTTA 9050
9051 TTCTTGAGGGAGGATCCACCTCGTTGCTCAACTGCATGGCGCGAAACAGC 9100
```

FIG. 1H

```
 9101 TATTGGAGTGCAGATTTTCGTTGGCATATTATTCGCCACAAGTTACCCGA  9150
 9151 CCAAGAGACCTTCATGAAAGCGGCCAAGGCCAGAGTTAAGCAGATGTTGC  9200
 9201 ACCCCGCTGCAGGCCATTCTATTATTCAAGAGTTGGTTTATCTTTGGAAT  9250
 9251 GAACCTCGGCTGAGGCCCATTCTGAAAGAGATCGATGGATATCGATATGC  9300
 9301 CATGTTGTTTGCTAGCCAGAACCAGATCACGGCAGATATGCTATTGCAGC  9350
 9351 TTGACGCAAATATGGAAGGTAAGTTGATTAATGGGATCGCTCAGGAGTAT  9400
 9401 TTCATCCATGCGCGCCAACAGGAACAGAAATTCCCCCAAGTTAACGCAGC  9450
 9451 CGCTTTCGACGGATTCGAAGGTCATCCGTTCGGAATGTATTAGGTTACGC  9500
 9501 CAGCCCTGCGTCGCACCTGTCTTCATCTGGATAAGATGTTCGTAATTGTT  9550
 9551 TTTGGCTTTGTCCTGTTGTGGCAGGGCGGCAAATACTTCCGACAATCCAT  9600
 9601 CGTGTCTTCAAACTTTATGCTGGTGAACAAGTCTTAGTTTCCACGAAAGT  9650
 9651 ATTATGTTAAATTTTAAAATTTCGATGTATAATGTGGCTATAATTGTAAA  9700
 9701 AATAAACTATCGTAAGTGTGCGTGTTATGTATAATTTGTCTAAATGTTTA  9750
 9751 ATATATATCATAGAACGCAATAAATATTAAATATAGCGCTTTTATGAAAT  9800
 9801 ATAAATACATCATTACAAGTTGTTTATATTTCGGGTACCTTTTCCATTAT  9850
 9851 TTTGCGCAACAAGTCACGGATATTCGTGAAAACGACAAAAACTGCGAAAT  9900
 9901 TTGCGGGCAGTGCCTTCAGTTTTCCTTATTAATATTTAGTTTGACACCAG  9950
 9951 TTGCTATCATTGCGGCCAAGCTCAGCTGTTTCTTTTCTTGAAACGATGGA 10000
10001 TCGAATGAGCATGGCTCGGCAAGGTTGGCTTGTACCATGTCTTTCTCATG 10050
10051 GCAAAGATGATCAACTGCAGGGTGAACTCTCGGAGCTTTCAAAAGTTTAT 10100
10101 CGGGAAAAGTTTCAAACCGATCTACACACTAAGTCTGGCGACATCATCAA 10150
10151 TCCTGGCGGGGAATTTCTGTACATTTATCTCGATAAAGAGAATTATCGGT 10200
10201 TATGTCGGCAAAGAATGGTTCTAGTTTCAAATGCTTCAGATGGATTGCTT 10250
10251 GCCACGACACTGGAACCCTATTCTGATGGTTATACATTCCGGCAGGTGAG 10300
10301 GGCGCAACTGCAAGCCTTAAGCGGAGACGGTGGTCGGATCAACTACAGCA 10350
10351 AAAATGAATATTCATCCTCGTACTTTCTAGCAATTCAGGCCAGCAACGAG 10400
```

FIG. 1I

```
10401 TTCGAACGCATAGGAGTCGTCCGGAACACTTTTGGACAAAGCAAGGACGT 10450
10451 TTGGAAAAGGAAAATGCCAAGCGCCGGCCAACCATTGGATTATCTTTTGA 10500
10501 TCGCTGTGGGCTGTTCAGCTTTCCTCCCGGAGGCTGCTCTTGAAGACGTG 10550
10551 GAGTTAGATGGTGCTATCTAGTTTTTATGGGGCGGGATTTCGAAGTCTAT 10600
10601 GTCGTTTTGGTTGTTGCATCATAGAGGTGCTTATAAAATCTTCTGTTAAA 10650
10651 TCAAGGAGTGTCTGAGAACTTTGTTGAATTAATTATTAATGAATAAGACA 10700
10701 ATTGTGTTCGCTTGTAATTTTCGCCATGTTCATCGTGGGCTTGATAAATG 10750
10751 TTATATTTAATTCTTCTTCTTGTGTGATCGTGGTGATATTAAAGAGAGTT 10800
10801 ACAAAATTATTTCGAAACAGGATTTTTCGGCAATGATTAGAAATATAAGC 10850
10851 TCGTATAGATTATTACCAGGCTAGCTTAGAACACTTTTAGAAAAACTAGC 10900
10901 GATGGGTGGCGATGTTTGCCGAAAACACAGCCTGCTTTTAGAAGAGGATA 10950
10951 ACGTTTATTTCGTTACTAAATGACATTGGAAACATGCAAAATAACAAAGT 11000
11001 CAAGACACACTCAATCACATAGATTAGCCGACTTTATTAGGTGTCGGCGA 11050
11051 CGGGAATTATGCGGAAAGATCGCATGACCCTAAAGCAATGATCGGATAAT 11100
11101 TGATAAGGTTTCCGATCTGACACTCTCTTGGTTCCGCTCCACCAGCCTCC 11150
11151 CCTTCATCGTCCATCTCATCGTCGTCATCTTCTCCTTCCTCTAGTGTATT 11200
11201 CCTCCCCGGGCTTAAAACCGTAGTTTTCATTGTTGATTATGTCGGTCCCG 11250
11251 AACCGAACAAAGCAGTTGCTTGGCATAATCGCCAAAAAGAACTGATTTGT 11300
11301 ATGTGGGCCTTGATAGTAGTTGACGAGGCCACCTTGATCGCACCTTTCCT 11350
11351 GCATAACTCGATTCAGGCTGCGTGCATTCATCAGCCACGGCGGTATTGCA 11400
11401 GTTGCCATTGTTCCGAAGTTAGAGGAGTTGGACGGTAGGTTTCGACGCAA 11450
11451 GGCGCATTGGCGTGCAATATCTTCACGAAGGTATACATAGACCAGCTCTT 11500
11501 GTCGAGAGTGGATGTACTCGTCATCAAACTCACCAAGTCTAATCGCGGAA 11550
11551 GGCTGAAAGTATACAGTTTCGGACAGTAACGCTCCGAAATCCGTTCTCGC 11600
11601 CTGTTCCAAGCGACTCTTCATCTCGCCGGTGCGCAGGATAAGCGTCAAAT 11650
11651 CTCGAACCTGCCAATTAGCTACCGTCATCGCAGTGTTGGATGTACTACAA 11700
```

FIG. 1J

```
11701 ATACCTGCCGCTGGTAAGTCTGAGCCGTTGGTTTTTATATTGACTAAGGA 11750
11751 AGCCCATTGACGTCATTGGTGACCGTTTGATGCCGTGTGAACACGACAGA 11800
11801 TTGATAGCATTGACTAGCGCGTTTGAATTTTCAGCTGCTGAGCCTCGACA 11850
11851 TGTTGTCGCAAAATTCGCCCTGGACCCGCCCAACGATTTGTCGTCACTGT 11900
11901 CAAGGTTTGACCTGCACTTCATTTGGGGCCCACATACACCAAAAAAATGC 11950
11951 TGCATAATTCTCGGGGCAGCAAGTCGGTTACCCGGCCGCCGTGCTGGACC 12000
12001 GGGTTGAATGGTGCCCGTAACTTTCGGTAGAGCGGACGGCCAATACTCAA 12050
12051 CTTCAAGGAATCTCACCCATGCGCGCCGGCGGGGAACCGGAGTTCCCTTC 12100
12101 AGTGAACGTTATTAGTTCGCCGCTCGGTGTGTCGTAGATACTAGCCCCTG 12150
12151 GGGCCTTTTGAAATTTGAATAAGATTTATGTAATCAGTCTTTTAGGTTTG 12200
12201 ACCGGTTCTGCCGCTTTTTTTAAAATTGGATTTGTAATAATAAAACGCAA 12250
12251 TTGTTTGTTATTGTGGCGCTCTATCATAGATGTCGCTATAAACCTATTCA 12300
12301 GCACAATATATTGTTTTCATTTTAATATTGTACATATAAGTAGTAGGGTA 12350
12351 CAATCAGTAAATTGAACGGAGAATATTATTCATAAAAATACGATAGTAAC 12400
12401 GGGTGATATATTCATTAGAATGAACCGAAACCGGCGGTAAGGATCTGAGC 12450
12451 TACACATGCTCAGGTTTTTTACAACGTGCACAACAGAATTGAAAGCAAAT 12500
12501 ATCATGCGATCATAGGCGTCTCGCATATCTCATTAAAGCAGCTGGAAGAT 12550
12551 TTGATTCAAACTCCATTGAGAGCCCTGACTATGGCATTCGCGTTTGAACC 12600
12601 TTCCAGGTTGAGAGACGATAGCCCCCTACCAGTATGAGAGAGGTCCTCGT 12650
12651 TCAGCACGTCGCTTGCCTCCTGCACTACAGATTTCATTTCTGGAACTTGC 12700
12701 ACGCCGATCACTTCAGCTATCTCAACCCAGAGCACCAAAATGTGCTTCAC 12750
12751 GTCCTCACTAAGGTAGCGATGGTTCATGTTTCTTGGAGTTTCGATATCAG 12800
12801 CGTAGCCCTCAAAGGTCTCATAGAATTCTCTTGCGTTGCTGGCGTGCCCA 12850
12851 CCATACCATTTTTTGCAGTATGCGAAATCCGTCTCGGACTCAAGTCCAAG 12900
12901 CGCATTAACAATCGTAAGGCGTTCCTCGTCTATTGCGGTAACACGCGTGA 12950
12951 TGGCTTGTGGGACAAACTTCCGGTAGAATTTTGGGATCGGCGATATCCCT 13000
```

FIG. 1K

```
13001 TGCTCGATGGTATCTTTTGCAGCGAGAATTCCAGCAGGGTGAGCAACAGG 13050
13051 GTTGGTATTTGAAAAAAATATCGACGCGGGATTTTGATACCACTGAAGCC 13100
13101 GATTTGGAAAGAGAATCTCGAAGCCCCCCCTAACCTCTTCGCTCAAAGCC 13150
13151 TGAGTTGACGCAACTTCGAACGTTCTCTTCACACTTAGCATTAGCACCTG 13200
13201 TGCATTGACACGGCGGCATGCATAGGGAGATGTCGTTGCTTCGATGACGG 13250
13251 CGATAGGTGCAAAAGCTGGAGTTAAAGTCTGCTTGCATGCCAGAGACGTT 13300
13301 GCGCTACCGGGCAATGCTACGAGGACCGAGCTGCTCAGATTGAAGTTCGC 13350
13351 CAACTCGCAAAGAATTCCTTGCTGGCCCATGGTCGGGACCGTAAGAAAAA 13400
13401 TGAACGCCGCGCCTGAAATCGCTGTTTCAAGATCATCCTCCAATTGCGGC 13450
13451 TGAAAGTCGCCTCCATAGTCCGGCCCTACTAGCTCCAAGGAGCCAAGGGA 13500
13501 CCTCACAGAGTTGAAGCTGTTCCTGTTGGAGATTGGCGCCCAGATTGAGG 13550
13551 ACACCTGGCCGAGCCTCCGGGCGAGATCACCTGCAAGAGTAAGAGCCACG 13600
13601 TTTCCCGCACCCAAAATTGCCACTTTAGCCATTTGGTAGATTGCAAATAT 13650
13651 AATGGTTTGGCGATTATCCTTGAGGCCACACCTTTAAATAGATCAATGAA 13700
13701 TGGGCAAGTATTGACTTGCGATAATCCTTTAACTTTCTGCCTACCATCAA 13750
13751 TGTGGATGAGTTGTCGGTAAAAAGGATCCCTGAAAGCGACGTTGGATGTT 13800
13801 AACATCTACAAATTGCCTTTTCTTATCGACCATGTACGTAAGCGCTTACG 13850
13851 TTTTTGGTGGACCCTTGAGGAAACTGGTAGCTGTTGTGGGCCTGTGGTCT 13900
13901 CAAGATGGATCATTAATTTCCACCTTCACCTACGATGGGGGGCATCGCAC 13950
13951 CGGTGAGTAATATTGTACGGCTAAGAGCGAATTTGGCCTGTAGACCTCAA 14000
14001 TTGCGAGCTTTCTAATTTCAAACTATTCGGGCCTAACTTTTGGTGTGATG 14050
14051 ATGCTGACTGGCAGGATATATACCGTTGTAATTTGAGCTCGTGTGAATAA 14100
14101 GTCGCTGTGTATGTTTGTTTGATTGTTTCTGTTGGAGTGCAGCCCATTTC 14150
14151 ACCGGACAAGTCGGCTAGATTGATTTAGCCCTGATGAACTGCCGAGGGGA 14200
14201 AGCCATCTTGAGCGCGGAATGGGAATGGATTTCGTTGTACAACGAGACGA 14250
14251 CAGAACACCCACGGGACCGAGCTTCGCGAGCTTTTGTATCCGTGGCATCC 14300
```

FIG. 1L

```
14301 TTGGTCCGGGCGATTTGTTCACGTCCATGAGGCGCTCTCCAAAGGAACGC 14350
14351 ATATTTTCCGGTGCAACCTTTCCGGTTCTTCCTCTACTCGACCTCTTGAA 14400
14401 GTCCCAGCATGAATGTTCGACCGCTCCGCAAGCGGATCTTTGGCGCAACC 14450
14451 AGCCGGTTTCGCACGTCGATTCTCGCGAGCCTGCATACTTTGGCAAGATT 14500
14501 GCTGAATGACGCTGATGCTTCATCGCAATCTGCGATAATGGGGTAAGTAT 14550
14551 CCGGTGAAGGCCGCAGGTCAGGCCGCCTGAGCACTCAGTGTCTTGGATGT 14600
14601 CCAGTTCCACGGCAGCTGTTGCTCAAGCCTGCTGATCGGAGCGTCCGCAA 14650
14651 GGTCGGCGCGGACGTCGGCAAGCCAGGCCTGCGGATCGATGTTATTGAGC 14700
14701 TTGGCGCTCATGATCAGTGTCGCCATGAACGCCGCACGTTCAGCACAACG 14750
14751 ATCCGATCCGGCAAACAGCCATGACTTCCTGCCGAGTACATAGCCTCTGA 14800
14801 GCGTTCGTTCGGCAGCATTGTTCGTCAGGCAAATCGGGCCGTCATCGAGG 14850
14851 AATGACGTAATGCCATCCCATCGCTTGAGCATGTAATTTATCGCCTCGGC 14900
14901 GACGGGAGAACTGCGCGACAATTTCCCCCGCTCGGTTTCGAGCCAATCAT 14950
14951 GCAGCTCTTCGGCGAGTGACCTTGATCAGGCCACCGCCACGACCGCGGAA 15000
15001 GACGAACAGATGCCTGCGCATCGGATCGCGCTTCAGCGTCTCTTGCACCA 15050
15051 TCAGCGACAAACCGGGAAAGCCTTTGCGCATGTCCGTACTTATGTCGCCA 15100
15101 CTTGGGAGGGCTTCGTCTACGTGGCCTTCGTGATCGACGTCTTCGCCCGT 15150
15151 CGCATTGTCGGATGGCGGGCGAGCCGGACAGCACATGCAGGCTTTGTCCT 15200
15201 CGATGCCCTCGAGGAGGCTCATCATGATCGGCGTCCCGCTCATGGCGGCC 15250
15251 TAGTGCATCACTCGGATCGCGGTGTTCAATACGTGTCCTTTCGCTATTCC 15300
15301 GAGCGGTTGGCAGAAGCAGGTATCGAGCCATCTATCGGAAGCGTCGGCGA 15350
15351 CAGCACGACAACGCCCTCGCAGAAGCGATCAACGGTCTTTACAAGGCCGA 15400
15401 GGTCATTCATCGGCGTGGACCATGGAGGAGCTTCGAAGCGGTCGAGTTCG 15450
15451 CTACCTTGGAATGGATAGACTGGTTCAACCACGGCGGCTTTTGAAGCCCA 15500
15501 TCGGCAATATACCGCCAGCCGAAGACGAGGATCAGTATTACGCCATGCTG 15550
15551 GACGAAGCAGCCATGGCTGCGCATTTTAACGAAATGGCCTCCGGCAAACC 15600
```

FIG. 1M

```
15601 CGGTGCGGTTCACTTGTTGCGTGGGAAAGTTCACGGGACTCCGCGCACGA 15650
15651 GCCTTCTTCGTAATAGCCATATCGATGTGGCCTTAGCGTTTGCAATTGTC 15700
15701 CGCCTCTCTCCTTCATCTACTCAAGTAGCGCTACTTACAATCGGAAATTG 15750
15751 GATACGAGAAACAGGTAACAGGCCATTGCTGCAAGCACCGCGAGACCACG 15800
15801 ACGCCAGTCGCCGGTCCGCAGTTAGCGGGAATAGCGACCGAGGGTCCGAA 15850
15851 AAAGTCTGCCCAAATCTAGCGCTTTTTTGCTAGAACTTTGAGAAAAGGTG 15900
15901 GCAGGATATATCGAGGTGTAAAATATCATTTGGGCATTGATCATAATGGG 15950
15951 TTAGTTGATGTTTTATTTTTTCCGCTACTCGGTTTTGTTTCAGTTATTCG 16000
16001 CACCCGCTAGAATGGGTGCCGTGAAGTTTTACAATAATTAATCCGAGCCC 16050
16051 AAATCTGAGAAATTCGCATACCCTACTTGGACTTCTAGGGACGCGGCACA 16100
16101 AGAAACTAGCAAATTTGGAATTTTCGCTTAATTTATGTAAGATTGGCCTG 16150
16151 TTTCCGAATTATTAAAGATATTGTTCTCTTAAGAGATAATCCAGTAATTG 16200
16201 AGAATTCGTGCCAATCCATTTTGTTTTGATTGTCTTGTAAAGTTTTTCCT 16250
16251 TTCGACCCGCTAATCACGGATTGAAAAATCAACGCTTCACTCCTTTCGAC 16300
16301 TTTTTTAAAGCCGTTTCTAAAATGAAATTCTAATCTTTGAAAATGGAAAT 16350
16351 TTATGCTATATGACTTTATCGCCGTGAATAATTAAAGGAGATTCAGACGG 16400
16401 AACTTTAGGCGCTCATTTCGCGACTGGCCCACGGATGATGTAAAACACTA 16450
16451 CCTAACAAATTTGAAAAAGACGCCAACCACCGATATAGCCGGTCCAAAGT 16500
16501 CGCATCCACTGAAGTACTCATGATCTTTTGAAGGGTAAAAATGTGCTTTA 16550
16551 GGTCCACTAATTCCCCTGTTGAGTAGGTAACGCCTCAATATATGGAAATT 16600
16601 GCCTCCGAATTTCTCAATTCAATCTTTTGGCATTGTGAGCGGACTCCTAT 16650
16651 AAATATTAGAACCTCTGCCCTTGCACTCGCCATCGAAACATCGAGCAATG 16700
16701 AGTTATTATTGGATAGACTTAAGGCGCAAGCCCGCCGGAAGCGTAAAAAA 16750
16751 TTTAATAGATGACCAGCAAAATTTGATTAAGCGCACTTGGAGTAGCAAAT 16800
16801 TTCAAATTCCGGATACCAGCGAAGTTGTTGAGACAAGCAAGCTATACTTT 16850
16851 CTATACGGGACGAGCGAATTGCTCAAAGATTTCAATGAGCAAACTGGTTC 16900
```

FIG. 1N

```
16901 TCTCCTGATGGATGAAAAAGCGACGTGGGGGGTGTCTGACTTAGGCCCCT 16950
16951 GGCAGTTGCCGTTAGGCTTCGTGAATGCAAACGTCTTCACAACCTACATT 17000
17001 GCGCTGTTCAAGAGCAACCTGTTCAAGGCTGAGAAGCACGACTTTGTCAA 17050
17051 ATGCTCGCGCTGCGCGGTTAAGGTCAACTATCCTGTCGTCGCCGTCGGGT 17100
17101 CGCTCCCGTAACACGCGATGACAAAATCAGAGCTAGGTCGCAGTACTATC 17150
17151 AAGCGAGGCGCCTTAAATCTCTTGTTATCTAGTTTATTTACACCATTTCG 17200
17201 TAGCTGTACCGTTTCTACTTAAATGTTGTAATGTTGCCTCCTTAATAATA 17250
17251 ATTGATCGTGTGATTTTTAATATTTACAGATGAAATTAATCGAAATTCCT 17300
17301 ACTGAAATATTTTACAAAAATGTTGTCTCTTTATTGCCAAATTCTAAAAA 17350
17351 TGCATAAATCGTATTCCATTGTAAATGATTAAAGATTTTAACTGTTAAAT 17400
17401 TGCAAGAATTGCGAAGAGGGCCTTCCCGCTTTTCGACATTGAAAAAAGAA 17450
17451 TTGGTAAAATTCAAACACGAGAACAGTATAACTGATAAAAATGTGGAACT 17500
17501 GAAAATTGATCTGATAATGTCCAGTATCCTCCCCTTCATCTTACACTTTA 17550
17551 CGTTCGCTATTATCATACACTTTAGCGTAATTTGCAGGGTGGTGTAGCAT 17600
17601 GCGCACCCCATTTATAATTAACTGAAAATTTCAAATCGAATTTATGACAA 17650
17651 GATTCGGAGGCCCACTATCCGACAGGCGTGAAGGCTTTCGGCTCGCTTTT 17700
17701 GACATTTTGTGCCAGACTTTTTTTGTGGGTCCTACCGCCTCGACTTTTTG 17750
17751 TATGGTTAAGAAGGTCGTAGCTGTAATTTTGGGATCTTGTGGAAAACTAA 17800
17801 CACATTATAAATCAATTGATGTTTTCAGACCTCAACTGGAAACCCAGAAA 17850
17851 TGGAGTATAATCGTCCACATTTCCAACCGACTTATGTCAATTTCTTATCC 17900
17901 GCTTCTCAGGTGGGAAACTCCATTCTTGCTGGATCAAAGGAAGCGTATTT 17950
17951 AACGTATCTAAATTCAACCCTCGCGAGCGCTCAGAAATCGTGGGCGAAAT 18000
18001 CTATTATAAAAGCTGGGCTGATGATATCCGACGAGAACTTAGAGTGTTTT 18050
18051 TCCGAAGTGCCATGTTTGCACGGTCCTGATTTCGACAGTCTAGATGTCGT 18100
18101 TCTTCCTGACTATGACCTATTGTATTTTTACGGTACGTCACACGAAGTTC 18150
18151 AACAATTTGTGGAGTGCGGAAACTTTTTGTGCACACACGCCTCAAGATTT 18200
```

FIG. 10

```
18201 GTGGCATGTACTGAATCGCCTTACACGGAGGGAGTGACGGCCCAAACCAT 18250
18251 ACGCAACTGGTATAACATGATTTCGCCTTGTTCTCGACTTTCGTTGAATG 18300
18301 ATGTGGGGGCGTTCTTCGCCTTTCTTCCGAGTGTATCCTTTTTGAGTACG 18350
18351 GTACACACCGTTGTCGAAATCCATGGTACACATGTCCGCAAGTTTCTTGC 18400
18401 TCCGGCAGCAGGTTCATGGTTTAGAGGTGAAGTTGTCGCGTTTGGAGCCG 18450
18451 CCTTTCCTCCGCGGCCTGAGCTCCGACCAACCGCAAGCGTTGTCAGTGTT 18500
18501 GCAAAGCGCTCTGTGTGGGCCTACTTTAATTGCTTCCAGTGTTAAATTGG 18550
18551 CGAAAGGCAATAATATCGCAAAATATTGTGTTGTAAAATGTAATTATGTT 18600
18601 TTAATTTCATGGAAATGTTTGAGCATAATTTTTATTAATGTACTAAATTA 18650
18651 CTGTTTTGTTAAATGCAATTTTGCTTTCTCGGGATTTTAATATCAAAATC 18700
18701 TATTTAGAAATACACAATATTTTGTTGCAGGCTTGCTGGAGAATCGATCT 18750
18751 GCTATCATAAAAATTACAAAAAAATTTTATTTGCCTCAATTATTTTAGGA 18800
18801 TTGGTATTAAGGACGCTTAAATTATTTGTCGGGTCACTACGCATCATTGT 18850
18851 GATTGAGAAGATCAGCGATACGAAATATTCGTAGTACTATCGATAATTTA 18900
18901 TTTGAAAATTCATAAGAAAAGCAAACGTTACATGAATTGATGAAACAATA 18950
18951 CAAAGACAGATAAAGCCACGCACATTTAGGATATTGGCCGAGATTACTGA 19000
19001 ATATTGAGTAAGATCACGGAATTTCTGACAGGAGCATGTCTTCAATTCAG 19050
19051 CCCAAATGGCAGTTGAAATACTCAAACCGCCCCATATGCAGGAGCGGATC 19100
19101 ATTCATTGTTTGTTTGGTTGCCTTTGCCAACATGGGAGTCCAAGGTTTCA 19150
19151 GGGAGCTTCGCAAATGAGGGCGCCGACGATTTTAAGGACTTCTGGGTCTA 19200
19201 TGCCCGAAGTGTCGAAATCCTTGGTATCAAGCACGTGAAAGCTTACCGGA 19250
19251 TAGTTTTTGACGGTTTGTTCAAAAAAAGTCTTTATATCCAGCATGCTACC 19300
19301 CCGGCTCCCATCTCCTGGGACGGTGAGAATAAAGCGCGCCTTCGTACCAG 19350
19351 GACGCACTGTCTCCACGACACTGTGGAAAAAGTCAGTGGCGTCAACAACA 19400
19401 TGCACGTCGAACCCGAACCTTTCCTGGAGAACGCAAAGCCCGTAAGCGTG 19450
19451 CGGGACGAGCAGGCCAGATCCTGAGGCTATGAAATAAAGGGGGGTATCAC 19500
```

FIG. 1P

```
19501 TCTTGAAGTCTTCAGCAAATGCCTCTCCAGCCAACACACACTTCCTTGCA 19550
19551 GCATGGAACAACGCCACCGGTAGCGCTTTCAGGGATGATGCCAGGGCTGG 19600
19601 CATAAAGCTCCAACTTTCTTTGATTTCCAAAATACCGCCAGTAAATGACG 19650
19651 CCATTAGCATGTGGGTAGCATGGAAAGCCTGGGTTGTTTCCCCGGTGAAA 19700
19701 AACGCACTGTGACCATATGAGGCGAGCGGAGTGTCTTGGGACTTCGTAAA 19750
19751 GACGACTGTTTTACAAGGCTTGTTTTTCAGGGCCTTCGCTGCTTCTACAG 19800
19801 TTTCTGGAGTTTTCCCAGACTTTGAAGACAGGACAATCAATGTGTCTGGA 19850
19851 GCATCAGCGATTGATGGTTTGGCTTTCATTAGGTCCACGAATCTCGAAGC 19900
19901 GGCGTAGCTAATGAAACGGAGGTTTTGCGCAACCTCGTCAGTATACGCAT 19950
19951 TCAAGCTTTTTCCAATTGCCAACCCAGCACCAGCAGATACGAAGAACACC 20000
20001 TGCCTCAGTCCAGTGGCGGCTACACGGCGCCCGGCTTCTGCGACATTTTC 20050
20051 AAGCTGCCTGATTGTAGAGTCGAGTTGTTGAGCGATCTCGGATGATCCGG 20100
20101 TTGAGAGGGGTGCATACAGCATGTCCATCGATTTGGTGTATCGAGATTGG 20150
20151 TTATGAAATTCAGATGCTAGTGTAATGTATTGGTAATTTGGGAAGATATA 20200
20201 ATAGGAAGCAAGGCTATTTATCCATTTCTGAAAAGGCGAAATGGCGTCAC 20250
20251 CGCGAGCGTCACGCGCATTCCGTTCTTGCTGTAAAGCGTTGTTTGGTACA 20300
20301 CTTTTGACTAGCGAGGCTTGGCGTGTCAGCGTATCTATTCAAAAGTCGTT 20350
20351 AATGGCTGCGGATCAAGAAAAAGTTGGAATAGAAACAGAATACCCGCGAA 20400
20401 ATTCAGGCCCGGTTGCCATGTCCTACACGCCGAAATAAACGACCAAATTA 20450
20451 GTAGAAAAATAAAAACTAGCTCAGATACTTACGTCACGTCTTGCGCACTG 20500
20501 ATTTGAAAAATCTCAATATAAACAAAGACGGCCACAAGAAAAAACCAAAA 20550
20551 CACCGATATTCATTAATCTTATCTAGTTTCTCAAAAAAATTCATATCTTC 20600
20601 CACACGTGAAAATGCCAATTTCTCAGACCTACCTCGGCTCTGCGAAGGCC 20650
20651 CCCGCTGGTATCAAAAGTTTTTATTTCATCCGACATGGCGCGACCGACCT 20700
20701 CAACGAGAAGGAAATTGTCGTGAACGGTGAGAAGCTCTGGGGCGTGCAAG 20750
20751 GTTCCGGAACGAACATCGGTCTCAATGCAAAAGGGGAACGCCAGGCTCTG 20800
```

FIG. 1Q

```
20801 TTGGCCGGCAATGTTCTTCGGTCGCTTCCAATAAGCGGTGTTGTCTGTTC 20850
20851 ACCGCTTTTACGTGCACTTCAGACTGCCTTCATCGCTAATCCGGGCTGCC 20900
20901 CCAGCTTCCAGATTGCAAATGATCTTCAGGAGCGGGATTTTGGTACACAC 20950
20951 GAAGGGGGCTTCGGCCCGCTTCAGATGTTTGAGGACGACTATCCCGATTG 21000
21001 TGAATCTACTGAAATCTTCTCAATCCATGTCGCCAAGGCTCTCAAGCACG 21050
21051 CATGTAGAGAAAACGTGCTTCTCGTCGCCCATGGCGGTGTGCTCAGGGTT 21100
21101 GTTGCGGCACTACTAGGGGTTGCTATAACTGACGAGCATACCGCCAACGG 21150
21151 GCGTGTTCTACATTTCAGTGTGGTTGCTGACAATTGGTCTGTGCGTGTAA 21200
21201 TCCAAAGTCCTGTGGTTATGGTCAGTGGCGTAACTCGCGGCATAGGCAAG 21250
21251 GCCATCGCAGAAGACCTTATCAGGCACGGCTATCGAGTAAGTCTGGGTGC 21300
21301 GCGTAACATACAAGACCTAGTAGCAGCTTTTGGCGACGAGAACGAAGCTC 21350
21351 TTCACTACGCACGTTTTGATGCACTGGATCATAGCTCGATGAAAGATTGG 21400
21401 GTGGACACGACCATCGCGAAATTTAACAGGATCGATGGCTTAGTAAACAA 21450
21451 TGCTGGCTGTGGCGATCATGTTGACCTCGAGAAAGAGATCAATGTTGAGC 21500
21501 TGCTTCAAAAGCAATGGGATATCAACTGCGTGGCCCCTCTGATCATGACA 21550
21551 AAGCTATGCATGCCATATCTGATTGAATCTGGTTCTGGCCGCATCGTTAA 21600
21601 TCTCAACTCAATGTCTGGCCAGCGTGTAGCGAATTCATTGGTTGGCTACA 21650
21651 ATATGACCAAGCATGGGCTGGCAGGCCTCACGAAAACAACTCAACATGTG 21700
21701 GGATGGGACCATGGCGTGCGGGCCGTTGACATATGCCCCGGTTTCGTTGC 21750
21751 GACTAACATGAGTTCTTGGACAAATTTGATTGGACCTGATGAGATGATCC 21800
21801 AACCCGAGGATATAGCAAAGCTCGTTCGTGCAGCAATGGAACGGCCAAAC 21850
21851 CGTGCTTTTGTCCCCAAGAATGAGGTGCTATGCATGAAGGAATCTACCCG 21900
21901 TTGATGTCCAACAGTCTCAGGGTTAATGTCTATGTATCTTAAATAATGTT 21950
21951 GTCGGTATTTTGTAATCTCATATAGATTTTCACTGTGCGACGCAAAAATA 22000
22001 TTAAATAAATATTATTATTATCTACGTTTTGATTGAGATATCATCAATAT 22050
22051 TATAATAAAAATATCCATTAAACACGATTTGATACAAATGACAGTCAATA 22100
```

FIG. 1R

```
22101 ATCTGATTTGAATATTTATTAATTGTAACGAATTACATAAAGATCGAATA 22150
22151 GAAAATACTGCACTGCAAATGAAAATTAACACATACTAATAAATGCGTCA 22200
22201 AATATCTTTGCCAAGATCAAGCGGAGTGAGGGCCTCATATCCGGTCTCAG 22250
22251 TTACAAGCACGGTATCCCCGAAGCGCGCTCCACCAATGCCCTCGACATAG 22300
22301 ATGCCGGGCTCGACGCTGAGGACATTGCCTACCTTGAGCATGGTCTCAGC 22350
22351 GCCGGCTTTAAGCTCAATCCCATCCCAATCTGAATATCCTATCCCGCGCC 22400
22401 CAGTCCGGTGTAAGAACGGGTCTGTCCATCCACCTCTGTTGACTACAGCC 22450
22451 ACTGCAGCCGCATGGACCTCACGTGCCATCACTCCCGGACGTATCGCCGA 22500
22501 CAAAGCAGCCAACTGCGCGTCACGCGCGTTTTTATAACCTTGAGAATATC 22550
22551 ACCCGACAAGGGTTTTGAACCAACAGGGAGAGGGCGGTCGAAACGGACTG 22600
22601 CGTGCCCACGGAACAGCTGACCGCATAAGCAAACTTGTACATGTTCGCCG 22650
22651 TCTTGCATTATCCGGCCGCCACCGGAAGTGTGGCATCTTGCTGTTCGATT 22700
22701 GGCACCACTACCAACCATATTTAGTTGATGAGGCCAGAAACGTGGTAGCT 22750
22751 CCTCATTTTCACCCAGCAATTGACTGTTTCTTTCAATGGCAGTCTGGACG 22800
22801 CTAGCAAGGGTGACACGCCATTCACAAGTCCCTGGTGAAATAACTTGACG 22850
22851 GCACTCCATGAATTGGTGACCCACAATGTCGCAGCTCTGCTTGATAGCTG 22900
22901 CAATTCCTTCTGCATCCTTGCAGGCCCAGAGATCTTGCAAGAGCAATGTC 22950
22951 ACATCCCTGACCCGCTCCGCTCCAAACGTCCGCTTAATCAATTCGAGGTT 23000
23001 TGAACCAGACGTATAGTTATAGTCCAAACCGATCGAGCCGGTGGTCAGGC 23050
23051 TGATACACGCAGAGAGCGCATCCTGATGTGTCATAGGACCAGCTATTTTC 23100
23101 CGTTCCCATTCAAACCACTCCGCGGCCACCTCGATCTCGCATCGCGCCTT 23150
23151 TATTTCTAACGCCTCACTACGGGGCGCGACAAAAATTGGTTTTCCAGATT 23200
23201 GATGCATCACTAACCAGACTGCCCTGCCTACCGGCAGACCCCATAGCCCG 23250
23251 GTAAAATAATTATGGAAGTCCGGACCAGACAAGACGATTACGTCGACACC 23300
23301 GGATTGCATCATCGCATTCTGCGCGCGTCGCACTCGATGGTGATATTGCT 23350
23351 CTTGTGATGGCGAGTTTAGCTTGGACAGGTCCATTTTTTGAATGCTGAAAC 23400
```

FIG. 1S

```
23401 TACTTCACAGGGAGCGTAGACTGTTTTTGCGTTGGCTGTTGAATGTAGGT 23450
23451 TTGAGATAGGAGTTTGAGCTATTTACACCGTGTAGTAAGCGATACCAAAT 23500
23501 CATGTCCACGTCGAGCCCCTTGATTTTGGTGCGGAATACGTTTCGTTGTC 23550
23551 GGCCATTTTTGACTTAAATGACACTCGCGTCATTCGATGCGTCATGATTA 23600
23601 ATAAATTAGGAGAAAGCTGCATTACTGACCCAGTGCAATGTTTCGAGGAG 23650
23651 CTGTAGTCCGCGATTTCTTTATCGTGTAGACAATCAACCGACTTAAAATT 23700
23701 ATCGTCTGTTTCTGTACTTAATTAAAACTCATTAATTGTTGATTTTGTGA 23750
23751 TGACTGATGGCAGGATATATGCGGTTGTAATTCATTTTTATTGTCTAAAT 23800
23801 TTCTGTATTTGTTTGTTTGTTCGGTTGTAAATTTTTTTGGAAGACCCTAT 23850
23851 CCAAGTTCATCATAGCCAGCTTGAAGGGAAGGGGGCAGCCTGCAAATTGA 23900
23901 CGGGGAATGCTTTTGCTGGCGTAGGGTATCCGAGGCTCTTTTTGAGCTAC 23950
23951 ACATTGAGTCGCGTGTCAGGCGGTTGAGGGAACGTTGCGATAGCCAACGA 24000
24001 GGTCGGTGTCTCCAGCATGAAACGTGGTATACGCTTGTTGGCGATTTCAA 24050
24051 CACCGCGTTTTTACCATGGCGCGCTCGGATCGCAGGACCAGCTGCCGGCG 24100
24101 CCGATCTCCTCCCAAGCCTTGGCAAATTCAGTGCCTCGATCAAACGTGGA 24150
24151 GATCGGGCGTGGCATAGACGGCAAGGGCGAGAAGGCAGAGATTACACAAC 24200
24201 TCATGGCTTGAGTACTTGACCCAAGACCAAGAAGAGGATCGATAGAGTGA 24250
24251 CCATATAAGTCGATATAGCGGCGATTGTCGGATCGACTTGGTCGCGAAGC 24300
24301 GCACTGACCATCTTTCGGCTCAAGGTGCCCCCGGTACCGGTCGAGATGAA 24350
24351 TATCGCCACGATGACCTCATCGAGCGACACATAGAACGCAAACAGCGCTG 24400
24401 ACGTGATCACCGAAAACCGGCGTGACATGACAGCGCAGACCGGAAACTGG 24450
24451 CCCGACGCCATATCGGGCAAAGTACGGTCTAATGAGATCGTAACCGCGCT 24500
24501 GGTCACCTGACTGGTAGTGACGGAAAATCCAGTAGAAAGGCGGGGCTCTT 24550
24551 CTCGTGACGCGGCGCAGGCGCGCGGGGCTAGCATCATATGAATTC      24595
```

OCTOPINE T-DNA PROMOTERS

This is a continuation of application Ser. No. 07/869,216, filed Apr. 13, 1992, now Abandoned, which is a continuation of application Ser. No. 07/440,432 filed Nov. 21, 1989, now Abandoned, which is a continuation of application Ser. No. 06/553,786 filed Nov. 19, 1983, now Abandoned. This application is also a continuation-in-part of application Ser. No. 07/741,034 filed Aug. 6, 1991, now Abandoned, which is a continuation of application Ser. No. 07/144,775 filed Jan. 20, 1988, now U.S. Pat. No. 5,102,796, which is a continuation of application Ser. No. 06/485,614 filed Apr. 15, 1983, now Abandoned. This application is also a continuation-in-part of application Ser. No. 07/713,624 filed Jun. 10, 1991, which is a continuation of application Ser. No. 07/260,574 filed Oct. 21, 1988, now Abandoned, which is a continuation-in-part of application Ser. No. 06/848,733 filed Apr. 4, 1986, now Abandoned, which is a continuation-in-part of application Ser. No. 06/535,354 filed Sep. 26, 1983, now Abandoned. Applicants hereby assert their right to priority through each of these applications.

FIELD

The present invention is in the fields of genetic engineering and plant husbandry, and especially provides means for promotion of transcription in plants.

BACKGROUND

Following are publications which disclose background information related to the present invention. These publications are discussed in greater depth in the Background sections indicated and in Example 1. P. Dhaese et al. (1983) EMBO J. 2:419–426, A. Depicker et al. (1982) J. Mol. Appl. Genet. 1:561–573, H. De-Greve et al. (1982) J. Mol. Appl. Genet. 1:499–511, and F. Heidekamp et al. (1983) Nucl. Acids Res. 11:6211–6223 report the sequences of "transcript 7" (identified as ORF3 of the present invention), nos, ocs (ORF11 herein), and tmr (ORF8 of the present invention), respectively. Publications disclosing RNA or protein products of T-DNA genes are listed in Table 5 (see Genes on the TIP Plasmids). N. Murai et al. (1983) Science 222:476–482, and T. C. Hall et al., EP-A-126546 disclose use of the ocs (ORF11) promoter for expression of a plant structural gene. M. W. Bevan et al. (1983) Nature 304:184–187, R. T. Fraley et al. (1983) Proc. Natl. Acad. Sci. USA 80:4803–4807, and L. Herrera-Estrella et al. (1983) Nature 303:209–213, disclose use of the nos promoter for expression of bacterial structural genes (see Manipulations of the TIP Plasmids).

Shuttle Vectors

Shuttle vectors, developed by G. B. Ruvkun and F. M. Ausubel (1981) Nature 298:85–88, provide a way to insert foreign genetic materials into position of choice in a large plasmid, virus, or genome. There are two main problems encountered when dealing with large plasmids or genomes. Firstly, the large plasmids may have many sites for each restriction enzyme. Unique site-specific cleavage reactions are not reproducible and multi-site cleavage reactions followed by ligation lead to great difficulties due to the scrambling of the many fragments whose order and orientation one does not want changed. Secondly, the transformation efficiency with large DNA plasmids is very low. Shuttle vectors allow one to overcome these difficulties by facilitating the insertion, often in vitro, of the foreign genetic material into a smaller plasmid, then transferring, usually by in vivo techniques, to the larger plasmid.

A shuttle vector consists of a DNA molecule, usually a plasmid, capable of being introduced into the ultimate recipient bacteria. It also includes a copy of the fragment of the recipient genome into which the foreign genetic material is to be inserted and a DNA segment coding for a selectable trait, which is also inserted into the recipient genome fragment. The selectable trait ("marker") is conveniently inserted by transposon mutagenesis or by restriction enzymes and ligases.

The shuttle vector can be introduced into the ultimate recipient cell, typically a bacterium of the family Rhizobiaceae (which contains the genus Agrobacterium), by a tri-parental mating (Ruvkin and Ausubel, supra), direct transfer of a self-mobilizable vector in a bi-parental mating, direct uptake of exogenous DNA by Agrobacterium cells ("transformation", using the conditions of M. Holsters et al. (1978) Molec. Gen. Genet. 163:181–187), by spheroplast fusion of Agrobacterium with another bacterial cell, by uptake of liposome-encapsulated DNA, or infection with a shuttle vector that is based on a virus that is capable of being packaged in vitro. A tri-parental mating, a technique well known to those skilled in the art of manipulation of large plasmids found in members of the family Rhizobiaceae, involves the mating of a strain containing a mobilizable plasmid, which carries genes for plasmid mobilization and conjugative transfer, with the strain containing the shuttle vector. If the shuttle vector is capable of being mobilized by the plasmid genes, the shuttle vector is transferred to the recipient cell containing the large genome, e.g. the Ti or Ri plasmids of Agrobacterium strains.

After the shuttle vector is introduced into the recipient cell, possible events include a double cross over with one recombinational event on either side of the marker. This event will result in transfer of a DNA segment containing the marker to the recipient genome replacing a homologous segment lacking the insert. To select for cells that have lost the original shuttle vector, the shuttle vector must be incapable of replicating in the ultimate host cell or be incompatible with an independently selectable plasmid pre-existing in the recipient cell. One common means of arranging this is to provide in the third parent another plasmid which is incompatible with the shuttle vector and which carries a different drug resistance marker. Therefore, when one selects for resistance to both drugs, the only surviving cells are those in which the marker on the shuttle vector has recombined with the recipient genome. If the shuttle vector carries an extra marker, one can then screen for and discard cells that contain plasmids resulting from a single cross-over event between the shuttle vector and the recipient plasmid resulting in cointegrates in which the entire shuttle vector is integrated with the recipient plasmid. If the foreign genetic material is inserted into or adjacent to the marker that is selected for, it will also be integrated into the recipient plasmid as a result of the same double recombination. It might also be carried along when inserted into the homologous fragment at a spot not within or adjacent to the marker, but the greater the distance separating the foreign genetic material from the marker, the more likely will be a recombinational event occurring between the foreign genetic material and marker, preventing transfer of the foreign genetic material.

If the shuttle vector is used to introduce a phenotypically dominant trait (e.g. a novel expressible insecticide structural gene, but not an inactivated oncogenic T-DNA gene) one need not rely on a double homologous recombination. The cells resulting from a single cross-over event resulting in cointegrate plasmids can transfer the desired trait into plant cells (A. Caplan et al. (1983) Science 222:815–821). One may even use a variant shuttle vector having a single uninterrupted sequence of T-DNA. However, as the resulting T-DNA will now contain a tandem duplication, one must be vigilant regarding a possible rare deletion of the shuttle vector by a single homologous recombination event occurring between the two homologous sequences in either the Agrobacterium or plant cells.

Shuttle vectors have proved useful in manipulation of Agrobacterium plasmids: see D. J. Garfinkel et al. (1981) Cell 27:143–153, A. J. M. Matzke and M.-D. Chilton (1981) J. Molec. Appl. Genet. 1:39–49, and J. Leemans et al. (1981) J. Molec. Appl. Genet. 1:149–164, who referred to shuttle vectors by the term "intermediate vectors" or "iV".

A recently disclosed variation of the shuttle vector system for inserting changes into large DNA molecules is the "suicide vector". In this system, as described by A. Puhler et al., U.S. Pat. No. 4,626,504 and R. Simon et al. (1983) Biotech. 1:784–791, the shuttle vector is incapable of being maintained within the recipient cell. This property eliminates the need to introduce an incompatible plasmid into the recipient cell in order to exclude the shuttle vector as is commonly done during a triparental mating. All vectors which do not integrate into some already present DNA effectively "commit suicide" by not being replicated. As can be done with traditional types of shuttle vectors, one may distinguish between double and single homologous by screening for an antibiotic resistance gene which is not between the two regions of homology. Use of a pBR322-based suicide vector to transfer DNA sequences into a Ti plasmid has been reported by E. Van Haute et al. (1983) EMBO J. 2:411–417, and L. Comai et al. (1982) Plant. Molec. Biol. 1:291–300, and A. Caplan et al., supra. C. H. Shaw et al. (1983) Gene 28:315–330, report use of a suicide vector to introduce a foreign DNA into a Ti plasmid without also introducing a selectable marker by means of selection of a single homologous recombinant followed by selection of a double homologous recombinant.

An alternative to the use of shuttle vectors for introduction of novel DNA sequences into T-DNA by means of homologous recombination involves bacterial transposons. As described in the section Agrobacterium-Genes on the TIP Plasmids, transposons can "jump" into the T-DNA of a TIP plasmid (e.g. see D. J. Garfinkel et al. (1981) Cell 27:143–153). Should the transposon be modified in vitro by the insertion of the novel sequence, that novel DNA can be transferred into the TIP plasmid's T-DNA by the transposon. The TIP can then transfer the novel DNA/transposon/T-DNA combination to a plant cell where it will be stably integrated.

Overview of Agrobacterium

Included within the gram-negative bacterial family Rhizobiaceae in the genus Agrobacterium are the species *A. tumefaciens* and *A. rhizogenes*. These species are respectively the causal agents of crown gall disease and hairy root disease of plants. Crown gall is characterized by the growth of a gall of dedifferentiated tissue. Hairy root is a teratoma characterized by inappropriate induction of roots in infected tissue. In both diseases, the inappropriately growing plant tissue usually produces one or more amino acid derivatives, known as opines, not normally produced by the plant which are catabolized by the infecting bacteria. Known opines have been classified into three main families whose type members are octopine, nopaline, and agropine. The cells of inappropriately growing tissues can be grown in culture, and, under appropriate conditions, be regenerated into whole plants that retain certain transformed phenotypes.

Virulent strains of Agrobacterium harbor large plasmids known as Ti (tumor-inducing) plasmids in *A. tumefaciens* and Ri (root-inducing) plasmids in *A. rhizogenes*. Curing a strain of these plasmids results in a loss of pathogenicity. The Ti plasmid contains a region, referred to as T-DNA (transferred-DNA), which in tumors is found to be integrated into the genome of the host plant. The T-DNA encodes several transcripts. Mutational studies have shown that some of these are involved in induction of tumorous growth. Mutants in the genes for tml, tmr, and tms, respectively result in large tumors (in tobacco), a propensity to generate soots, and a tendency for shoot induction. The T-DNA also encodes the gene for at least one opine synthase, and the Ti plasmids are often classified by the opine which they caused to be synthesized. Each of the T-DNA genes is under control of a T-DNA promoter. The T-DNA promoters resemble eukaryotic promoters in structure, and they appear to function only in the transformed plant cell. The Ti plasmid also carries genes outside the T-DNA region. These genes are involved in functions which include opine catabolism, oncogenicity, agrocin sensitivity, replication, and autotransfer to bacterial cells. The Ri plasmid is organized in a fashion analogous to the Ti plasmid. The set of genes and DNA sequences responsible for transforming the plant cell are hereinafter collectively referred to as the transformation-inducing principle (TIP). The designation TIP therefore includes, but is not limited to, both Ti and Ri plasmids. The integrated segment of a TIP is termed herein "T-DNA" (transferred DNA), whether derived from a Ti plasmid or an Ri plasmid. Octopine-type T-DNA and Ti plasmids are herein sometimes referred to as oT-DNA and oTi plasmids, respectively.

M.-D. Chilton (June 1983) Sci. Amer. 248(6):50–59, has recently provided an introductory article on the use of Ti plasmids as vectors. Recent general reviews of Agrobacterium-caused disease include those by D. J. Merlo (1982), Adv. Plant Pathol. 1:139–178, L. W. Ream and M. P. Gordon (1982), Science 218:854–859, and M. W. Bevan and M.-D. Chilton (1982), Ann. Rev. Genet. 16:357–384; G. Kahl and J. Schell (1982) *Molecular Biology of Plant Tumors*, K. A. Barton and M.-D. Chilton (1983) Meth. Enzymol. 101:527–539, and A. Caplan et al. (1983) Science 222:815–821.

Infection of Plant Tissues

Plant cells can be transformed by Agrobacterium in a number of methods known in the art which include but are not limited to co-cultivation of plant cells in culture with Agrobacterium, direct infection of a plant, fusion of plant protoplasts with Agrobacterium spheroplasts, direct transformation by uptake of free T-DNA by plant cell protoplasts, transformation of protoplasts having partly regenerated cell walls with intact bacteria, transformation of protoplasts by liposomes containing T-DNA, use of a virus to carry in the T-DNA, microinjection, and the like. Any method will suffice as long as the gene is stably transmitted through mitosis and meiosis.

The infection of plant tissue by Agrobacterium is a simple technique well known to those skilled in the art (for an example, see D. N. Butcher et al. (1980) in *Tissue Culture Methods for Plant Pathologists*, eds.: D. S. Ingram and J. P. Helgeson, pp. 203–208). Typically a plant is wounded by any of a number of ways, which include cutting with a razor, puncturing with a needle, or rubbing with abrasive. The wound is then inoculated with a solution containing tumor-inducing bacteria. An alternative to the infection of intact plants is the inoculation of pieces of tissues such as potato tuber disks (D. K. Anand and G. T. Heberlein (1977) Amer. J. Bot. 64:153–158) or segments of tobacco stems (K. A. Barton, et al. (1983) Cell 32:1033–1043). After induction, the tumors can be placed in tissue culture on media lacking phytohormones. Hormone independent growth is typical of transformed plant tissue and is in great contrast to the usual conditions of growth of such tissue in culture (A. C. Braun (1956) Cancer Res. 16:53–56).

Agrobacterium is also capable of infecting isolated cells and cells grown in culture (L. Márton et al. (1979) Nature 277:129–131) and isolated tobacco mesophyll protoplasts. In the latter technique, after allowing time for partial regeneration of new cell walls, Agrobacterium cells were added to the culture for a time and then killed by the addition of antibiotics. Only those cells exposed to *A. tumefaciens* cells harboring the Ti plasmid were capable of forming calli when plated on media lacking hormone. Most calli were found to contain an enzymatic activity involved in opine anabolism. Other workers (R. B. Horsch and R. T. Fraley (18 Jan. 1983) 15th Miami Winter Symposium) have reported transformations by co-cultivation, leading to a high rate (greater than 10%) of calli displaying hormone-independent growth, with 95% of those calli making opines. M. R. Davey et al. (1980) in Ingram and Helgeson, supra, pp. 209–219, describe the infection of older cells that had been regenerated from protoplasts.

Plant protoplasts can be transformed by the direct uptake of TIP plasmids. M. R. Davey et al. (1980) Plant Sci. Lett. 18:307–313, and M. R. Davey et al. (1980) in Ingram and Helgeson, supra, were able to transform Petunia protoplasts with the Ti plasmid in the presence of poly-L-α-ornithine to a phenotype of opine synthesis and hormone-independent growth in culture. It was later shown (J. Draper et al. (1982) Plant and Cell Physiol. 23:451–458, M. R. Davey et al. (1982) in *Plant Tissue Culture 1982*, ed: A. Fujiwara, pp. 515–516) that polyethelene glycol-stimulated Ti plasmid uptake and that some T-DNA sequences were integrated into the genome. F. A. Krens et al. (1982) Nature 296:72–74, reported similar results using polyethelene glycol following by a calcium shock, though their data suggests that the integrated T-DNA included flanking Ti plasmid sequences.

An alternative method to obtain DNA uptake involves the use of liposomes. The preparation of DNA-containing liposomes is taught by Papahadjopoulos in U.S. Pat. Nos. 4,078,052 and 4,235,871. Preparations for the introduction of Ti-DNA via liposomes have been reported (T. Nagata et al. (1982) in Fujiwara, supra, pp. 509–510, and T. Nagata (1981) Mol. Gen. Genet. 184:161–165). An analogous system involves the fusion of plant and bacterial cells after removal of their cell walls. An example of this technique is the transformation of Vinca protoplast by Agrobacterium spheroplasts reported by S. Hasezawa et al. (1981) Mol. Gen. Genet. 182:206 210. Plant protoplasts can take up cell wall delimited Agrobacterium cells (S. Hasezawa et al. (1982) in Fujiwara, supra pp. 517–518).

T-DNA can be transmitted to tissue regenerated from a fusion of two protoplasts, only one of which had been transformed (G. J. Wullems et al. (1980) Theor. Appl. Genet. 56:203–208). As detailed in the section on Regeneration of Plants, T-DNA can pass through meiosis and be transmitted to progeny as a simple Mendelian trait.

Regeneration of Plants

Differentiated plant tissues with normal morphology have been obtained from crown gall tumors. A. C. Braun and H. N. Wood (1976) Proc. Natl. Acad. Sci. USA 73:496–500, grafted tobacco teratomas onto normal plants and were able to obtain normally appearing shoots which could flower. The shoots retained the ability to make opines and to grow independently of phytohormones when placed in culture. In the plants screened, these tumorous phenotypes were not observed to be transmitted to progeny, apparently being lost during meiosis (R. Turgeon et al. (1976) Proc. Natl. Acad. Sci. USA 73:3562–3564). Plants which had spontaneously lost tumorous properties, or which were derived from teratoma seed, were initially shown to have lost all their T-DNA (F.-M. Yang et al. (1980) *In Vitro* 16:87–92, F. Yang et al. (1980) Molec. Gen. Genet. 177:707–714, M. Lemmers et al. (1980) J. Mol. Biol. 144:353–376). However, later work with plants that had become revertants after hormone treatment (1 mg/l kinetin) showed that plants which had gone through meiosis, though losing T-DNA genes responsible for the transformed phenotype, could retain sequences homologous to both ends of T-DNA (F. Yang and R. B. Simpson (1981) Proc. Natl. Acad. Sci. USA 78:4151–4155). G. J. Wullems et al. (1981) Cell 24:719–724, further demonstrated that genes involved in opine anabolism were capable of passing through meiosis though the plants were male sterile and that seemingly unaltered T-DNA could be inherited in a Mendelian fashion (G. Wullems et al. (1982) in Fujiwara, supra). L. Otten et al. (1981) Molec Gen. Genet. 183:209–213, used Tn7 transposon-generated Ti plasmid mutants in the tms (shoot-inducing) locus to create tumors which proliferated shoots. When these shoots were regenerated into plants, they were found to form self-fertile flowers. The resultant seeds germinated into plants which contained T-DNA and made opines. In further experiments, H. DeGreve et al. (1982) Nature 300:752–755, have found that octopine synthase can be inherited as a single dominant Mendelian gene. However, the T-DNA had sustained extensive deletions of functions other than ocs while undergoing regeneration from callus. Similar experiments with a tmr (root-inducing) mutant showed that full-length T-DNA could be transmitted through meiosis to progeny, that in those progeny nopaline genes could be expressed, though at variable levels, and that cotransformed yeast alcohol dehydrogenase I gene was not expressed (K. A. Barton et al. (1983) Cell 32:1033–1043). Other experiments have shown that nopaline T-DNA is maintained during regeneration and that male sterile flowers pass on the T-DNA in a Mendelian fashion (J. Memelink et al. (1983) Mol. Gen. Genet. 190:516–522). It now appears that regenerated tissues which lack T-DNA sequences are probably decended from untransformed cells which "contaminate" the tumor (G. Ooms et al. (1982) Cell 30:589–597). Recent work by A. N. Binns (1983) Planta 158:272–279, indicates that tumorogenic genes, in this case tmr, can be "shut off" during regeneration and "turned back on" by placing regenerated tissue in culture.

Roots resulting from transformation from *A. rhizogenes* have proven relatively easy to regenerate directly into plantlets (M.-D. Chilton et al. (1982) Nature 295:432–434.

Genes on the TIP Plasmids

A number of genes have been identified within the T-DNA of the TIP plasmids. About half a dozen octopine plasmid T-DNA transcripts have been mapped (S. B. Gelvin et al. (1982) Proc. Natl. Acad. Sci. USA 79:76–80, L. Willmitzer et al. (1982) EMBO J. 1:139–146) and some functions have been assigned (J. Leemans et al. (1982) EMBO J. 1:147–152). Some of these regions, specifically those encoding tmr and tms, can also be transcribed in prokaryotic cells (G. Schröder et al. (1983) EMBO J. 2:403–409). The four genes of an octopine-type plasmid that have been well defined by transposon mutagenesis include tms, tmr, tml, and ocs (D. J. Garfinkel et al. (1981) Cell 27:143–153). F. Heidekamp et al. (1983) Nucleic Acids Res. 11:6211–6223, have reported the sequence of tmr from pTiAch5, an octopine-type plasmid. Ti plasmids which carry mutations in these genes respectively incite tumorous calli of *Nicotiana tabacum* which generate shoots, proliferate roots, and are larger than normal. In other hosts, mutants of these genes can induce different phenotypes (see M. W. Bevan and M.-D. Chilton (1982) Ann. Rev. Genet. 16:357–384). The phenotypes of tms and tmr are correlated with differences in the phytohormone levels present in the tumor. The differences in cytokinin:auxin ratios are similar to those which in culture induce shoot or root formation in untransformed callus tissue (D. E. Akiyoshi et al. (1983) Proc. Natl. Acad. Sci. USA 80:407–411 and A. Caplan et al. (1983) Science 222:815–821). T-DNA containing a functional gene for either tms or tmr alone, but not functional tml alone, can promote significant tumor growth. Promotion of shoots and roots is respectively stimulated and inhibited by functional tml (L. W. Ream et al. (1983) Proc. Natl. Acad. Sci. USA 80:1660–1664). Mutations in T-DNA genes do not seem to affect the insertion of T-DNA into the plant genome (Leemans et al. (1982) supra, Ream et al. (1983) supra).

Octopine Ti plasmids comprise the ocs gene which octopine synthase (lysopine dehydrogenase), which has been sequenced by H. De Greve et al. (1982) J. Mol. Appl. Genet. 1:499–511. It does not contain introns (intervening sequences commonly found in eukaryotic genes which are post-transcriptionally spliced out of the messenger precursor during maturation of the mRNA). It does have sequences that resemble a eukaryotic transcriptional signal ("TATA box") and a polyadenylation site. All of the signals necessary for expression of the ocs gene are found within 295 bp of the ocs transcriptional start site (C. Koncz et al. (1983) EMBO J. 2:1597–1603). P. Dhaese et al. (1983) EMBO J. 2:419–426, reported the sequence of "transcript 7" (open reading frame (ORF) 3 of the present invention), and the utilization of various polyadenylation sites by "transcript 7" and ocs. The presence of the enzyme octopine synthase within a tissue can protect that tissue from the toxic effect of various amino acid analogs (G. A. Dahl and J. Tempé (1983) Theor. Appl. Genet. 66:233–239, G. A. Dahl et al., EPO Publication no. A1-0140556.

Nopaline Ti plasmids comprise the nopaline synthase gene (nos), which has been sequenced by A. Depicker et al. (1982) J. Mol. Appl. Genet. 1:561–573. As was found with the ocs gene, nos is not interrupted by introns. It has two polyadenylation sites and a potential "TATA box". In contrast to ocs, nos is preceded by a sequence which may be a transcriptional signal known as a "CAT box". All of the signals necessary for expression of the nos gene are found within 261 bp of the nos transcriptional start site (C. Koncz et al., supra). A gene for agrocinopin synthase and genes equivalent to tms and tmr have been identified on a nopaline-type plasmid (H. Joos et al. (1983) Cell 32:1057–1067), and a number of transcripts have been mapped (L. Willmitzer et al. (1983) Cell 32:1045–1056). J. C. McPhersson et al. (1980) Proc. Natl. Acad. Sci. USA 77:2666–2670, reported the in vitro translation of T-DNA encoded mRNAs from crown gall tissues.

Transcription from hairy root T-DNA has also been detected (L. Willmitzer et al. (1982) Mol. Gen. Genet. 186:16–22). Functionally, the hairy root syndrome appears to be equivalent of a crown gall tumor incited by a Ti plasmid mutated in tmr (F. F. White and E. W. Nester (1980) J. Bacteriol. 144:710–720).

In eukaryotes, methylation (especially of cytosine residues) of DNA is correlated with transcriptional inactivation; genes that are relatively under-methylated are transcribed into mRNA. S. B. Gelvin et al. (1983) Nucleic Acids Res. 11:159–174, have found that the T-DNA in crown gall tumors is always present in at least one unmethylated copy. That the same genome may contain numerous other copies of T-DNA which are methylated suggests that the copies of T-DNA in excess of one may be biologically inert. (See also G. Ooms et al. (1982) Cell 30:589–597.)

The Ti plasmid encodes other genes which are outside of the T-DNA region and are necessary for the infection process. (See M. Holsters et al. (1980) Plasmid 3:212–230 for nopaline plasmids, and H. De Greve et al. (1981) Plasmid 6:235–248, D. J. Garfinkel and E. W. Nester (1980) J. Bacteriol 144:732–743, and G. Ooms (1980) J. Bacteriol. 144:82–91 for octopine plasmids). Most important are the onc genes, which when mutated result in Ti plasmids incapable of oncogenicity. (These loci are also known as vir, for virulence.) Several onc genes have been accurately mapped and have been found to be located in regions conserved among various Ti plasmids (H. J. Klee et al. (1983) J. Bacteriol. 153:878–883, V. N. Iyer et al. (1982) Mol. Gen. Genet. 188:418–424). The onc genes function in trans, being capable of causing the transformation of plant cells with T-DNA of a different plasmid type and physically located on another plasmid (J. Hille et al. (1982) Plasmid 7:107 118, H. J. Klee et al. (1982) J. Bacteriol 150:327–331, A. J. de Framond et al. (1983) Biotechnol. 1:262–269). Nopaline Ti DNA has direct repeats of about 25 base pairs immediately adjacent to the left and right borders of the T-DNA which might be involved in either excision from the Ti plasmid or integration into the host genome (N. S. Yadav et al. (1982) Proc. Natl. Acad. Sci. USA 79:6322–6326), and a homologous sequence has been observed adjacent to an octopine T-DNA border (R. B. Simpson et al. (1982) Cell 29:1005–1014). Opine catabolism is specified by the occ and noc genes, respectively, of octopine- and nopaline-type plasmids. The Ti plasmid also encodes functions necessary for its own reproduction including an origin of replication. Ti plasmid transcripts have been detected in *A. tumefaciens* cells by S. B. Gelvin et al. (1981) Plasmid 6:17–29, who found that T-DNA regions were weakly transcribed along with non-T-DNA sequences. Ti plasmid-determined characteristics have been reviewed by Merlo, supra (see especially Table II), and Ream and Gordon supra.

TIP Plasmid DNA

Different octopine-type Ti plasmids are nearly 100% homologous to each other when examined by DNA hybridization (T. C. Currier and E. W. Nester (1976) J. Bacteriol. 126:157–165) or restriction enzyme analysis (D. Sciaky et al. (1978) Plasmid 1:238–253). Nopaline-type Ti plasmids have as little as 67% homology to each other (Currier and Nester, supra). A survey revealed that different Ri plasmids are very homologous to each other (P. Costantino et al. (1981) Plasmid 5:170–182). N. H. Drummond and M.-D. Chilton (1978) J. Bacteriol. 136:1178–1183, showed that proportionally small sections of octopine- and nopaline-type Ti plasmids were homologous to each other. These homologies were mapped in detail by G. Engler et al. (1981) J. Mol. Biol. 152:183–208. They found that three of the four homologous regions were subdivided into three (overlapping the T-DNA), four (containing some onc genes), and nine (having onc genes) homologous sequences. The uninterrupted homology contains at least one tra gene (for conjugal transfer of the Ti plasmid to other bacterial cells), and genes involved in replication and incompatibility. This uninterrupted region has homology with a Sym plasmid (involved in symbiotic nitrogen fixation) from a species of Rhizobium, a different genus in the family Rhizobiaceae (R. K. Prakash et al. (1982) Plasmid 7:271–280). The order of the four regions is not conserved, though they are all oriented in the same direction. Part of the T-DNA sequence is very highly conserved between nopaline and octopine plasmids (M.-D. Chilton et al. (1978) Nature 275:147–149, A. Depicker et al. (1978) Nature 275:150–153). Ri plasmids have been shown to have extensive homology among themselves, and to both octopine (F. F. White and E. W. Nester (1980) J. Bacteriol. 144:710–720) and nopaline (G. Risuleo et al. (1982) Plasmid 7:45–51) Ti plasmids, primarily in regions encoding onc genes. Ri T-DNA contains extensive though weak homologies to T-DNA from both types of Ti plasmid (L. Willmitzer et al. (1982) Mol. Gen. Genet. 186:16–22). Plant DNA from uninfected *Nicotiana glauca* contains sequences, referred to as cT-DNA (cellular T-DNA), that show homology to a portion of the Ri T-DNA (F. F. White et al. (1983) Nature 301:348–350, L. Spanò et al. (1982) Plant Molec. Biol. 1:291–300). G. A. Huffman et al. (1984) J. Bacteriol. 157:269–276, have mapped the region of cross-hybridization and have shown that Ri plasmid, pRiA4b, is more closely related to a pTiA6 (octopine-type) than pTiT37 (nopaline-type) and that this Ri plasmid appears to carry sequence homologous to tms but not tmr. Their results also suggested that Ri T-DNA may be discontinuous, analogous to the case with octopine T-DNA.

It has been shown that a portion of the Ti (M.-D. Chilton et al. (1977) Cell 11:263–271) or Ri (M.-D. Chilton (1982) Nature 295:432–434, F. F. White et al. (1982) Proc. Natl. Acad. Sci. USA 79:3193–3197, L. Willmitzer (1982) Mol. Gen. Genet. 186:16–22) plasmid is found in the DNA of tumorous plant cells. The transferred DNA is known as T-DNA. T-DNA is integrated into the host DNA (M. F. Thomashow et al. (1980) Proc. Natl. Acad. Sci. USA 77:6448 6452, N. S. Yadav et al. (1980) Nature 287:458–461) at multiple sites (D. Ursic et al. (1983) Mol. Gen. Genet. 190:494–503, J. Memelink et al. (1983) Mol. Gen. Genet. 190:516–522) in the nucleus (M. P. Nuti et al. (1980) Plant Sci. Lett. 18:1–6, L. Willmitzer et al. (1980) Nature 287:359–361, M.-D. Chilton et al. (1980) Proc. Natl. Acad. Sci. USA 77:4060 4064). There are indications that much non-T-DNA Ti plasmid DNA is transferred into the plant cell prior to T-DNA integration (A. Caplan et al. (1983) Science 222:815–821).

M. F. Thomashow et al. (1980) Proc. Natl. Acad. Sci. USA 77:6448–6452, and M. F. Thomashow et al. (1980) Cell 19:729–739, found the T-DNA from octopine-type Ti plasmids to have been integrated in two separate sections, TL-DNA and TR-DNA, left and right T-DNAs respectively. The copy numbers of TR and TL can vary (D. J. Merlo et al. (1980) Molec. Gen. Genet. 177:637–643). A core of T-DNA is highly homologous to nopaline T-DNA (Chilton et al. (1978) supra, and Depicker et al. (1978) supra), is required for tumor maintenance, is found in TL, is generally present in one copy per cell, and codes for the genes tms, tmr, and tml. On the other hand TR can be totally dispensed with (M. De Beuckeleer et al. (1981) Molec. Gen. Genet. 183:283–288, G. Ooms et al. (1982) Cell 30:589–597), though found in a high copy number (Merlo et al. (1980) supra). G. Ooms et al. (1982) Plasmid 7:15–29, hypothesized that TR is involved in T-DNA integration, though they find that when TR is deleted from the Ti plasmid, *A. tumefaciens* does retain some virulence. G. Ooms et al. (1982) Cell 30:589–597, showed that though T-DNA is occasionally deleted after integration in the plant genome, it is generally stable and that tumors containing a mixture of cells that differ in T-DNA organization are the result of multiple transformation events. The ocs is found in TL but can be deleted from the plant genome without loss of phenotypes related to tumorous growth. The left border of integrated TL has been observed to be composed of repeats of T-DNA sequences which are in either direct or inverted orientations (R. B. Simpson et al. (1982) Cell 29:1005–1014). M. Holsters et al. (1983) Mol. Gen. Genet. 190:35–41, have identified the right border of TL. TL's right border has a 25 bp direct repeat of a sequence found at TL's left border and is also homologous with direct repeats found at either end of nopaline T-DNA. TL was found to be integrated in tandem copies separated by a "linker" of about 400 bp originating from both plant and T-DNA sequences.

In contrast to the situation in octopine-type tumors, nopaline T-DNA is integrated into the host genome in one continuous fragment (M. Lemmers et al. (1980) J. Mol. Biol. 144:353–376, P. Zambryski et al. (1980) Science 209:1385–1391). Direct tandem repeats were observed. T-DNA of plants regenerated from teratomas had minor modifications in the border fragments of the inserted DNA (Lemmers et al., supra). Sequence analysis of the junction between the right and left borders revealed a number of direct repeats and one inverted repeat. The latter spanned the junction (Zambryski et al. (1980) supra). The left junction has been shown to vary by at least 70 base pairs while the right junction varies no more than a single nucleotide (P. Zambryski et al. (1982) J. Mol. Appl. Genet. 1:361-370). Left and right borders in junctions of tandem arrays were separated by spacers which could be over 130 bp. The spacers were of unknown origin and contained some T-DNA sequences. T-DNA was found to be integrated into both repeated and low copy number host sequences. H. Joos et al. (1983) Cell 32:1057-1067, have shown that virulence is not eliminated after deletion of either of the usual nopaline T-DNA borders.

Simpson et al. (1982) supra, and Zambryski et al. (1980) supra have suggested that direct repeats in the border regions are involved in integration of T-DNA into plant DNA. That T-DNA having borders from two different Ti plasmids are less specifically integrated than are homologous borders supports this suggestion (G. Ooms et al. (1982) Plant Molec. Biol. 1:265-276).

N. S. Yadav et al. (1982) Proc. Natl. Acad. Sci. USA 79:6322-6326, have found a chi site, which in the bacteriophage λ augments general recombination in the surrounding DNA as far as 10 kilobases away, in a nopaline Ti plasmid just outside the left end of the T-DNA. R. B. Simpson et al. (1982) Cell 29:1005-1014, did not observe a chi sequence in an octopine Ti plasmid in an equivalent position. The significance of the chi in the Ti plasmid is not known.

Manipulations of the TIP Plasmids

As detailed in the section on Shuttle Vectors, technology has been developed for the introduction of altered DNA sequences into desired locations on a TIP plasmid. Transposons can be easily inserted using this technology (D. J. Garfinkel et al. (1981) Cell 27:143-153). J.-P. Hernalsteen et al. (1980) Nature 287:654-656, have shown that a DNA sequence (here a bacterial transposon) inserted into T-DNA in the Ti plasmid is transferred and integrated into the recipient plant's genome. Though insertion of foreign DNA has been done with a number of genes from different sources, to date foreign genes have not usually been expressed under control of their own promoters. Sources of these genes include rabbit β-globin (C. H. Shaw et al. (1983) Gene 23:315-330), alcohol dehydrogenase (Adh) from yeast (K. A. Barton et al. (1983) Cell 32:1033-1043), AdhI (J. Bennetzen, unpublished) and zein from corn, interferon and globin from mammals, and the mammalian virus SV40 (J. Schell, unpublished). However, when the nopaline synthase gene was inserted into octopine T-DNA and transformed into plant tissue, it was found to be fully functional (C. L. Fink (1982) M. S. thesis, University of Wisconsin-Madison). The gene encoding phaseolin, the storage protein found in seeds of the bean *Phaseolus vulgaris* L., has been transferred into and expressed in sunflower tumors. This latter work constitutes the first example of a transferred plant gene being expressed under control of its own promoter in foreign plant tissue. Transcription started and stopped at the correct positions, and introns were posttranscriptionally processed properly (N. Murai et al. (1983) Science 222:476-482, and T. C. Hall et al., EP-A 122 791). M. Holsters et al. (1982) Mol. Gen. Genet. 185:283-289, have shown that a bacterial transposon (Tn7) inserted into T-DNA could be recovered in a fully functional and seemingly unchanged form after integration into a plant genome.

Deletions can be generated in a TIP plasmid by several methods. Shuttle vectors can be used to introduce deletions constructed by standard recombinant DNA techniques (S. N. Cohen and H. W. Boyer, U.S. Pat. No. 4,237,224). Deletions with one predetermined end can be created by the improper excision of transposons (B. P. Koekman et al. (1979) Plasmid 2:347-357, and G. Ooms et al. (1982) Plasmid 7:15-29). J. Hille and R. Schilperoort (1981) Plasmid 6:151-154, have demonstrated that deletions having both ends at predetermined positions can be generated by use of two transposons. The technique can also be used to construct "recombinant DNA" molecules in vivo.

The nopaline synthase gene has been used for insertion of DNA segments coding for drug resistance that can be used to select for transformed plant cells. In plant cells, a bacterial kanamycin resistance gene from Tn5 is not transcribed under control of its own promoter (J. D. Kemp et al. (1983) in *Genetic Engineering: Applications to Agriculture,* (Beltsville Symp. Agric. Res. 7), ed.: L. D. Owens, pp. 215-228; and C. L. Fink (1982) supra). M. W. Bevan et al. (1983) Nature 304:184-187 and R. T. Fraley et al. (1983) Proc. Natl. Acad. Sci. USA 80:4803-4807, have inserted the kanamycin resistance gene (neomycin phosphotransferase II) from Tn5 behind (i.e. under control of) the nopaline promoter. The construction was used to transform plant cells which in culture displayed resistance to kanamycin and its analogs such as G418. J. Schell et al. (18 Jan. 1983) 15th Miami Winter Symp.(see also J. L. Marx (1983) Science 219:830), reported a similar construction, in which the methotrexate resistance gene (dihydrofolate reductase) from Tn7 was placed behind the nopaline synthase promoter. Transformed cells were resistant to methotrexate. Similarly, L. Herrera-Estrella et al. (1983) Nature 303:209-213, have obtained expression in plant cells of enzymatic activity for octopine synthase and chloramphenicol acetyltransferase, an enzyme which in bacteria confers resistance to chloramphenicol, by placing the structural genes for these two enzymes under control of nos promoters.

N. Murai et al. (1983) Science 222:476-482, and T. C. Hall et al., EP-A-126546, report the fusion of the ocs promoter and the 5'-end of the octopine synthase structural gene to the structural gene for the bean seed protein phaseolin. A fusion protein having the amino terminus of octopine synthase and lacking the amino terminus of phaseolin was produced under control of the T-DNA promoter. The introns, which were contributed by the phaseolin sequences, were posttranscriptionally processed properly.

A. J. de Framond et al. (1983) Biotechnol. 1:262-269, has reported on the construction or a "mini-Ti plasmid". In the nopaline T-DNA there is normally only one site cut by the restriction enzyme KpnI. A mutant lacking the site was constructed and a KpnI fragment, containing the entire nopaline T-DNA, was isolated. This fragment together with a kanamycin resistance gene was inserted into pRK290, thereby resulting in a plasmid which could be maintained in *A. tumefaciens* and lacked almost all non-T-DNA Ti sequences. By itself, this plasmid was not able to transform plant cells. However when placed in an *A. tumefaciens* strain containing an octopine Ti plasmid, tumors were induced which synthesized both octopine and nopaline. The mini-Ti plasmids has also been transferred into plant cells when complemented with a Ti plasmid deleted for its own T-DNA. These results indicated that the non-T-

DNA functions acted in trans with T-DNA, that the missing nopaline Ti plasmid functions were complemented by the octopine Ti plasmid, and that the nopaline "mini-Ti" was functional in the transformation of plant cells. A similar pair of complementing plasmids, each containing either octopine T-DNA or onc genes, has been constructed by A. Hoekema et al. (1983) Nature 303:179–180.

Chilton et al. (18 Jan. 1983) 15th Miami Winter Symp., also reported on the construction of a "micro-Ti" plasmid made by resectioning the mini-Ti with SmaI to delete essentially all of T-DNA but the nopaline synthase gene and the left and right borders. The micro-Ti was inserted into a modified pRK290 plasmid that was missing its SmaI site, and was employed in a manner similar to mini-Ti, with comparable results.

SUMMARY OF THE INVENTION

One object of this invention is to provide means for promoting the expression of structural genes within plant cells wherein said genes are foreign to said cells. In pursuance of this goal, other objects are to provide T-DNA-derived promoters and T-DNA-derived polyadenylation sites, which are DNA sequences capable of controlling structural gene transcription and translation within plant cells. Another object is to provide specialized plant tissues and plants having within them proteins encoded by foreign structural genes and, in cases where the protein is an enzyme, having or lacking metabolites or chemicals which respectively are not or are otherwise found in the cells in which the genes are inserted. Other objects and advantages will become evident from the following description.

The invention disclosed herein provides a plant comprising a genetically modified plant cell having a foreign structural gene introduced and expressed therein under control of T-DNA-derived plant expressible transcriptional control sequences (TxCS). Further, the invention provides plant tissue comprising a plant cell whose genome includes T-DNA comprising a foreign structural gene inserted in such orientation and spacing with respect to T-DNA-derived plant expressible TxCS as to be expressible in the plant cell under control of those sequences. Also provided are novel strains of bacteria containing and replicating T-DNA, the T-DNA being modified to contain an inserted foreign structural gene in such orientation and spacing with respect to a T-DNA-derived plant expressible TxCS as to be expressible in a plant cell under control of said TxCS. Additionally, the invention provides novel vectors having the ability to replicate in *E. coli* and comprising T-DNA, and further comprising a foreign structural gene inserted within T-DNA contained within the vector, in such manner as to be expressible in a plant cell under control of a T-DNA TxCS. Furthermore, strains of bacteria harboring said vectors are disclosed.

The experimental work presented herein is believed to be the first disclosure of a complete T-DNA sequence. The availability of this sequence will enable and otherwise facilitate work in the art of plant transformation to express foreign structural genes and to engage in other manipulations of T-DNA and T-DNA-derived sequences. Without the newly disclosed T-DNA sequence, those of ordinary skill in the art would be unable to make use of the newly disclosed promoters and polyadenylation sites contained therein so as to promote transcription in plant cells of foreign structural genes. The disclosed sequence reveals the existence of several previously unknown T-DNA genes and associated transcriptional control sequences, and makes possible construction of recombinant DNA molecules using promoters and polyadenylation sites from T-DNA genes whose sequences were hitherto unavailable to the public.

The present invention comprises foreign structural genes under control of certain T-DNA promoters expressible in plant cells and/or certain T-DNA polyadenylation sites, said promoter/gene/polyadenylation site combination being inserted into a plant cell by any means known to the art. More specifically, in its preferred embodiment the invention disclosed herein further comprises expression in plant cells of foreign structural genes under control of certain T-DNA-derived plant expressible TxCSs, after introduction via T-DNA, that is to say, by inserting the foreign structural gene into T-DNA under control of a T-DNA promoter and/or ahead of a T-DNA polyadenylation site and introducing the T-DNA containing the insert into a plant cell using known means. Once plant cells expressing a foreign structural gene under control of a T-DNA TxCS are obtained, plant tissues and whole plants can be regenerated therefrom using methods and techniques well known in the art. The regenerated plants are then reproduced by conventional means and the introduced genes can be transferred to other strains and cultivars by conventional plant breeding techniques. The invention in principle applies to any introduction of a foreign structural gene into any plant species into which foreign DNA (in the preferred embodiment T-DNA) can be introduced by any means and in which said DNA can remain stably replicated. In general, these taxa presently include, but are not limited to, gymnosperms and dicotyledonous plants, such as sunflower (family Compositeae), tobacco (family Solanaceae), alfalfa, soybeans, and other legumes (family Leguminoseae), cotton (family Malvaceae), and most vegetables.

The invention is useful for genetically modifying plant cells, plant tissues, and whole plants by inserting useful structural genes from other species, organisms, or strains. Such useful structural genes include, but are not limited to, genes conveying phenotypes such as improved tolerance to extremes of heat or cold, improved tolerance to drought or osmotic stress, improved resistance or tolerance to insect (e.g. insecticidal toxins), arachnid, nematode, or epiphyte pests and fungal, bacterial, or vital diseases, the production of enzymes or secondary metabolites not normally found in said tissues or plants, improved nutrition (e.g. storage proteins, lectins, and legume lectins), flavor (e.g. sweet proteins), or processing properties when used for fiber or human or animal food, changed morphological traits or developmental patterns (e.g. leaf hairs which protect the plant from insects, coloring which is aesthetically pleasing, changed plant growth habits, dwarf plants, reduced time needed for the plants to reach maturity, expression of a gene in a tissue or at a time that gene is not usually expressed, and the like), male sterility, improved photosynthetic efficiency (including lowered photo-respiration), improved nitrogen fixation, improved uptake of nutrients, improved tolerance to herbicides, increased crop yield, improved competition with other plants, and improved germplasm identification by the presence of one or more characteristic nucleic acid sequences, proteins, or gene products, or phenotypes however identified (to distinguish a genetically modified plant of the present invention from plants which are not so modified, to facilitate transfer of a linked artificially introduced phenotype by other (e.g. sexual) means to other genotypes or to facilitate identification of plants protected by patents or by plant variety protection certificates), resistance in cell or tissue culture to selective agents (i.e. selectable markers), and the like. The invention is exemplified by introduction and expression of a structural gene for phaseolin, the major seed storage protein of the bean *Phaseolus vulgaris* L., into plant cells. The introduction and expression of the structural gene for phaseolin, for example, can be used to enhance the protein content and nutritional value of forage or other crops. The invention is also exemplified by the introduction and expression of a lectin structural gene, in this case, also obtained from *P. vulgaris,* into plant cells. The introduction and expression of a novel lectin may be used to change the nutritional or symbiotic properties of a plant tissue. The invention is exemplified in yet other embodiments by the introduction and expression of DNA sequences encoding thaumatin, and its precursors prothaumatin, prethaumatin, and preprothaumatin. Mature thaumatin is a heat-labile sweet-tasting protein found naturally in katemfe (*Thaumatococcus daniellii*) which can be used to enhance the flavor of vegetables which are eaten uncooked without significantly increasing the caloric content of the vegetables. The invention is further exemplified by introduction and expression of a structural gene for a crystal protein from *B. thuringiensis* var. *kurstaki* HD-73 into plant cells. The introduction and expression of the structural gene for an insecticidal protein can be used to protect a crop from infestation with insect larvae of species which include, but are not limited to, hornworm (Manduca sp.), pink bollworm (*Pectionophora gossypiella*), European corn borer (*Ostrinia nubilalis*), tobacco budworm (*Heliothis virescens*), and cabbage looper (*Trichoplusia ni*). Applications of insecticidal protein prepared from sporulating *B. thuringiensis* do not control insects such as the pink bollworm in the field because of their particular life cycles and feeding habits. A plant containing in its tissues insecticidal protein will control this recalcitrant type of insect, thus providing advantage over prior insecticidal uses of *B. thuringiensis*. By incorporation of the insecticidal protein into the tissues of a plant, the present invention additionally provides advantages over such prior uses by eliminating instances of nonuniform application and the costs of buying and applying insecticidal preparations to a field. Also, the present invention eliminates the need for careful timing of application of such preparations since small larvae are most sensitive to insecticidal protein and the protein is always present, minimizing crop damage that would otherwise result from preapplication larval foraging. Other uses of the invention, exploiting the properties of other structural genes introduced into various plant species, will be readily apparent to those skilled in the art.

BRIEF DESCRIPTION OF THE DRAWINGS

FIG. 1 discloses the complete nucleotide sequence of the T-DNA region of the octopine Ti plasmid pTi15955. Only one strand of DNA is shown, oriented 5' to 3' with the left and right borders, as defined in FIG. 2, near the beginning and end of the sequence, respectively.

DETAILED DESCRIPTION OF THE INVENTION

Figure 2:
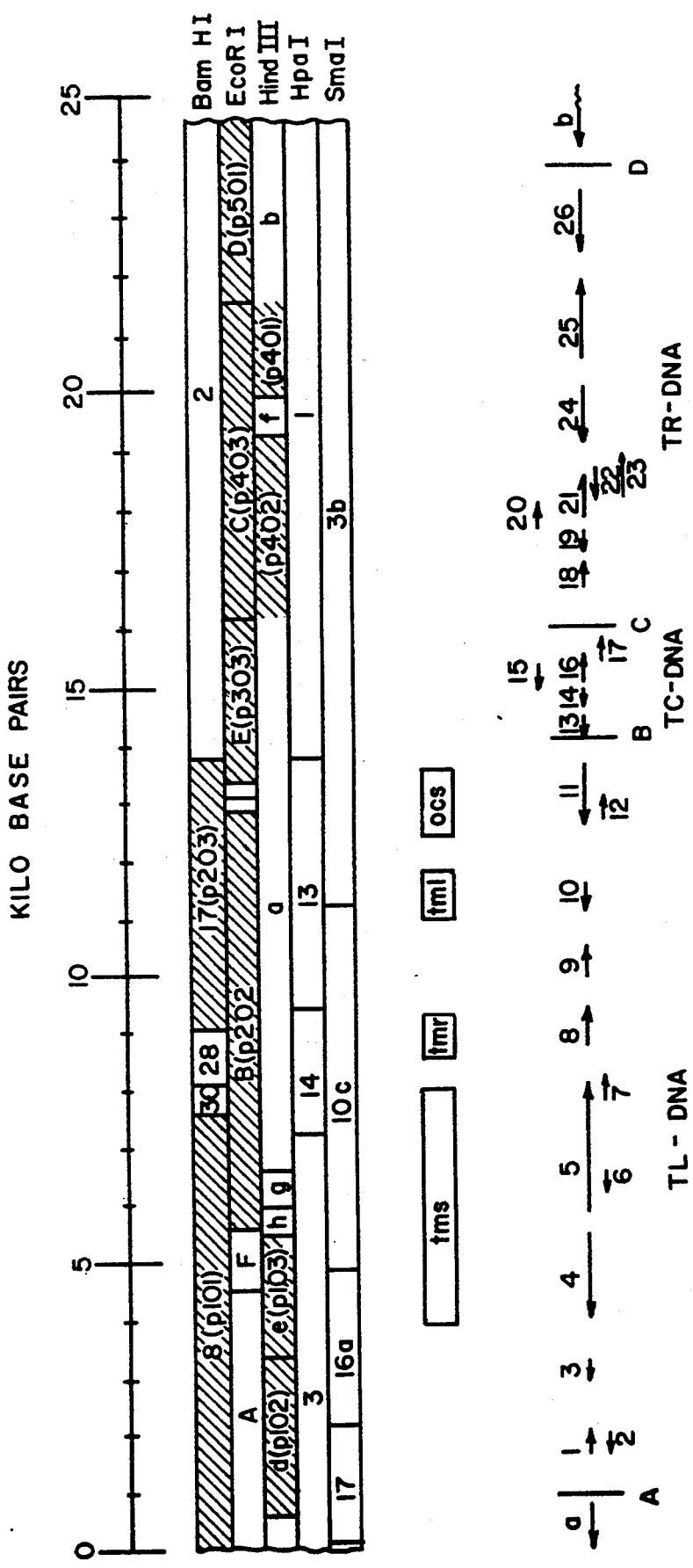
FIG. 2 is a physical map of the region of pTi15955 sequenced. The restriction maps for 5 enzymes are shown and the shaded areas indicate the fragments which were subcloned for sequencing. Known genetic loci are indicated within the boxes. The 24 base border repeats shown at position A, B, C and D divide the T-DNA into TL-DNA, TC-DNA and TR-DNA. The open reading frames within the T-DNA region are numbered from 1 to 26 and the arrows indicate their length and direction of transcription. Open reading frames a and b occur outside the T-DNA region in the flanking Ti plasmid DNA.

The following definitions are provided, in order to remove ambiguities to the intent or scope of their usage in the specification and claims.

TxCS: Transcription controlling sequences refers to a promoter/polyadenylation site combination flanking a particular structural gene or open reading frame (ORF). The promoter and polyadenylation DNA sequences flanking a particular inserted foreign structural gene need not be derived from the same source genes (e.g. pairing two different oT-DNA (octopine-type T-DNA) transcripts) or the same taxonomic source (e.g. pairing sequences from oT-DNA with sequences from non-oT-DNA sources such as other types of T-DNA, plants, animals, fungi, yeasts, and eukaryotic viruses). Therefore the term TxCS refers to either combination of a claimed promoter with an unclaimed polyadenylation site, or combination of a unclaimed promoter with a claimed polyadenylation site, or combination of a promoter and a polyadenylation site which are both claimed. Examples of non-T-DNA plant expressible promoters which can be used in conjunction with a T-DNA polyadenylation site include, but are not limited to, those from genes for phaseolin, the small subunit of ribulose-1,5-bisphosphate carboxylase, and the 19S and 35S transcripts of cauliflower mosaic virus (CaMV).

Promoter: Refers to sequences at the 5'-end of a structural gene involved in initiation of transcription. Expression under control of a T-DNA promoter may take the form of direct expression in which the structural gene normally controlled by the promoter is removed in part or in whole and replaced by the inserted foreign structural gene, a start codon being provided either as a remnant of the T-DNA structural gene or as part of the inserted structural gene, or by fusion protein expression in which part or all of the structural gene is inserted in correct reading frame phase within the existing T-DNA structural gene. In the latter case, the expression product is referred to as a fusion protein. The promoter segment may itself be a composite of segments derived from a plurality of sources, naturally occurring or synthetic. Eukaryotic promoters are commonly recognized by the presence of DNA sequences homologous to the canonical form 5'... TATAA... 3' about 10–30 bp 5' to the location of the 5'-end of the mRNA (cap site). About 30 bp 5' to the TATAA another promoter sequence is often found which is recognized by the presence of DNA sequences homologous to the canonical form 5'... CCAAT... 3'. Translational initiation generally begins at the first 5'... AUG... 3' 3' from the cap site.

Polyadenylation site: Refers to any nucleic acid sequence capable of promoting transcriptional termination. Furthermore, after transcriptional termination polyadenylic acid "tails" will be added to the 3'-end of most mRNA precursors. The polyadenylation site DNA segment may itself be a composite of segments derived from a plurality of sources, naturally occurring or synthetic, and may be from a genomic DNA or an mRNA-derived cDNA. Polyadenylation sites are commonly recognized by the presence of homology to the canonical form 5'... AATAAA... 3', although variation of distance, partial "read-thru", and multiple tandem canonical sequences are not uncommon (C. Montell et al. (1983) Nature 305:600–605).

Foreign structural gene: As used herein includes that portion of a gene comprising a DNA segment coding for a foreign RNA, protein, polypeptide or portion thereof, possibly including a translational start codon, but lacking at least one other functional element of a TxCS that regulates initiation or termination of transcription and inititation of translation, commonly referred to as the promoter region and polyadenylation site. (Note that in the present invention such foreign functional elements may be present after transfer of the foreign structural gene into T-DNA, though such elements may not be functional in a particular embodiment). A foreign structural gene may be a protein not normally found in the plant cell in which the gene is introduced. Additionally, the term refers to copies of a structural gene naturally found within the cell but artificially introduced. A foreign structural gene may encode derived in whole or in part from episomal DNA, plasmid DNA, plastid DNA, genomic DNA, cDNA, viral DNA, viral cDNA, or chemically synthesized DNA. It is further contemplated that a foreign structural gene may contain one or more modifications in either the coding segments or untranslated regions which could affect the biological activity or chemical structure of the expression product, the rate of expression or the manner of expression control. Such modifications include, but are not limited to, mutations, insertions, deletions, and substitutions of one or more nucleotides, and "silent" modifications that do not alter the chemical structure of the expression product but which affect intercellular localization, transport, excretion or stability of the expression product. The structural gene may constitute an uninterrupted coding sequence or it may include one or more introns, bounded by the appropriate plant functional splice junctions, which may be obtained from synthetic or a naturally occurring source. The structural gene may be a composite of segments derived from a plurality of sources, naturally occurring or synthetic, coding for a composite protein, the composite protein being foreign to the cell into which the gene is introduced and expressed or being derived in part from a foreign protein. The foreign structural gene may be a fusion protein, and in particular, may be fused to all or part of a structural gene derived from the same ORF as was the TxCS.

Plant tissue: Includes differentiated and undifferentiated tissues of plants including, but not limited to roots, shoots, pollen, seeds, tumor tissue, such as crown galls, and various forms of aggregations of plant cells in culture, such as embryos and calluses. The plant tissue may be in planta or in organ, tissue, or cell culture.

Plant cell: As used herein includes plant cells in planta and plant cells and protoplasts in culture.

Production of a genetically modified plant expressing a foreign structural gene under control of an oT-DNA-derived TxCS combines the specific teachings of the present disclosure with a variety of techniques and expedients known in the art. In most instances, alternative expedients exist for each stage of the overall process. The choice of expedients depends on variables such as the choice of the basic vector system for the introduction and stable maintenance of the oT-DNA TxCS/structural gene combination, the plant species to be modified and the desired regeneration strategy, and the particular foreign structural gene to be used, all of which present alternative process steps which those of ordinary skill are able to select and use to achieve a desired result. For instance, although the starting point for obtaining oT-DNA TxCSs is exemplified in the present application by oT-DNA isolated from pTi15955 DNA sequences of other homologous octopine-type Ti plasmids might be substituted as long as appropriate modifications are made to the TxCS isolation and manipulation procedures. Additionally, T-DNA genes from other types of T-DNA homologous to the oT-DNA genes having TxCSs disclosed herein may be substituted, again with appropriate modifications of procedures. Homologous genes may be identified by those of ordinary skill in the art by the ability of their nucleic acids to cross-hybridize under conditions of appropriate stringency as is well understood in the art. It will be understood that there may be minor sequence variations within gene sequences utilized or disclosed in the present application. These variations may be determined by standard techniques to enable those of ordinary skill in the art to manipulate and bring into utility the T-DNA promoters and polyadenylation sites of such homologous genes. (Homologs of foreign structural genes may be identified, isolated, sequenced, and manipulated in a manner similar to homologs of the pTi15955 genes of the present invention.) As novel means are developed for the stable insertion of foreign genes in plant cells, those of ordinary skill in the art will be able to select among those alternate process steps to achieve a desired result. The fundamental aspects of the invention are the nature and structure of the foreign structural gene and its means of insertion and expression in a plant genome. The remaining steps of the preferred embodiment for obtaining a genetically modified plant include inserting the oT-DNA TxCS/structural gene combination into T-DNA, transferring the modified T-DNA to a plant cell wherein the modified T-DNA becomes stably integrated as part of the plant cell genome, techniques for in vitro culture and eventual regeneration into whole plants, which may include steps for selecting and detecting transformed plant cells and steps of transferring the introduced gene from the originally transformed strain into commercially acceptable cultivars.

A principal feature of the present invention in its preferred embodiment is the construction of T-DNA having an inserted foreign structural gene under control of a oT-DNA TxCS, i.e., between a promoter and a polyadenylation site, as these terms have been defined, supra, at least one of which is derived from oT-DNA. The structural gene must be inserted in correct position and orientation with respect to the desired oT-DNA promoter. Position has two aspects. The first relates to the side of the promoter on which the structural gene is inserted. It is known that the majority of promoters control initiation of transcription in one direction only along the DNA. The region of DNA lying under promoter control is said to lie "downstream" or alternatively "behind" or "3' to" the promoter. Therefore, to be controlled by the promoter, the correct position of foreign structural gene insertion must be "downstream" from the promoter. (A few known non-T-DNA promoters exert bidirectional control, in which case either side of the promoter could be considered to be "downstream" therefrom.) The second aspect of position refers to the distance, in base pairs, between known functional elements of the promoter, for example the transcription initiation site, and the translational start site of the structural gene. Substantial variation appears to exist with regard to this distance, from promoter to promoter. Therefore, the structural requirements in this regard are best described in functional terms. As a first approximation, reasonable operability can be obtained when the distance between the promoter and the inserted foreign structural gene is similar to the distance between the promoter and the T-DNA gene it normally controls. Orientation refers to the directionality of the structural gene. That portion of a structural gene which ultimately codes for the amino terminus of the foreign protein is termed the 5'-end of the structural gene, while that end which codes for amino acids near the carboxyl end of the protein is termed the 3'-end of the structural gene. Correct orientation of the foreign structural gene is with the 5'-end thereof proximal to the promoter. An additional requirement in the case of constructions leading to fusion protein expression is that the insertion of the foreign structural gene into the oT-DNA promoter-donated structural gene sequence must be such that the coding sequences of the two genes are in the same reading frame phase, a structural requirement which is well understood in the art. An exception to this requirement exists in the case where an intron separates coding sequences derived from a foreign structural gene from the coding sequences of the oT-DNA structural gene. In that case, both structural genes must be provided with compatible splice sites, and the intron splice sites must be so positioned that the correct reading frame for the oT-DNA promoter-donated structural gene and the foreign structural gene are restored in phase after the intron is removed by post-transcriptional processing. Differences in rates of expression or developmental control may be observed when a given foreign structural gene is inserted under control of different oT-DNA TxCSs. Rates of expression may also be greatly influenced by the details of the resultant mRNA's secondary structure, especially stem-loop structures. Different properties, including, but not limited to such properties as stability, intercellular or intracellular localization or excretion, solubility, target specificity, and other functional properties of the expressed protein itself may be observed in the case of fusion proteins depending upon the insertion site, the length and properties of the segment of oT-DNA protein included within the fusion protein and mutual interactions between the components of the fusion protein that effect folded configuration thereof, all of which present numerous opportunities to manipulate and control the functional properties of the foreign protein product, depending upon the desired physiological properties within the plant cell, plant tissue, and whole plant. Similarly to the promoter, the polyadenylation site must be located in correct position and orientation relative to the 3'-end of the coding sequence. Fusion proteins are also possible between the 3'-end of the foreign structural gene protein and a polypeptide encoded by the DNA which serves as a source of the polyadenylation site.

A TxCS is comprised by two major functionalities: a promoter and a polyadenylation site, positioned respectively 5' and 3' to the structural gene. Although in the preferred embodiment these two portions of the TxCS are obtained from the same gene, this is not a requirement of the present invention. These 5' and 3' sequences may be obtained from diverse oT-DNA genes, or one of these sequences may even be obtained from a non-oT-DNA gene. For instance, a promoter may be taken from a oT-DNA gene while the polyadenylation site may come from a plant gene or a cDNA.

In the preferred embodiments a foreign structural gene is nested within an oT-DNA TxCS, suturing the structural gene into the TxCS at NdeI sites and placing the entire TxCS/structural gene combination between a pair of BamHI sites. As will be apparent to those of ordinary skill in the art, the TxCS/gene combination may be placed between any restriction sites convenient for removing the combination from the plasmid it is carried on and convenient for insertion into the plant transformation or shuttle vector of choice. Alternatives to the use of paired NdeI sites (5' ... CATATG ... 3') at the ATG translational start include, but are not limited to, use of ClaI (5' ... (not G)ATCGAT(G) ... 3') or NcoI (5' ... CCATGG ... 3') sites. As will be understood by persons skilled in the art, other sites may be used for the promoter/structural gene suture as long as the sequence at the junction remains compatible with translational and transcriptional functions. An alternative to the suture of the promoter to the foreign structural gene at the ATG translational start is splicing at the transcriptional start or cap site. An advantage of the use of this location is the secondary (stem-loop) structure of the foreign structural gene mRNA will not be disrupted thereby leading to an mRNA having translational activity more nearly resembling the activity observed in the organism which was the source of the gene. The restriction sites at the 5'- and 3'-ends of the structural gene need not be compatible. Use of cut sites cut by two different restriction enzymes at the two TxCS/structural gene junctions will automatically correctly orient the structural gene when it is inserted into the TxCS, though use of an extra restriction enzyme may necessitate removal of an additional set of inconvenient restriction sites within the TxCS and the structural gene. The use of a single restriction enzyme to make a particular structural gene/polyadenylation site suture is not required. Convenient sites within the oT-DNA structural gene and 3' to the translational stop of the foreign structural gene may be used. When these sites have incompatible ends, they may be converted to blunt-ends by methods well known in the art and blunt-end ligated together.

Location of the TxCS/foreign structural gene combination insertion site within T-DNA is not critical as long as the transfer function of sequences immediately surrounding the T-DNA borders are not disrupted, since these regions appear from prior art studies to be essential for insertion of the modified T-DNA into the plant genome. Preferred insertion sites are those which lie in areas that are most actively transcribed, in particular ORF10 (the tml gene and a region including ORF24 (the "1.6 region")). The T-DNA into which the TxCS/structural gene combination is inserted, is obtained from any of the TIP plasmids. The TxCS/structural gene combination is inserted by standard techniques well known to those skilled in the art. The orientation of the inserted plant gene, with respect to the direction of transcription and translation of endogenous T-DNA or vector genes is not critical, either of the two possible orientations is functional. Differences in rates of expression may be observed when a given gene is inserted at different locations within T-DNA, possibly because of such factors as DNA methylation and chromatin structure. Readily detectable levels of expression from the ORF11 (ocs) promoter of the phaseolin structural gene have been obtained where that combination in the form of a fusion protein gene was inserted into pTi15955, an octopine-type plasmid of *A. tumefaciens,* within ocs (ORF11).

A convenient means for inserting a TxCS/foreign structural gene combination into T-DNA involves the use of a shuttle vector, as described in the Background, having segments of T-DNA (those segments between which insertion is desired) incorporated into a plasmid capable of replicating in *E. coli.* The T-DNA segment contains a restriction site, preferably one which is unique within the shuttle vector. The TxCS/structural gene combination can be inserted at the unique site in the T-DNA sequence and the shuttle vector is transferred into cells of the appropriate Agrobacterium strain, preferably one whose T-DNA is homologous with the T-DNA segments of the shuttle vector. The transformed Agrobacterium strain is preferably grown under conditions which permit selection of a double-homologous recombination event which results in replacement of a pre-existing segment of the Ti plasmid with a segment of T-DNA of the shuttle vector. However, it should be noted that the present invention is not limited to the introduction of the TxCS/structural gene combination into T-DNA by a double homologous recombination mechanism; a homologous recombination event with a shuttle vector (perhaps having only a single continuous region of homology with the T-DNA) at a single site or an insertion of a promoter/-gene-carrying bacterial transposon will also prove an effective means for inserting that combination into T-DNA.

Following the strategy just described, the modified T-DNA can be transferred to plant cells by any technique known in the art. For example, this transfer is most conveniently accomplished either by direct infection of plants with the novel Agrobacterium strain containing a foreign structural gene incorporated within T-DNA, or by cocultivation of the Agrobacterium strain with plant cells. The former technique, direct infection, results in due course in the appearance of a tumor mass or crown gall at the site of infection. Crown gall cells can be subsequently grown in culture and, under appropriate circumstances known to those of ordinary skill in the art, regenerated into whole plants that contain the inserted T-DNA segment. Using the method of cocultivation, a certain proportion of the plant cells are transformed, that is to say have T-DNA transferred therein and inserted in the plant cell genome. In either case, the transformed cells must be selected or screened to distinguish them from untransformed cells. Selection is most readily accomplished by providing a selectable marker incorporated into the T-DNA in addition to the TxCS/foreign structural gene. Examples include either dihydrofolate reductase or neomycin phosphotransferase expressed under control of a nopaline synthase promoter. These markers are selected by growth in medium containing methotrexate or kanamycin, respectively, or their analogs. In addition, the T-DNA provides endogenous markers such as the gene or genes controlling hormone-independent growth of Ti-induced tumors in culture, the gene or genes controlling abnormal morphology of Ri-induced tumor roots, and genes that control resistance to toxic compounds such as amino acid analogs, such resistance being provided by an opine synthase (e.g. ocs). Screening methods well known to those skilled in the art include assays for opine production, specific hybridization to characteristic RNA or T-DNA sequences, or immunological assays for specific proteins, including ELISAs (an acronym for "enzyme linked immunosorbant assay"), radioimmune assays and "western" blots. Additionally the phenotype of expressed foreign genes can be used to identify transformed tissue (e.g. insecticidal properties of the crystal protein).

An alternative to the shuttle vector strategy involves the use of plasmids comprising T-DNA or modified T-DNA, into which an TxCS/foreign structural gene is inserted, said plasmids being capable of independent replication in an Agrobacterium strain. Recent evidence reviewed in the Background indicates that the T-DNA of such plasmids can be transferred from an Agrobacterium strain to a plant cell provided the Agrobacterium strain contains certain trans-acting genes whose function is to promote the transfer of T-DNA to a plant cell. Plasmids that contain T-DNA and are able to replicate independently in an Agrobacterium strain are herein termed "sub-TIP" plasmids. A spectrum of variations is possible in which the sub-TIP plasmids differ in the amount of T-DNA they contain. One end of the spectrum retains all of the T-DNA from the TIP plasmid, and is sometimes termed a "mini-TIP" plasmid. At the other end of the spectrum, all but an amount of DNA surrounding the T-DNA borders is deleted, the remaining portions being the minimum necessary for the sub-TIP plasmid to be transferable and integrable in the host cell. Such plasmids are termed "micro-TIP". Sub-TIP plasmids are advantageous in that they are small and relatively easy to manipulate directly, eliminating the need to transfer the gene to T-DNA from a shuttle vector by homologous recombination. After the desired structural gene has been inserted, they can easily be introduced directly into an Agrobacterium cell containing the trans-acting genes that promote T-DNA transfer. Introduction into an Agrobacterium strain is conveniently accomplished either by transformation of the Agrobacterium strain or by conjugal transfer from a donor bacterial cell, the techniques for which are well known to those of ordinary skill. For purposes of introduction of novel DNA sequences into a plant genome, TIP plasmids and sub-TIP plasmids should be considered functionally equivalent.

Although the preferred embodiment of this invention incorporates a T-DNA-based Agrobacterium-mediated system for incorporation of the TxCS/foreign structural gene combination into the genome of the plant which is to be transformed, other means for transferring and incorporating the gene are also included within the scope of this invention. Other means for stable incorporation of the combination into a plant genome additionally include, but are not limited to, use of vectors based upon viral genomes, minichromosomes, transposons, and homologous or nonhomologous recombination into plant chromosomes. Alternate forms of delivery of these vectors into a plant cell additionally include, but are not limited to, direct uptake of nucleic acid, fusion with vector-containing liposomes or bacterial spheroplasts, microinjection, and encapsidation in viral coat protein followed by an infection-like process. Systems based on Agrobacterium cells and TIPs can be used to transform dicots and gymnosperms by transfer of DNA from a bacterium to a plant cell; systems based on alternate vectors or means for vector delivery may be used to transform all gymnosperms and all angiosperms, including both monocots and dicots.

Regeneration of transformed cells and tissues is accomplished by resort to known techniques. An object of the regeneration step is to obtain a whole plant that grows and reproduces normally but which retains integrated T-DNA. The techniques of regeneration vary somewhat according to principles known in the art, depending upon the origin of the T-DNA, the nature of any modifications thereto and the species of the transformed plant. Plant cells transformed by an Ri-type T-DNA are readily regenerated, using techniques well known to those of ordinary skill, without undue experimentation. Plant cells transformed by Ti-type T-DNA can be regenerated, in some instances, by the proper manipulation of hormone levels in culture. Preferably, however, the Ti-transformed tissue is most easily regenerated if the T-DNA has been mutated in one or both of the tmr and tms genes. Inactivation of these genes returns the hormone balance in the transformed tissue towards normal and greatly expands the ease and manipulation of the tissue's hormone levels in culture, leading to a plant that is readily regenerated because of its more normal hormone physiology. It is important to note that if the mutations in tmr and tms are introduced into T-DNA by double homologous recombination with a shuttle vector, the incorporation of the mutation must be selected in a different manner than the incorporation of the TxCS/structural gene combination. For example, in the former instance one might select for tmr and tms inactivation by chloramphenicol resistance while the TxCS/foreign gene selection might be for resistance to kanamycin. The inactivation of the tms and tmr loci may be accomplished by an insertion, deletion, or substitution of one or more nucleotides within the coding regions or promoters of these genes, the mutation being designed to inactivate the promoter or disrupt the structure of the protein. (The construction of suitable mutations has been exemplified by T. C. Hall et al., EP-A-122791 and EP-A-126546.) In some instances, tumor cells are able to regenerate shoots which carry integrated T-DNA and express T-DNA genes, such as nopaline synthase, and which also express an inserted plant structural gene. The shoots can be maintained vegetatively by grafting to rooted plants and can develop fertile flowers. The shoots thus serve as parental plant material for normal progeny plants carrying T-DNA and expressing the foreign structural gene inserted therein.

The genotype of the plant tissue transformed is often chosen for the ease with which its cells can be grown and regenerated in in vitro culture and for susceptibility to the selective agent to be used. Should a cultivar of agronomic interest be unsuitable for these manipulations, a more amenable variety is first transformed. After regeneration, the newly introduced TxCS/foreign structural gene combination is readily transferred to the desired agronomic cultivar by techniques well-known to those skilled in the arts of plant breeding and plant genetics. Sexual crosses of transformed plants with the agronomic cultivars yield initial hybrids. These hybrids can then be back-crossed with plants of the desired genetic background. Progeny are continuously screened and selected for the continued presence of integrated T-DNA or for the new phenotype resulting from expression of the inserted foreign gene. In this manner, after a number of rounds of back-crossing and selection, plants can be produced having a genotype essentially identical to the agronomically desired parents with the addition of the inserted TxCS/foreign structural gene combination.

EXAMPLES

The following Examples utilize many techniques well-known and accessible to those skilled in the arts of molecular biology and manipulation of TIPs and Agrobacterium; such methods are fully described in one or more of the cited references if not described in detail herein. Enzymes are obtained from commercial sources and are used according to the vendor's recommendations or other variations known to the art. Reagents, buffers and culture conditions are also known to those in the art. Reference works containing such standard techniques include the following: R. Wu, ed. (1979) Meth. Enzymol. 68, R. Wu et al., eds. (1983) Meth. Enzymol. 100 and 101, L. Grossman and K. Moldave, eds. (1980) Meth. Enzymol. 65, J. H. Miller (1972) Experiments in Molecular Genetics, R. Davis et al. (1980) *Advanced Bacterial Genetics*, R. F. Schleif and P. C. Wensink (1982) *Practical Methods in Molecular Biology*, and T. Maniatis et al. (1982) *Molecular Cloning*. Additionally, R. F. Lathe et al. (1983) Genet. Engin. 4:1–56, make useful comments on DNA manipulations.

Textual use of the name of a restriction endonuclease in isolation, e.g. "BclI", refers to use of that enzyme in an enzymatic digestion, except in a diagram where it can refer to the site of a sequence susceptible to action of that enzyme, e.g. a restriction site. In the text, restriction sites are indicated by the additional use of the word "site", e.g. "BclI site". The additional use of the word "fragment", e.g. "BclI fragment", indicates a linear double-stranded DNA molecule having ends generated by action of the named enzyme (e.g. a restriction fragment). A phrase such as "BclI/SmaI fragment" indicates that the restriction fragment was generated by the action of two different enzymes, here BclI and SmaI, the two ends resulting from the action of different enzymes. Note that the ends will have the characteristics of being "sticky" (i.e. having a single-stranded protrusion capable of base-pairing with a complementary single-stranded oligonucleotide) or "blunt" and that the sequence of a sticky-end will be determined by the specificity of the enzyme which produces it.

In the tables and in the text that follows, the underlining of a particular nucleotide in a primer or other sequence indicates the nucleotide which differs from the naturally found sequence, being an insertion or substitution of one or more nucleotides. The use of lower case for two adjacent nucleotides brackets one or more nucleotides that have been deleted from the native sequence. Unless otherwise noted, all oligonucleotide primers are phosphorylated at their 5'-ends, are represented 5'-to-3', and are synthesized and used as described in Example 5.

Plasmids, and only plasmids, are prefaced with a "p", e.g., pTi15955 or p8.8, and strains parenthetically indicate a plasmid harbored therein, e.g., *A. tumefaciens* (pTi15955) or *E. coli* HB101 (p8.8). Self-replicating DNA molecules derived from the bacteriophage M13 are prefaced by an "m", e.g. mWB2341, and may be in either single-stranded or double-stranded form. pTi15955 is on deposit as ATCC 15955; other deposited strains are listed in T9.3.

The DNA constructions described in these Examples have been designed to enable any one of the fourteen eukaryotic TxCSs of pTi15955 to be combined with any of four foreign structural genes. Towards that end, the structural genes, the TxCSs, and the TxCS/structural gene combinations have been placed on DNA "cassettes", having the properties that, after initial modifications have been made, any structural gene may be readily inserted into any TxCS without further modification, and any TxCS/structural gene combination may be isolated by a simple procedure applicable to all such combinations. All combinations are thereby equivalent when being inserted into the plant transformation vector of choice. The initial modifications of the TxCSs are all analogous to each other and the initial modifications of the structural genes are also all analogous to each other. These Examples often involve the use of a common strategy for multiple constructions that differ only in items such as choice of restriction enzymes, DNA fragment size, ORFs encoded, plasmids generated or used as starting material, specific numbers and sequences of oligonucleotides used for mutagenesis, sources of plasmids, and enzyme reactions utilized. For the sake of brevity, the DNA manipulations and constructions are described once, the differing items being detailed by reference to a particular column in a particular Table, a particular series of manipulations used in a particular construction occupying horizontal lines within that Table. For example, Column 1 of Table 6, denoted as "T6.1", when instructing use of a particular restriction enzyme, might say " . . . was digested with T6.1 . . . ", and the construction of mLC (T6.4), which encodes ORFs 5, 8, and 9 (T6.3) involves digestion with SmaI (T6.1) followed by isolation of a 6.4 kbp (T6.2) DNA fragment.

Figure 4:
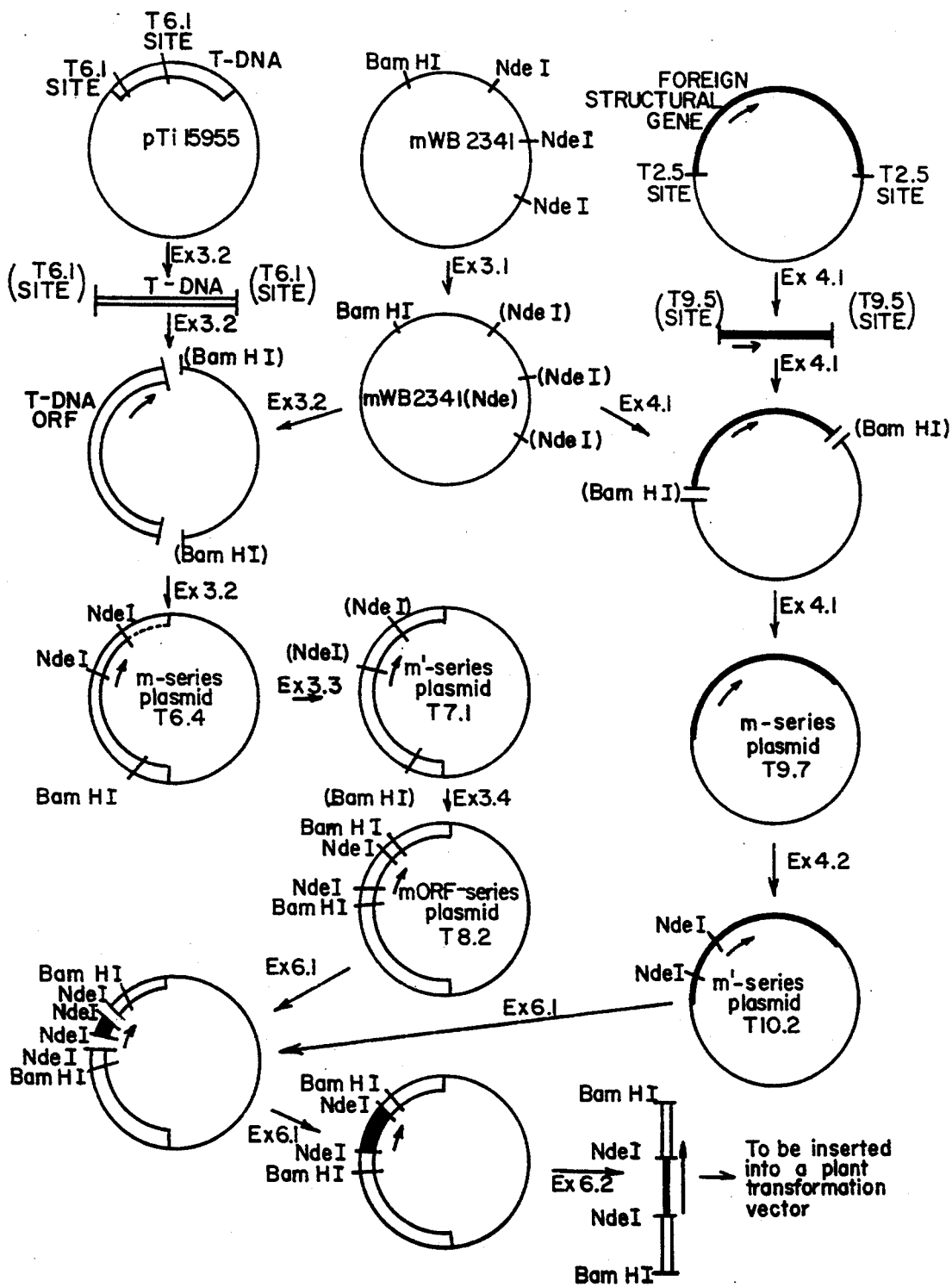
FIG. 4 is a schematic diagram, not drawn to scale, of the DNA manipulation strategy utilized in the Examples. Sites susceptible to the action of a restriction enzyme are indicated by that enzyme's name or place of listing in a Table. A site that is no longer susceptible to the enzyme is indicated by the presence of parentheses around the name of the enzyme. The extent and polarity of an ORF is indicated by arrows as in FIGS. 2 and 3. Names of plasmids, again sometimes designated by place of listing in a Table, are within the circular representations of the plasmids. "Ex" refers to the Example which describes a particular manipulation.

The following is an outline, diagrammed schematically in FIG. 4, of a preferred strategy used to make the exemplified DNA constructions. Endogenous NdeI sites are removed from the M13-based vector mWB2341, resulting in a vector designated mWB2341(Nde) (Example 3.1). Large fragments of T-DNA are introduced into mWB2341(Nde) in a manner that also eliminates the vector's BamHI site (Example 3.2). Endogenous T-DNA NdeI and BamHI sites are then removed (Example 3.3) and novel sites are introduced. NdeI sites are introduced at and near the translational start and stop sites, respectively, so that a foreign structural gene on a NdeI fragment may replace the endogenous ORF structural gene. BamHI sites are introduced approximately 0.3 kbp 5' to and 3' from the transcriptional start and stop signals, respectively, so that the TxCS/structural gene combination eventually constructed may be removed on a BamHI fragment (Example 3.4). The structural genes, which fortuitously have no internal NdeI or BamHI sites, are introduced into mWB2341 (Nde) (Example 4.1) and NdeI sites are introduced at and after the translational start and stop sites (Examples 4.2 and 4.3). The structural genes are removed from their vectors on "DNA cassettes" by digestion with NdeI and are inserted into any desired TxCS which has had its endogenous structural gene removed by NdeI digestion (Example 6.1). The TxCS/foreign structural gene combinations are then removed from their vector by digestion with BamHI and inserted into the plant transformation vectors of choice (Example 6.2). It is recognized that construction strategies utilizing fortuitously located restriction sites might be designed by persons of ordinary skill which might be simpler for some particular TxCS/structural gene combination than the generalized DNA cassette strategy utilized herein; however, DNA cassettes are a better approach when one is trying to achieve flexibility in the choice and matching of many diverse TxCSs and structural genes. One of the exemplified combinations, the ORF19 TxCS with the crystal protein structural gene, is repeated in detail in Example 7, wherein Examples 7.1, 7.2, 7.3, 7.4, 7.5, 7.6, and 7.7 correspond to Examples 3.2, 3.3, 3.4, 4.1, 4.2, 6.1, and 6.2, respectively.

Example 1

This example provides disclosure, analysis, and discussion of the pTi15955 T-DNA sequencing results.

1.1 Summary

The complete nucleotide sequence of the transferred region (T-DNA) of an octopine tumor inducing (Ti) plasmid from *Agrobacterium tumefaciens* (pTi15955) has been determined. A total of 24,595 nucleotides extending approximately 900 bases to either side of the outermost T-DNA boundaries was sequenced. Computer analysis of the sequenced portion of the Ti plasmid revealed that recognition sites for 72 restriction endonucleases were present in the DNA sequence at least once; no site for EcoK exists in this DNA sequence. Two imperfect 24 base repeats were found to border the T-DNA sequence; the left started at position 909 and the right ended at position 23,782, giving the T-DNA region a total length of 22,874 nucleotides. Another two similar 24 base repeats were found within T-DNA and divided it into three distinct domains: T-left (TL-DNA) 13,175 bp (base pairs) of apparently eukaryotic origin; T-center (TC-DNA) 1,816 bp of prokaryotic origin; and T-right (TR-DNA) 7,883 bp of eukaryotic origin. The T-DNA contains nine previously reported transcripts, however, 26 open reading frames (ORF) longer than 300 bases that start with an ATG initiation codon were found. Fourteen ORFs are bounded by eukaryotic promoters, ribosome binding sites, and poly(A) addition sites and occur only in TL- and TR-DNAs. No ORFs showing eukaryotic promoter sequences were located within the TC-DNA.

1.2 DNA sequence and restriction enzyme recognition sites

The nucleotide sequence of a portion of pTi15955 containing the T-DNA region is shown in FIG. 1. Only one strand of the DNA sequence is presented. It is orientated from 5'-to-3' and extends continuously for 24,595 bases, from a BamHI site on the left of Bam fragment 8 to an EcoRI site on the right of Eco fragment D (C. Willmitzer et al. (1983) Cell 32:1045–1056) (FIG. 2). Both strands were sequenced for 90% of the DNA. The remaining 10% was sequenced on one strand but this was often duplicated by sequencing from different restriction enzyme sites. A list of the restriction endonuclease sites determined from the sequence is shown in Table 1. Knowledge of these restriction sites is essential when effecting recombinant DNA manipulations. Of the 73 enzymes searched, only the site for EcoK was not present in the Ti sequence. The site locations of enzymes which digest the DNA more than 30 times are not explicitly given in Table 1 but are inherently present in the sequence disclosed in FIG. 1.

1.3 Extent of the T-region

It has been reported that extended direct repeats of 21-25 bases occur at the borders of the T-DNA (P. Zambryski et al. (1982) J. Molec. Appl. Genet. 1:361-370, N. S. Yadav et al. (1982) Proc. Natl. Acad. Sci. USA 79:6322-6326, R. B. Simpson et al. (1982) Cell 29:1005-1014); these two repeats were located between positions 909-932 and 23,759-23,782 respectively and were marked A and D in FIG. 2. They were direct repeats for 12 bp and extended as 24 bp imperfect repeats as shown in Table 2. Assuming repeats A and D set the outer limits, the total T-region length was 22,874 nucleotides. These repeated sequences were also found at two locations within the T-region of pTi15955, at positions 14,060-14,083 (B) and 15,900-15,923 (C) (FIG. 2 and Table 2).

The presence of four 24 bp border repeats provided clues to the mechanism by which the octopine T-DNA can be integrated into the plant genome either as one continuous 23 kbp (kilobase pairs) segment or as two individual segments; TL-DNA of 13 kbp and TR-DNA of 8 kbp. Integration of TL-DNA was more obvious since it contains tumor inducing genes, which cause the formation of a crown gall in infected plants. TR-DNA, however, lacked these genes and its integration could be detected by the use of opine assays. Nopaline T-DNA contains only two known border repeats at its boundaries, thus it is transferred as a contiguous segment of 22 kbp. Because these border repeats occur in both octopine and nopaline Ti plasmids, they are thought to have a fundamental function in the transfer of the T-region to the plant genome (Zambryski et al. (1982) supra, N. S. Yadav et al., supra, and Simpson et al., supra).

A search for the first 12 bases of the 24 base direct repeat was conducted through the Los Alamos and EMBL data banks, which contain approximately 2,500,000 nucleotides from 2,000 different DNA sources. The repeat was only found at the reported borders of octopine and nopaline T-DNA regions.

1.4 Reading Frame and Transcript Analysis

Within the total T-region, nine transcripts have previously been reported (N. Murai and J. D. Kemp (1982) Nucl. Acids Res. 10:1679-1689, Willmitzer et al. (1983) supra), however, 26 ORFs longer than 300 nucleotides which start with an ATG initiation codon were found (FIG. 2). Transcripts of these ORFs encode polypeptides ranging in size from 11.2 kd to 83.8 kd (see Table 3). Fourteen of these open reading frames showed sequences characteristic of eukaryotic promoters with close homology to the consensus sequences of Goldberg and Hogness (as reviewed by R. Breathnach and P. Chambon (1981) Ann. Rev. Biochem. 50:349-383). They also generally conformed to the typical eukaryotic ribosome binding site postulated by M. Kozak (1981) Nucl. Acids Res. 9:5233-5252, and contained typical polyadenylation sites at their 3'-ends, which in fact act as transcriptional termination signals (M. Fitzgerald and T. Shenk (1981) Cell 24:251-260, P. Dhaese et al. (1983) EMBO J. 2:419-426, C. Montell et al. (1983) Nature 305:600-605) (Table 4). Note that ORF 18 and ORF 19 have an unusual feature in that their polyadenylation sites are situated so that parts of the 3'-untranslated regions of their transcripts, though complementary, are encoded by a common region of the T-DNA sequence.

The TL-DNA region contained eight of the open reading frames having eukaryotic promoters: numbers 1, 3, 4, 5, 8, 9, 10 and 11. All of these corresponded to previously mapped transcripts (C. Willmitzer et al. (1983) supra, H. DeGreve et al. (1983) J. Molec. Appl. Genet. 1:499-511, P. Dhaese et al. (1983) EMBO J. 2:419-426), (see Table 5). Four proteins encoded by the T-DNA region of the octopine Ti plasmid Ach5 are synthesized in E. coli minicells (G. Schröder et al. (1983) EMBO J. 2:403-409). Three of these proteins correspond closely in size to proteins predicted from open reading frames 4, 5 and 8, but no open reading frame exists between frames 5 and 8 which could produce the 28 kd protein reported at this location. The locations of the genes for three proteins expressed in a wheat germ cell-free system (J. C. McPherson et al. (1980) Proc. Natl. Acad. Sci. USA 77:2666-2670) are difficult to assign, as there are many reading frames within the T-DNA fragments which were examined. It is possible that the 30,000 Dalton protein corresponds to reading frame 11 (octopine synthase).

The remaining six ORFs with eukaryotic promoters (numbers 18, 19, 21, 24, 25 and 26 of Table 4) all occurred within the TR-DNA. Only one transcript has been reported in this region and it corresponds to ORF 24, which prior to the present application, has been referred to as the 1.6 kb transcript encoded by the "1.6 region". The function of this transcript is not yet fully known although insertion into the HindIII sites within the transcript apparently causes the loss in production of the opine agropine (Mural and Kemp, supra).

The remaining open reading frames did not contain consensus sequences corresponding to eukaryotic transcription signals. Because of the nucleotide variation occurring within the −10 Pribnow box and −35 regions of prokaryotic promoter sequences, (reviewed by M. Rosenberg and D. Court (1979) Ann. Rev. Genet. 13:319-353) it was difficult to assign such regions to these reading frames. However, ORFs 2, 13, 14 and 16 did show prokaryotic ribosome binding sites similar to the sequence reported by J. Shine and L. Dalgarno (1974) Proc. Natl. Acad. Sci. USA 71:1342-1346. The T-DNA region between repeat sequences B and C contains 5 transcripts (ORFs 13-17), three of which (ORFs 13, 14, and 16) contain Shine and Dalgarno ribosome binding sites and therefore appeared to be prokaryotic in origin. This center section of the T-region is herein referred to as TC-DNA, since it is distinctly different from the flanking TL-DNA and TR-DNA regions. Analysis of our sequence data supports the concept that the TL and TR regions are eukaryotic in nature or origin. Of the 14 eukaryotic open reading frames, 8 occurred within the TL-DNA and 6 within the TR-DNA. In contrast, the TC-DNA which separated these two eukaryotic-like regions contained 3 of the 4 prokaryotic reading frames. Additionally, comparison of the base composition across T-DNA also supported the argument for a prokaryotic origin to the TC-DNA. The high G+C content (56.0%) of the TC-DNA region was close to the reported value of 58.8% for large Ti plasmids (S. Sheikholeslam et al. (1979) Phytopathol. 69:54–58). The G+C contents of TL-DNA and TR-DNA regions were, however, only 44.1% and 44.5%, significantly lower than both the entire Ti plasmid and the TC-DNA region, and much closer to the G+C compositions of higher plant DNA (A. J. Bendich and B. J. McCarthy (1970) Genet. 65:545–565). The base composition of the area adjacent to the T-DNA region containing reading frames (a) and (b) mapped in FIG. 2, was also high at 57.4% and 54.2% as might be expected.

1.5 Codon Usage

All of the transcripts were analyzed individually for codon usage, with an emphasis on codon bias for prokaryotic and eukaryotic transcripts. No bias in codon usage was detected in any of the ORFs within the T-region. There was also no bias between the eukaryotic and prokaryotic transcripts within the T-DNA region. This indicates that genes not having the usual plant gene codon bias will be expressed under control of the T-DNA TxCSs.

1.6 Secondary Structure

Figure 3:
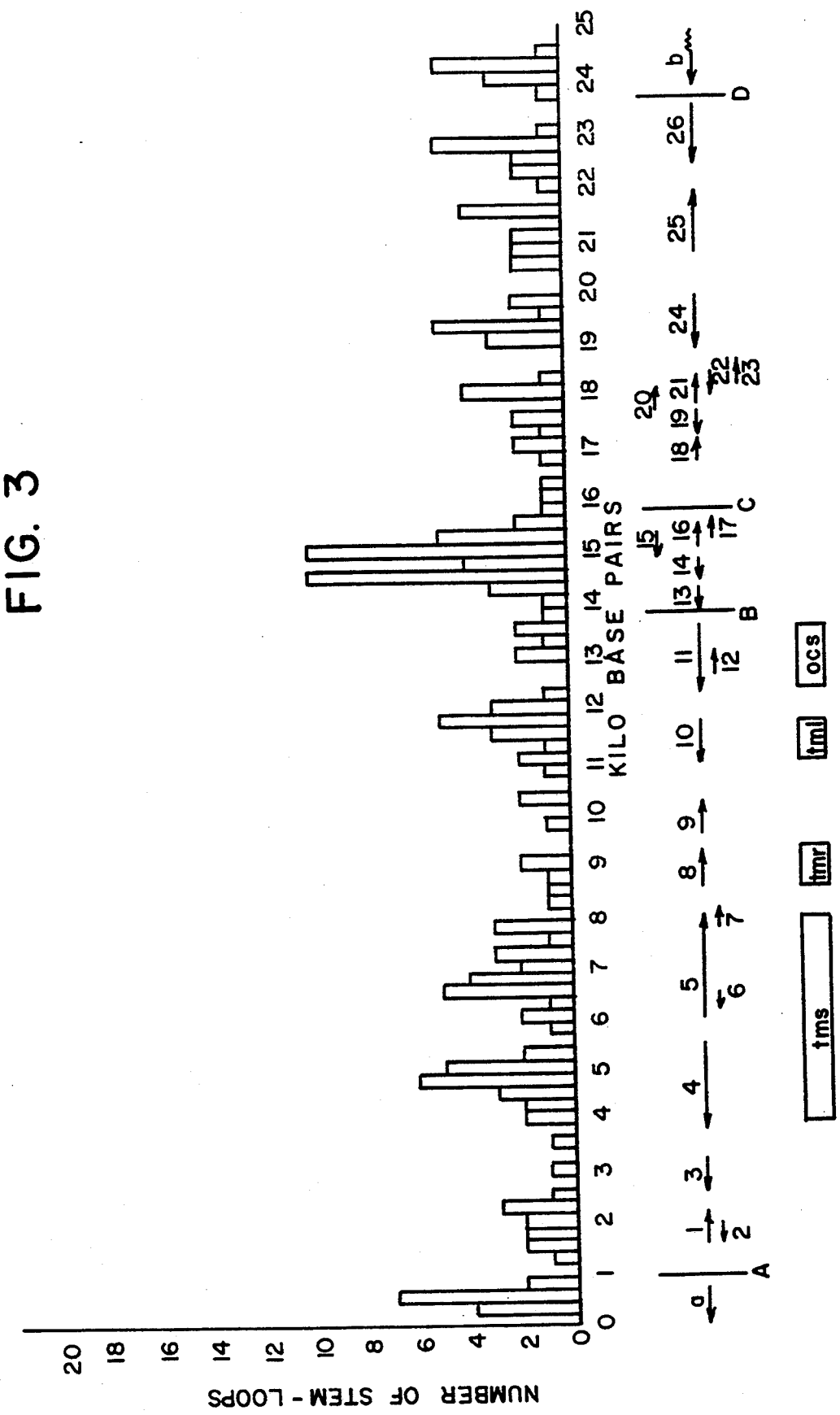
FIG. 3 includes a histogram showing the positions of possible stem-loop structures within the T-DNA. The arrows indicate the transcripts. The 24 base border repeats are at positions A, B, C and D and known genetic loci are indicated within the boxes.

Because inserted repeats might constitute recognition and regulatory sites on DNA (D. M. J. Lilley (1980) Proc. Natl. Acad. Sci. USA 77:6468–6472, N. Panayotatos and R. D. Wells (1981) Nature 289:466–470), the secondary structure of the T-region was analyzed by determining the positions of stem-loops along its length. The stem-loop parameters chosen were a minimum stem length of 10 bases with a bond value of 20, (where $G-T=1$; $A-T=2$ and $G-C=3$), and a maximum loop size of 20 bases. The numbers and positions of the stem-loops are shown in FIG. 3. There was a marked correlation between the number of possible stem-loops and the positions of open reading frames. This indicates that the ORFs disclosed herein are transcribed into authentic mRNAs.

Example 2

This Example discloses the materials and methods used to sequence DNA in general, and the T-DNA of pTi15955 in particular.

2.1 Materials

Ultra pure urea was obtained from BRL (Gaithersburg, Md.), polyacrylamide from BDH (Poole, England), calf intestinal alkaline phosphatase from Boehringer (Mannheim, W. Germany), polynucleotide kinase from P. L. Biochemicals, Inc. (Milwaukee, Wis.), and $[\gamma-^{32}P]$ ATP from New England Nuclear (Boston, Mass.). The restriction enzymes BamHI, BglII, EcoRI, HincII, HindIII, PstI, SalI, SmaI, SstI, SstII, XbaI and XhoI were from Promega Biotec (Madison, Wis.) and AccI, BclI, BglI, BstEII, ClaI, EcoR V, HpaI, KpnI, MboII, MluII, MstII, NcoI, NdeI, NruI, PvuII and RsaI were purchased from New England Biolabs (Beverly, Mass.). All were used essentially according to the suppliers' recommendations. Chemicals used for DNA sequencing reactions were generally from vendors recommended by A. M. Maxam and W. Gilbert (1980) Meth. Enzymol. 65:499–560. X-ray film, X-Omat AR-5, was supplied as long rolls by Kodak (Rochester, N.Y.). All other reagents were of analytical grade unless otherwise stated.

2.2 Methods

The area of the Ti plasmid pTi15955 sequenced is shown in FIG. 2. The shaded areas indicate fragments which were sub-cloned into pBR322 and then propagated in either *E. coli* strain HB101 or GM33. Individual clones were then sequenced using the method of Maxam and Gilbert, supra, essentially as described by them. For sequencing, 10 μg of the cloned DNAs were cut with a suitable restriction enzyme and then treated for 30 minutes at 55° C. with 2.5 units of calf intestinal alkaline phosphatase after adjusting the pH to 8.4 by adding one-tenth volume of 1.0M Tris/HCl to the reaction tube. The alkaline phosphatase was removed by three phenol extractions followed by two ethanol precipitations. The dephosphorylated DNA was then dried and taken up in 15 μl of water and 15 μl of denaturation buffer (20 mM Tris/HCl, pH 9.5, 1 mM spermidine, 0.1 mM EDTA). This mixture was incubated at 70° C. for 5 minutes and then immediately put into iced water. After chilling, 4 μl of kinase buffer (500 mM Tris/HCl, pH 9.5, 100 mM $MgCl_2$, 50 mM dithiothreitol, 50% (v/v) glycerol), 100 μCi of $[\gamma-^{32}P]$ ATP, and 2.0 units of polynucleotide kinase were added and the reaction mixture incubated at 37° C. for 30 minutes. The reaction was stopped by ethanol precipitation and the sample dried under vacuum. The double end-labeled DNA was digested with a suitable restriction enzyme to produce single end-labeled fragments which were then separated on and eluted from a polyacrylamide gel (procedures 4, 5a, 7 and 9 of Maxam and Gilbert, supra). The DNA sequencing reactions were then performed, with the following modifications. The limiting G+A reaction was carried out by adding 30 μl of 88% formic acid to the reaction mix, incubating at 20° C. for 3 minutes, and stopped by the addition of 400 μl of 0.3M sodium acetate (hydrazine stop). The G reaction time was reduced to 20 seconds and incubated at 20° C. The C+T and C reactions were reduced to three minutes at 20° C. and stopped by the addition of 400 μl hydrazine stop. All the reactions were then continued as described by Maxam and Gilbert, supra.

Long sequencing gels 20 cm wide, 110 cm in length and 0.2 mm thick were used to separate the oligonucleotides. The gel plates were treated with a silane as described by H. Caroff and W. Ansorge (1982) Analyt. Biochem. 115:450–457, to bind the acrylamide chemically to one face plate. The other supporting plate was a thermostating plate which maintained the gel at 50° C. throughout electrophoresis. Differential time loadings were avoided by applying each sample simultaneously to 4%, 6% and 16% polyacrylamide gels. Gels were run for 14 hours at 3,000 volts to provide adequate cross-over of the sequencing ladders from gel to gel. After electrophoresis, the gel, still bonded to the face plate, was fixed in 10% acetic acid for 15 minutes, then rinsed in water. The gel dried directly onto the face plate shrinking to a thickness of approximately 0.01 mm. X-ray film was placed in direct contact with the dried gel, resulting in increased band intensity and resolution. Autoradiography was carried out at room temperature without the use of intensifying screens. Using these techniques, 500 bases per fragment were routinely sequenced and by applying 5 fragments to each set of 3 gels, 2,500 bases of sequence could be obtained. Computer analyses of the DNA and protein sequences were performed using computer programs made available by Drs. O. Smithies and F. Blattner (University of Wisconsin, Madison) though other programs available to the art could have been used.

Example 3

This Example teaches the manipulation of oT-DNA TxCSs preparatory to insertion of a foreign structural gene.

3.1 Removal of NdeI sites from an M13-based vector

Single-stranded DNA (ssDNA) of the viral form of the M13-based vector mWB2341 (see Example 5, Barnes et al. (1983) and Barnes and Bevan (1983)) is isolated and subjected to oligonucleotide-directed site-specific mutagenesis, described in detail in Examples 3.3 and 5, after hybridization to 5'CAATAGAAAATT-CATAGGGTTTACC3', 5'CCTGTTTAGTAT-CATAGCGTTATAC3', and 5'CATGTCAAT-CATTTGTACCCCGGTTG3', thereby removing three NdeI sites which will later prove to be inconvenient without changing the translational properties of the encoded proteins. A mutated mWB2341 lacking three NdeI sites is identified and designated mWB2341(Nde).

3.2 Subcloning oT-DNA into an M13-based vector pTi15955 DNA is isolated from *A. tumefaciens* ATCC 15955 and digested to completion with T6.1. 5'-protruding-ends are then converted to blunt-ends by incubation with the Klenow fragment of *E. coli* DNA polymerase I and the appropriate nucleotide triphosphates. The resulting mixture of DNA fragments separated by agarose gel electrophoresis and a T6.2 kbp fragment is eluted from the gel.

Covalently-closed-circular DNA (cccDNA) of the replicative form (RF) of the M13-based vector mWB2341(Nde) is isolated and is digested with EcoRI and HindIII. The resultant sticky-ends are converted to blunt-ends by incubation with the Klenow fragment of DNA polymerase I and the 5'-phosphates are removed by incubation with bacterial alkaline phospharase (BAP). The resulting linearized vector is purified by gel electrophoresis and is mixed with and ligated to the T-DNA fragment isolated above. After transformation of the resulting mixture into *E. coli* WB373, viral DNAs and RFs are isolated from transformants and screened by restriction and hybridization analysis for the presence of inserts which when in single-stranded vital form, are complementary to the sequence as presented in FIG. 1 and which carry the complete DNA sequence of ORFs T6.3. The virus which infects the selected colony is designated T6.4.

3.3 Removal of endogenous NdeI and BamHI sites from oT-DNA

T7.1 is prepared from T7.2 by primer extension after hybridization to the oligonucleotides listed in T7.3. This operation removes indigenous BamHI sites and NdeI sites which may be present which may prove inconvenient in later manipulations. The sites may be removed one at a time by hybridization of a particular oligonucleotide to single-stranded DNA (ssDNA) viral form T6.4, incubation of the primer/viral DNA complex with the Klenow fragment of *E. coli* DNA polymerase I, all four deoxynucleotide triphosphates, and DNA ligase, enrichment of resulting cccDNA molecules, transformation into WB373, selection of transformants, and isolation of RF followed by restriction enzyme analysis to identify a clone missing the undesired restriction sites. These steps are repeated for each site which is to be removed. Alternatively, T6.4 may be simultaneously hybridized to all of the oligonucleotides listed in T7.3 and then carried through the mutagenesis procedure thereby eliminating all of the sites in a single operation.

3.4 Placement of novel NdeI and BamHI sites in oT-DNA

T8.1 is prepared from T8.2 by primer extention after hybridization to the oligonucleotides listed in T8.3 as described above and in Example 5. This has the effect of introducing NdeI sites (5' . . . CATATG . . . 3') at the translational start site (ATG) and near the translational stop site (TAA, TGA, or TAG), and of introducing BamHI sites (5' . . . GGATCC . . . 3') in the sequences flanking the T-DNA gene, approximately 0.3 kbp from the transcriptional start and polyadenylation sites.

Example 4

This Example teaches the manipulation of four exemplary foreign structural genes preparatory for insertion into an oT-DNA TxCS. The genes are for the proteins phaseolin (a nutritionally important seed storage protein from *Phaseolus vulgaris*), *P. vulgaris* lectin (a nutritionally important protein found in seeds and other plant tissues which may be involved in symbiotic nitrogen fixation and making seeds unpalatable to herbivores), thaumatin (a protein which tastes sweet to primates, naturally found in *Thaumatococcus daniellii*), and crystal protein (a protein produced by *Bacillus thuringiensis* which is used commercially to control larval pests of a large number of lepidopteran insect species). The crystal protein structural gene used here, though lacking its 3' end, produces a protein toxic to insect larvae that is equivalent to the naturally occurring activated toxin. Phaseolin, lectin and thaumatin are eukaryotic genes; crystal protein is prokaryotic. Phaseolin contains introns; lectin and crystal protein do not. Though the lectin gene itself contains no introns and could be obtained from a genomic clone, in this Example the lectin structural gene is obtained from a cDNA clone, as is the thaumatin gene.

4.1 Subcloning structural genes into M13

As shown in Table 9 the T9.1 gene is carried by the plasmid T9.2, which may be isolated from T9.3. T9.2 is digested to completion with T9.4 and protruding ends are removed by incubation with T9.5. A T9.6 kbp DNA fragment is isolated by elution from an agarose gel after electrophoretic separation. The resulting fragment is mixed with and ligated to dephosphorylated blunt-ended linearized mWB2341(Nde), prepared as described in Example 3.1, and is transformed into *E. coli* WB373. Viral DNAs and RFs are isolated from transformants and screened by restriction and hybridization analyses for the presence of inserts which are complementary to the sequence when in single-stranded viral form as present in the mRNA. The virus which infects the selected colony is designated T9.7.

4.2 Placement of NdeI sites flanking three structural genes

T10.1 is used to prepare T10.2 by primer extension after hybridization to the oligonucleotides listed in T10.3 as described in Examples 3.3 and 5. This has the effect of introducing NdeI sites at the translational start site and near the translational stop site; there are no BamHI or NdeI sites present within the structural gene which might otherwise be removed. In the case of the *B. thuringiensis* crystal protein gene, a translational stop codon (TAA) is additionally introduced. The 9.1 structural gene may be isolated as a T10.4 kbp DNA fragment after digesting T10.2 to completion with NdeI.

4.3 Mutagenesis of thaumatin

Thaumatin cDNA-containing vectors have been disclosed by C. T. Verrips et al., Eur. Pat. publications 54,330 and 54,331, and L. Edens et al. (1982) Gene 18:1–12. Thaumatin is originally synthesized as preprothaumatin, the prefix "pre" representing the presence of a "signal peptide" having the function of causing the export of thaumatin from the cytoplasm into the endoplasmic reticulum of the cell in which it is being synthesized, and the prefix "pro" representing that the protein is not in mature form. A thaumatin cDNA structural gene is present as the complement to thaumatin mRNA in M13-101-B (Eur. Pat. application 54,331). The viral form of this vector is used as a source of a thaumatin structural gene after site-specific mutagenesis directed by the oligonucleotides listed in Table 11. When mutated by oligonucleotides (a) and (c), which bind to the 5'- and 3'-ends of the structural gene, respectively, a preprothaumatin sequence is extracted from the resultant vector by NdeI digestion. When mutated by oligonucleotides (b) and (d), which bind to the 5'- and 3'-ends, respectively, a mature thaumatin sequence is similarly extracted. Use of the combinations of (a) with (d) and (b) with (c) yields fragments encoding what might be termed prethaumatin and prothaumatin, respectively. All of these sequences are obtained on fragments having a size of approximately 0.7 kbp having no internal NdeI or BamHI sites which may be isolated as usual by gel electrophoresis.

4.4 Other possible manipulations

Phaseolin and lectin, as initially translated have signal peptides at their amino-termini, as was the case with thaumatin. If desired, these signal peptides may be eliminated by placing the 5'-NdeI site between the codons forming the junction between the signal peptide and the mature protein. When under control of a T-DNA in a plant cell nucleus, such a structural gene will cause the synthesis of a phaseolin or lectin protein which is not exported from the cell's cytoplasm. Sequences useful for designing oligonucleotides for the construction of such structural genes for phaseolin and lectin are respectively reported by J. L. Slightom et al. (1983) Proc. Natl. Acad. Sci. USA 80:1897–1901, and L. M. Hoffman et al. (1982) Nucl. Acids Res. 10:7819–7828.

Example 5

This Example describes techniques for the synthesis and use of synthetic oligonucleotides. Other useful references can be found in the list of works cited in the section introductory to these Examples.

5.1 Oligonucleotide synthesis

The techniques for chemical synthesis of DNA fragments used in these Examples utilize a number of techniques well known to those skilled in the art of DNA synthesis. The modification of nucleosides is described by H. Schaller et al. (1963) J. Amer. Chem. Soc. 85:3820, and H. Buchi and H. G. Khorana (1972) J. Mol. Biol. 72:251–288. The preparation of deoxynucleoside phosphoramidites is described by S. L. Beaucage and M. H. Caruthers (1981) Tetrahedron Lett. 22:1859–1862. Preparation of solid phase resin is described by S. P. Adams et al. (1983) J. Amer. Chem. Soc. 105:661–663. Hybridization procedures useful during the formation of double-stranded molecules are described by J. J. Rossi et al. (1982) J. Biol. Chem. 257:9226–9229.

5.2 Oligonucleotide-directed site-specific mutagenesis

General methods of directed mutagenesis have been reviewed recently by D. Shortle et al. (1981) Ann. Rev. Genet. 15:265–294. Of special utility in manipulation of genes is oligonucleotide-directed site-specific mutagenesis, reviewed recently by M. J. Zoller and M. Smith (1983) Meth. Enzymol. 100:468–500 and M. Smith and S. Gillam (1981) in *Genetic Engineering: Principles and Methods*, Vol. 3, eds.: J. K. Setlow and A. Hollaender, and M. Smith (1982) Trends in Biochem. Sciences 7:440–442. This technique permits the change of one or more base pairs in a DNA sequence or the introduction of small insertions or deletions. Recent examples of use of oligonucleotide-directed mutagenesis include M. J. Zoller and M. Smith (1983) supra, M. J. Zoller and M. Smith (1982) Nucleic Acids Res. 10:6487–6500, G. Dalbadie-McFarland et al. (1982) Proc. Natl. Acad. Sci. USA 79:6409–6413, G. F. M. Simons et al. (1982) Nucleic Acids Res. 10:821–832, and C. A. Hutchison III et al. (1978) J. Biol. Chem. 253:6551–6560. Useful M13-based vectors (e.g. mWB2344) have been reported by W. M. Barnes et al. (1983) Meth. Enzymol. 101:98–122, and W. M. Barnes and M. Bevan (1983) Nucleic Acids Res. 11:349–368.

The sequence to be modified usually is moved into a single-stranded bacteriophage vector, here one derived from M13, by standard techniques well known to those in the art. The vector DNA is generally in the double-stranded replicative form (RF), as the single-stranded viral form cannot ordinarily be "cut and spliced" by restriction enzymes and ligases. After in vitro ligation of the fragment into the RF, transformation into a suitable host, and production single-stranded DNA (ssDNA) as part of the life cycle of the vector ssDNA is isolated from phage particles and hybridized to an oligonucleotide having sufficient length and sequence homology to hybridize to the vector in the appropriate location. The oligonucleotide should have the sequence desired as an end product and otherwise differ in no way from the sequence to be changed. It is often advantageous to have the oligonucleotide terminated at both ends by one or more G's or C's in order to "tack down" the ends and to reduce "breathing" of the hybrid's ends. It is also wise to compare the sequence of the oligonucleotide with that of the vector/DNA fragment combination to make sure that the oligonucleotide will hybridize to only one site on the combination. This may readily be checked experimentally by dideoxyribonucleotide sequencing using the nucleotide as a primer; should there be more than one site binding the oligonucleotide, a "shadow" sequence will be observed in addition to the sequence adjoining the target site. Should secondary hybridization sites be observed, a longer oligonucleotide can be synthesized which, under annealing conditions of the proper stringency, will usually have the desired specificity. One must also be aware that if the sequence to be mutagenized forms a stem-loop structure, the oligonucleotide primer may bind poorly or may bind preferentially to another less homologous sequence; this may be overcome by greatly increasing the primer concentration (e.g. 1000-fold). When several distinct oligonucleotides are being used to mutate the vector, they are preferentially all simultaneously hybridized to the vector. Any sites found to not be successfully mutagenized may be changed by a further round of oligonucleotide-directed site-specific mutagenesis. Alternatively, sites may be changed one at a time. Once a hybrid is formed comprising a ssDNA circle base-paired to an oligonucletide carrying a mutant sequence, the oligonucleotide primes synthesis of a complementary strand of DNA by the Klenow fragment of *E. coli* DNA polymerase I, a polymerase lacking a 5'-to-3' exonuclease activity. The vector is optionally incubated with DNA ligase, and the polymerase and ligase reactions may be done simultaneously. Preferentially covalently closed-circular double-stranded DNA (cccDNA) molecules can be selected before transformation by techniques such as alkaline sucrose gradient centrifugation, extraction with phenol under alkaline conditions, or incubation with S1 nuclease. The vector can now be transformed into an appropriate bacterial host cell. Virus particles from this initial infection are isolated and used to form plaques by infecting a lawn of bacteria. In cases where one is changing a restriction site, one may readily screen RFs by restriction enzyme analysis. One may also screen by hybridization under carefully selected conditions using the synthetic mutant oligonucleotide primer as a probe, or by DNA sequencing. When a clone containing the desired change has been isolated, one may manipulate the now mutant DNA as desired using techniques well known to those skilled in the art.

Example 6

This Example teaches use of the oT-DNA TxCSs and the foreign structural genes manipulated in Example 3 and 4, respectively.

6.1 Assembly of TxCS/structural gene combinations

The plasmids listed in T8.1 are digested with NdeI and dephosphorylated with BAP, and the opened vectors may be separated from the T-DNA structural genes found nested within the TxCSs. The plasmids listed in T10.2 are digested with NdeI and the T9.1 structural genes are isolated as a T10.4 kbp fragment by agarose gel electrophoresis followed by elution from the gels. Additionally, thaumatin-encoding fragments are isolated as described in Example 4.3. The opened TxCS vectors and the isolated foreign structural genes may now be mixed with each other pairwise in any desired combination and ligated together. The ligation mixtures are individually transformed into WB373 and RFs are isolated from the resultant transformants and characterized by restriction analysis. A colony is chosen for each transformation which lacks the endogenous T-DNA structural gene and has a single copy of the foreign structural gene inserted within the TxCS, the structural gene and the TxCS being in such orientation with respect to each other that the gene is expressible under control of the TxCS when within a plant cell.

6.2 Assembly of plant transformation vectors

The TxCS/foreign structural gene combinations may be removed from the M13-based vectors constructed in Example 6.1 by digestion with BamHI followed by agarose gel electrophoresis and elution. The TxCS/gene combination may be inserted directly into a 5'GATC . . . 3' sticky-ended site, which may be generated by BamHI, BClI, BglII, MboI, or Sau3AI. Alternatively, the combination may be inserted into any desired restriction site by conversion of sticky-ends into blunt-ends followed by blunt-end ligation or by use of appropriate oligonucleotide linkers.

6.3 Vector choice, transformation and plant regeneration

The plant transformation vector into which the TxCS/gene combination is to be inserted may be a TIP-based system such as a TIP plasmid, a shuttle vector for introduction of novel DNAs into TIP plasmids, or a sub-TIP plasmid, e.g. mini-Ti or micro Ti. Alternatively, a vector based upon a DNA virus, minichromosome, transposon, and homologous or nonhomologous recombination into plant chromosomes may be utilized. Any mode of delivery into the plant cell which is to be initially transformed may be used which is appropriate to the particular plant transformation vector into which the TxCS/gene combination is inserted. These forms of delivery include transfer from an Agrobacterium cell, fusion with vector-containing liposomes or bacterial spheroplasts, direct uptake of nucleic acid, encapsidation in viral coat protein followed by an infection-like process, or microinjection.

The initially transformed plant cells are propagated and used to produce plant tissue and whole plants by any means known to the art which is appropriate for the plant transformation vector and delivery mode being used. Methods appropriate for TIP-based transformation systems include those described by M.-D. Chilton et al. (1982) Nature 295:432–434 for carrots, K. A. Barton et al. (1983) Cell 32:1033–1043 for tobacco, and various other references discussed in the Background, e.g., for sunflower galls. Selection of transformed cells may be done with the drugs and selectable-markers described in the Background (Manipulation of the TIP Plasmids), or with about 10 μg/ml S-(2-aminoethyl)-L-cysteine (AEC) and the ocs gene (G. A. Dahl and J. Tempé (1983) Theor. Appl. Genet. 66:233–239, and G. A. Dahl et al., U.S. application Ser. No. 532,280). The exact drug, concentration, plant tissue, plant species and cultivar must be carefully matched and chosen for ability to regenerate and efficient selection. Screening of transformed tissues for tissues expressing the foreign structural gene may be done by immunological means including micro-ELISA (enzyme-linked immuno-sorbant assay), a technique well known to those skilled in the art of immunochemistry, and "Western" blots of antigens after electrophoresis through SDS-polyacrylamide gels (e.g. as described by R. P. Legocki and D. P. S. Verma (1981) Analyt. Biochem. 111:385–392). Southern, northern (e.g., P. S. Thomas (1980) Proc. Natl. Acad. Sci. USA 77:5201–5205) and dot blots, all methods well-known to those skilled in the art of molecular biology, may be used to detect incorporated DNA and expressed RNA.

Example 7

This Example provides a specific construction, one of many described in Examples 3, 4, and 6. In particular, it describes the insertion of the B. thuringiensis crystal protein structural gene into a BamHI DNA fragment which in a plant cell is transcribed under control of the promoter and polyadenylation site of the oT-DNA ORF19 gene.

7.1 Subcloning oT-DNA into mWB2341(Nde)

pTi15955 DNA is isolated from *A. tumefaciens* ATCC 15955 and digested to completion with SmaI and XbaI. 5'-protruding-ends are then converted to blunt-ends by incubation with the Klenow fragment of *E. coli* DNA polymerase I and the appropriate nucleotide triphosphates. The resulting mixture of DNA fragments separated by agarose gel electrophoresis and a 6.8 kbp fragment is eluted from the gel.

Covalently-closed-circular DNA (cccDNA) of the replicative form (RF) of the M13-based vector mWB2341(Nde) is isolated and is digested with EcoRI and HindIII. The resultant sticky-ends are converted to blunt-ends by incubation with the Klenow fragment of DNA polymerase I and the 5'-phosphates are removed by incubation with bacterial alkaline phosphatase (BAP). The resulting linearized vector is purified by gel electrophoresis and is mixed with and ligated to the T-DNA fragment isolated above. After transformation of the resulting mixture into E. coli WB373, viral DNAs and RFs are isolated from transformants and screened by restriction and hybridization analysis for the presence of inserts which when in single-stranded viral form, are complementary to the sequence as presented in FIG. 1 and which carry the complete DNA sequence of ORFs 11, 18, and 19. The virus which infects the selected colony is designated mRL.

7.2 Removal of an endogenous BamHI site from oT-DNA mRL' is prepared from mRL by primer extension after hybridization to the oligonucleotide CGGTAAAAAGGAGCCCTGAAAGCG. This operation removes an indigenous BamHI site which may prove inconvenient in later manipulations. The site is removed by hybridization of the oligonucleotide to single-stranded DNA (ssDNA) viral form mRL, incubation of the primer/viral DNA complex with the Klenow fragment of E. coli DNA polymerase I, all four deoxynucleotide triphosphates, and DNA ligase, enrichment of resulting cccDNA molecules, transformation into WB373, selection of transformants, and isolation of RF followed by restriction enzyme analysis to identify a clone missing the undesired restriction sites. These steps are repeated for each site which is to be removed.

7.3 Placement of novel NdeI and BamHI sites in oT-DNA mORF19 is prepared from mRL' by primer extention after hybridization to the oligonucleotides CAAATTCCGGATCCCAGCGAAGTTG, CCTACTGACATATGT-TACAAAAATGTTGTCTC, CAGGGTGGT-GTAGCATGCGCACCCCATATGTAAT-TAACTG, and CCATGTTTGCACGGATCCT-GATTTCG as described above and in Example 5. This has the effect of introducing NdeI sites (5' . . . CATATG . . . 3') at the translational start site (ATG) and near the translational stop site (TAA, TGA, or TAG), and of introducing BamHI sites (5' . . . GGATCC . . . 3') in the sequences flanking the T-DNA gene, approximately 0.3 kbp from the transcriptional start and polyadenylation sites.

7.4 Subcloning the crystal protein structural gene into mWB2341(Nde)

The crystal protein gene is carried by the plasmid p123/58-10 which may be isolated from NRRL B-15612. p123/58-10 is digested to completion with HindIII and protruding ends are removed by incubation with the Klenow fragment of E. coli DNA polymerase I. A 6.6 kbp DNA fragment is isolated by elution from an agarose gel after electrophoretic separation. The resulting fragment is mixed with and ligated to dephosphorylated blunt-ended linearized mWB2341(Nde), prepared as described in Example 3.1, and is transformed into E. coli WB373. Viral DNAs and RFs are isolated from transformants and screened by restriction and hybridization analyses for the presence of inserts which are complementary to the sequence when in single-stranded viral form as present in the mRNA. The virus which infects the selected colony is designated mBtCP.

7.5 Placement of NdeI sites flanking the crystal protein structural gene mBtCP is used to prepare mBtCP' by primer extension after hybridization to the oligonucleotides GGAGGTAACATATGGATAACAATCCG and GCGGCAGATTAACGTGTTCATATGCATT-CGAG as described in Examples 7.2 and 5. This has the effect of introducing NdeI sites at the translational start site and near the translational stop site; there are no BamHI or NdeI sites present within the structural gene which might otherwise be removed. A translational stop codon (TAA) is also introduced. The crystal protein structural gene may be isolated as a 2.8 kbp DNA fragment after digesting mBtCP' to completion with NdeI.

7.6 Assembly of ORF19 TxCS/crystal protein structural gene combinations mORF19 is digested with NdeI and dephosphorylated with BAP, and the opened vector may be separated from the T-DNA structural gene found nested within the TxCS. mBtCP' is digested with NdeI and the crystal protein structural gene is isolated as a 2.8 kbp fragment by agarose gel electrophoresis followed by elution from the gel. The opened ORF19 TxCS vector and the isolated crystal protein structural genes may now be mixed with and ligated to each other. The ligation mixture is transformed into WB373 and RFs are isolated from the resultant transformants and characterized by restriction analysis. A colony is chosen which lacks the ORF19 structural gene and has a single copy of the crystal protein structural gene inserted within the ORF19 TxCS, the crystal protein gene and the TxCS being in such orientation with respect to each other that the gene is expressible under control of the TxCS when within a plant cell.

7.7 Assembly of plant transformation vectors

The ORF19 TxCS/crystal protein structural gene combination may be removed from the M13-based vector constructed in Example 7.5 by digestion with BamHI followed by agarose gel electrophoresis and elution. The ORF19 TxCS/crystal protein gene combination may be inserted directly into a 5'GATC . . . 3' sticky-ended site, which may be generated by BamHI, BclI, BglII, MboI, or Sau3AI. Alternatively, the combination may be inserted into any desired restriction site by conversion of sticky-ends into blunt-ends followed by blunt-end ligation or by use of appropriate oligonucleotide linkers. Vector choice, transformation, and plant regeneration are as described in Example 6.3.

TABLE 1

RESTRICTION ENZYME SITES OF THE T-DNA REGION OF pTI 15955

| Enzyme | # Sites | Locations | | | | |
|---|---|---|---|---|---|---|
| Apa I | 1 | 11,930 | | | | |
| Mst II | 1 | 19,471 | | | | |
| Xba I | 1 | 18,089 | | | | |
| Mlu I | 2 | 8,939 | 12,943 | | | |
| Sal I | 2 | 6,778 | 23,292 | | | |
| Tth I | 2 | 17,043 | 24,288 | | | |
| Hpa I | 3 | 7,257 | 9,442 | 13,800 | | |
| Kpn I | 3 | 625 | 9,838 | 24,337 | | |
| Pst I | 3 | 9,211 | 10,069 | 22,456 | | |
| Sst I | 3 | 2,610 | 14,089 | 18,472 | | |
| Sst II | 3 | 14,996 | 18,462 | 23,123 | | |
| Xho I | 3 | 6,727 | 15,208 | 21,476 | | |
| Xma III | 3 | 411 | 11,983 | 22,663 | | |
| Aat II | 4 | 4,511 | 11,763 | 14,665 | 15,140 | |
| Bal I | 4 | 4,319 | 5,456 | 6,253 | 21,618 | |
| BstE II | 4 | 11,768 | 11,976 | 22,865 | 24,501 | |
| Eco B | 4 | 12,452 | 17,041 | 20,160 | 21,516 | |
| Rru I | 4 | 16,515 | 17,144 | 18,885 | 24,213 | |
| Sma I | 4 | 155 | 2,212 | 4,850 | 11,207 | |
| Stu I | 4 | 4,217 | 6,938 | 14,675 | 21,673 | |
| Xor II | 4 | 327 | 670 | 1,206 | 23,033 | |
| Bam HI | 5 | 1 | 7,602 | 8,082 | 9,062 | 13,774 |

TABLE 1-continued
RESTRICTION ENZYME SITES OF THE T-DNA REGION OF pTI 15955

| Enzyme | # Sites | Locations | | | | |
|---|---|---|---|---|---|---|
| Nar I | 5 | 13,536 | 17,158 | 19,170 | 20,027 | 24,098 |
| Bcl I | 6 | 10,058 | 14,711 | 14,973 | 15,938 | 21,540 |
|  |  | 24,404 | | | | |
| Bgl II | 6 | 1,617 | 4,254 | 5,033 | 6,023 | 7,720 |
|  |  | 22,930 | | | | |
| Nru I | 6 | 14,276 | 14,475 | 16,420 | 17,973 | 21,416 |
|  |  | 24,294 | | | | |
| Sph I | 6 | 3,241 | 13,220 | 13,289 | 17,601 | 19,295 |
|  |  | 21,562 | | | | |
| BssH II | 7 | 677 | 9,410 | 12,071 | 19,334 | 22,273 |
|  |  | 23,321 | 24,069 | | | |
| Hind III | 7 | 602 | 3,390 | 5,512 | 5,933 | 6,631 |
|  |  | 19,239 | 19,953 | | | |
| Bgl I | 8 | 158 | 848 | 3,506 | 4,216 | 5,066 |
|  |  | 5,342 | 12,150 | 19,056 | | |
| Eco RI | 8 | 4,494 | 5,545 | 12,823 | 13,026 | 13,362 |
|  |  | 16,202 | 21,631 | 24,590 | | |
| Nae I | 8 | 511 | 5,197 | 6,276 | 10,475 | 12,077 |
|  |  | 20,806 | 22,353 | 24,096 | | |
| Nde I | 8 | 2,174 | 7,282 | 7,475 | 8,360 | 19,084 |
|  |  | 19,715 | 21,731 | 24,586 | | |
| Aha III | 9 | 752 | 2,679 | 2,726 | 2,799 | 3,799 |
|  |  | 9,665 | 12,221 | 13,685 | 16,306 | |
| BstX I | 9 | 587 | 1,589 | 5,862 | 6,150 | 8,002 |
|  |  | 10,259 | 13,751 | 20,132 | 22,741 | |
| Eco RV | 9 | 2,707 | 4,888 | 7,354 | 9,292 | 12,797 |
|  |  | 12,996 | 18,027 | 21,522 | 22,041 | |
| Nco I | 9 | 2,921 | 5,286 | 13,378 | 15,421 | 15,562 |
|  |  | 18,372 | 21,080 | 21,710 | 24,065 | |
| Xmn I | 9 | 2,806 | 5,793 | 6,567 | 6,839 | 6,992 |
|  |  | 10,103 | 13,512 | 17,679 | 21,343 | |
| Mst I | 10 | 1,408 | 4,462 | 9,855 | 11,632 | 15,017 |
|  |  | 15,077 | 15,570 | 17,602 | 19,928 | 20,494 |
| Bvu I | 11 | 2,610 | 5,022 | 6,969 | 11,930 | 12,574 |
|  |  | 14,089 | 16,049 | 18,472 | 22,310 | 23,517 |
|  |  | 24,547 | | | | |
| Ava I | 12 | 153 | 2,210 | 4,848 | 5,114 | 6,019 |
|  |  | 6,727 | 11,205 | 11,960 | 15,208 | 18,678 |
|  |  | 21,476 | 21,803 | | | |
| Cla I | 12 | 1,206 | 2,915 | 4,154 | 9,282 | 9,292 |
|  |  | 14,686 | 15,672 | 18,744 | 18,890 | 20,128 |
|  |  | 21,432 | 24,239 | | | |
| Pvu II | 12 | 2,834 | 3,061 | 4,682 | 5,138 | 6,031 |
|  |  | 6,831 | 9,975 | 11,834 | 12,541 | 14,615 |
|  |  | 22,616 | 24,091 | | | |
| Acc I | 14 | 1,161 | 2,687 | 6,587 | 6,779 | 6,794 |
|  |  | 11,482 | 11,560 | 13,991 | 15,116 | 19,942 |
|  |  | 23,293 | 23,417 | 23,677 | 24,028 | |
| HgiA I | 14 | 812 | 1,868 | 2,610 | 5,134 | 6,228 |
|  |  | 7,628 | 12,480 | 12,734 | 14,089 | 14,583 |
|  |  | 18,183 | 18,472 | 20,866 | 21,093 | |
| Hinc II | 14 | 1,369 | 5,721 | 6,780 | 7,257 | 9,442 |
|  |  | 11,321 | 13,156 | 13,800 | 17,075 | 19,393 |
|  |  | 21,472 | 21,727 | 22,440 | 23,294 | |
| HgiC I | 17 | 621 | 3,586 | 4,960 | 5,119 | 6,153 |
|  |  | 7,443 | 9,834 | 12,010 | 13,535 | 16,015 |
|  |  | 17,157 | 19,169 | 20,026 | 22,701 | 24,097 |
|  |  | 24,324 | 24,333 | | | |
| HgiD I | 21 | 1,376 | 2,503 | 4,508 | 6,803 | 8,335 |
|  |  | 11,760 | 12,516 | 13,536 | 14,662 | 15,137 |
|  |  | 15,231 | 15,801 | 16,470 | 17,158 | 19,170 |
|  |  | 19,389 | 19,648 | 20,027 | 20,244 | 24,098 |
|  |  | 24,455 | | | | |
| BstN I | 24 | 309 | 377 | 1,423 | 2,538 | 4,210 |
|  |  | 5,023 | 6,976 | 7,056 | 7,583 | 10,151 |
|  |  | 10,865 | 11,868 | 12,146 | 12,602 | 13,553 |
|  |  | 14,672 | 16,947 | 19,313 | 19,346 | 19,422 |
|  |  | 19,590 | 19,677 | 20,790 | 22,830 | |
| Hae II | 28 | 539 | 2,206 | 2,331 | 3,327 | 5,196 |
|  |  | 5,210 | 5,309 | 5,981 | 6,539 | 9,789 |
|  |  | 10,474 | 12,269 | 13,539 | 13,845 | 14,335 |
|  |  | 14,707 | 15,731 | 15,872 | 16,412 | 17,161 |
|  |  | 17,980 | 18,509 | 19,173 | 19,576 | 20,030 |
|  |  | 22,352 | 24,101 | 24,398 | | |
| Hph I | 37 | | | | | |
| Ava II | 38 | | | | | |
| Fok I | 39 | | | | | |
| Nci I | 40 | | | | | |
| Rsa I | 40 | | | | | |
| Tth I | 44 | | | | | |
| Hga I | 45 | | | | | |
| Hinf I | 47 | | | | | |
| SfaN I | 47 | | | | | |
| Mbo II | 61 | | | | | |
| ScrF I | 64 | | | | | |
| Dde I | 66 | | | | | |
| Tac I | 67 | | | | | |
| Sau 96 | 69 | | | | | |
| Hae III | 91 | | | | | |
| Hha I | 98 | | | | | |
| Alu I | 99 | | | | | |
| Hpa II | 102 | | | | | |
| Fnu 4H | 103 | | | | | |
| Taq I | 111 | | | | | |
| Sau | 116 | | | | | |
| Mnl I | 158 | | | | | |

TABLE 2
24 BASE BORDER REPEATS FROM pTi15955 (A-D) AND THE NOPALINE Ti PLASMID T37

| | |
|---|---|
| A | G G C A G G A T A T A T T C A A T T G T A A A T |
| B | G G C A G G A T A T A T A C C G T T G T A A T T |
| C | G G C A G G A T A T A T C G A G G T G T A A A A |
| D | G G C A G G A T A T A T G C G G T T G T A A T T |
| Nopaline T37, Left | G G C A G G A T A T A T T G T G G T G T A A A C |
| Nopaline T37, Right | G A C A G G A T A T A T T G G C G G G T A A A C |

TABLE 3
T-DNA ORFs

| Open Reading Frame | Base Position In-itiator (ATG) | Base Position Ter-minator (END) | Ter-mination Codon | No. of Nucleotides in Coding Sequence | Mol Wt. of Translation Product |
|---|---|---|---|---|---|
| 1* | 1,661 | 2,179 | TGA | 519 | 19,832 |
| 2 | 2,113 | 1,736 | TAG | 378 | 14,300 |
| 3* | 3,287 | 2,907 | TAA | 381 | 14,351 |
| 4* | 5,463 | 4,060 | TAA | 1,404 | 49,812 |
| 5* | 5,809 | 8,076 | TAG | 2,268 | 83,868 |
| 6 | 6,579 | 6,259 | TGA | 321 | 12,120 |
| 7 | 7,778 | 8,113 | TAA | 336 | 12,842 |
| 8* | 8,771 | 9,493 | TAG | 723 | 27,007 |
| 9* | 9,996 | 10,571 | TAG | 576 | 21,468 |
| 10* | 11,678 | 11,175 | TGA | 504 | 19,417 |
| 11* | 13,632 | 12,556 | TGA | 1,077 | 38,801 |
| 12 | 12,634 | 13,062 | TGA | 429 | 16,474 |
| 13 | 14,523 | 14,149 | TGA | 375 | 13,819 |
| 14 | 14,882 | 14,568 | TGA | 315 | 11,570 |
| 15 | 15,331 | 14,888 | TAA | 444 | 16,845 |
| 16 | 15,010 | 15,468 | TAG | 459 | 16,927 |
| 17 | 15,422 | 15,883 | TAG | 462 | 16,856 |
| 18* | 16,698 | 17,111 | TAA | 414 | 15,624 |
| 19* | 17,611 | 17,312 | TAA | 300 | 11,420 |
| 20 | 17,644 | 17,952 | TAA | 309 | 11,811 |
| 21* | 17,850 | 18,545 | TAA | 696 | 25,660 |
| 22 | 18,417 | 18,004 | TAA | 414 | 16,108 |
| 23 | 18,382 | 18,690 | TAA | 309 | 11,262 |

TABLE 3-continued

T-DNA ORFs

| Open Reading Frame | Base Position Initiator ↓ (ATG) | Base Position Terminator ↓ (END) | Termination Codon | No. of Nucleotides in Coding Sequence | Mol Wt. of Translation Product |
|---|---|---|---|---|---|
| 24* | 20,128 | 19,148 | TGA | 981 | 35,083 |
| 25* | 20,612 | 21,904 | TGA | 1,293 | 46,756 |
| 26* | 23,384 | 22,479 | TGA | 906 | 33,789 |

*Associated eukaryotic transcriptional control sequences are listed in Table 4.

TABLE 4

EUKARYOTIC PROMOTER SEQUENCES, POLYADENYLATION SITES AND RIBOSOME BINDING SITES

| Open Reading Frame (ORF) | Possible Promoter Sequences (CCAAT) | Possible Promoter Sequences (TATAA) | Distances From ATG Codons | Polyadenylation Sites (AATAAA) | Distance From Stop Codon | Ribosome Binding Sites A GXX | Ribosome Binding Sites ATG | Ribosome Binding Sites G |
|---|---|---|---|---|---|---|---|---|
| 1 | CCAAT | TATAA | −79, −48 | AAAATAA | +330 | GAT | ATG | T |
| 3 | — | TATATA | —, −48 | AATAAA | +119 | ATC | ATG | A |
| 4 | CCAAT | TATAT | −78, −46 | AATAAAA | +148 | GAG | ATG | G |
| 5 | CCATT | TAAATA | −100, −57 | AATTAAAAAA | +151 | ACA | ATG | T |
| 8 | CAAT | TAATA | −74, −43 | AAAAATAAA | +205 | CTT | ATG | G |
| 9 | — | TAATA | —, −66 | ATAAAA | +62 | ACG | ATG | G |
| 10 | CCAAT | TATAA | −91, −61 | AAATAAA | +214 | GCG | ATG | A |
| 11 | — | TATTTAAA | —, −58 | AATAAT | +175 | CAA | ATG | G |
| 18 | CAATT | TATAA | −83, −50 | TAATAATAA | +131 | GCA | ATG | A |
| 19 | — | ATAAAT | —, −34 | AAATAAA | +123 | TAA | ATG | G |
| 21 | — | TATAA | —, −44 | AAAAATTA | +214 | GAA | ATG | G |
| 24 | CCATT | TATTATA | −116, −75 | AAATAAA | +244 | TCG | ATG | G |
| 25 | — | TATAA | —, −95 | AAATAAA | +99 | AAA | ATG | C |
| 26 | — | TAAATA | —, −91 | AATAAA | +358 | AAA | ATG | G |

TABLE 5

PREVIOUSLY KNOWN PROPERTIES OF T-DNA TRANSCRIPTS

| Open Reading Frame | Genetic Loci | (Ref) | Transcript | (Ref) | Previously Determined Mol. Wts. | (Ref) |
|---|---|---|---|---|---|---|
| 1 | — | — | 5 | (5) | — | — |
| 3 | — | — | 7 | (5) | 14,129 | (2) |
| 4 | tms | (3) | 2 | (5) | 49,000 | (6) |
| 5 | tms | (3) | 1 | (5) | 74,000 | (6) |
| 8 | tmr | (3) | 4 | (5) | 27,000 | (6) |
| 9 | — | — | 6a | (5) | — | — |
| 10 | tml | (3) | 6b | (5) | — | — |
| 11 | ocs | (4) | 3 | (5) | 48,000 | (1) |
| 24 | — | — | 1.6 kbp RNA | (4) | — | — |

Refs.:
(1) H. De Greve et al. (1983) J. Molec. Appl. Genet. 1:497-511.
(2) P. Dhaese et al. (1983) EMBO J. 2:419-426.
(3) D. J. Garfinkel et al. (1981) Cell 27:143-153.
(4) N. Murai & J. D. Kemp (1982) Nucl. Acids Res. 10:1679-1689.
(5) L. Willmitzer et al. (1983) Cell 32:1045-1056.
(6) G. Schröder et al. (1983) EMBO J. 2:403-409.

TABLE 6

| T6.1 | T6.2 | T6.3 | T6.4 |
|---|---|---|---|
| BamHI | 7.5 | 1, 3, and 4 | mLL |
| SmaI | 6.4 | 5, 8, and 9 | mLC |
| EcoRI | 7.2 | 5, 8, 9, and 10 | mLR |
| SmaI and XbaI | 6.8 | 11, 18, and 19 | mRL |
| Tth111I | 7.2 | 19, 21, 24, 25, and 26 | mRR |

TABLE 7

| T7.1 | T7.2 | T7.3 | | Approx. Position |
|---|---|---|---|---|
| mLL' | mLL | 5' CCAAATTTCTCACAGATGAAGATCG | 3' | 2,174 |
|  |  | CTGTGAGCCAGCGGAGATGCCATGTTC |  | 7,282 |
|  |  | CGGTTGATAACAGCCAGATGACAGGATCG |  | 7,475 |
| mLC' | mLC | CTATGAGTCGCAGGAGCCGAATGG |  | 7,602 |
|  |  | CTAGAAATTAGTCTATGGAGCCTGTTAC |  | 8,082 |
|  |  | CTTGAGGGAGGAGCCACCTCGTTGC |  | 9,062 |
|  |  | CTGTGAGCCAGCGCAGATGCCATGTTC |  | 7,282 |
|  |  | CGGTTGATAACAGCCAGATGACAGGATCG |  | 7,475 |
|  |  | CGTTGTTAAAAAATTGCAATCAGATGTGCC |  | 8,360 |
| mLR' | mLF | CTATGAGTCGCAGGAGCCGAATGG |  | 7,602 |
|  |  | CTAGAAATTAGTCTATGGAGCCTGTTAC |  | 8,082 |
|  |  | CTTGAGGGAGGAGCCACCTCGTTGC |  | 9,062 |
|  |  | CTGTGAGCCAGCGCAGATGCCATGTTC |  | 7,282 |
|  |  | CGGTTGATAACAGCCAGATGACAGGATCG |  | 7,475 |
|  |  | CGTTGTTAAAAAATTGCAATCAGATGTGCC |  | 8,360 |
| mRL' | mRL | CGGTAAAAAGGAGCCCTGAAAGCG |  | 13,774 |
| mRR' | mRR | CTCAAACCGCCCCAGATGCAGGAGCGG |  | 19,084 |
|  |  | CGCACTGTGACCAGATGAGGCGAGCGG |  | 19,715 |
|  |  | CGGGCCGTTGACAGATGCCCCGGTTTCG |  | 21,731 |

TABLE 8

| T8.1 | T8.2 | T8.3 | Approx. Position |
|---|---|---|---|
| mORF1 | mLL' | 5' CGACAAATTAGGATCCGTCGTATTTATAGG 3' | 1,092 |
|  |  | CAGTCACTATTCCATATGTATGACGG | 1,661 |
|  |  | CCAAATTTCTCACACATATGAAGATCG | 2,174 |
|  |  | CAAGTCAGGTATTATAGGATCCAAGCAAAAAC | 2,764 |
| mORF3 | mLL' | CAAGATATGTGGATCCACGTAAGG | 2,397 |
|  |  | CATAAATTGATCATATGGCTAGCTTAGCTC | 2,900 |
|  |  | CTGCGAAATTCAtaTGTGAGGTGTG | 3,287 |
|  |  | CCGGCAAAATATCGgaTCCAATGGC | 4,088 |
| mORF4 | mLL' | CAGATTTCAAATTTGTAAAGGATCCTGGACGGC | 3,672 |
|  |  | CGGAATCCATATGGCTTCTTCCAATGC | 4,094 |
|  |  | CGAGGTAATGGCCATATGTCTCTGAGTTGGAAATTTC | 5,463 |
|  |  | CCAAAAGGTGGATCCGACAATGGTCG | 5,870 |
| mORF5 | mLC' | CCGGCGTTTCCATGGGGATCCATTTTTTTGGCGC | 5,292 |
|  |  | CTTTTCTAACATATGTCAGCTTCACC | 5,809 |
|  |  | CTAGAAATTAGTCATATGGATCCTG | 8,078 |
|  |  | CCTTTTGGGATCCGGTAAAGCCAGTTGC | 8,655 |
| mORF8 | mLR' | CTAGAAATTAGTCTATGGATCCTGTTAC | 8,082 |
|  | or | CTGCAAAAAACATATGGACCTGATC | 8,771 |
|  | mLC' | CGACGGATTCGAAGGTCATATGTTCGGAATG | 9,477 |
|  |  | CGATGGATCCAATGAGCATGGCTGCGC | 10,003 |
| mORF9 | mLR' | GGGATCCCTCAGGAGTATTTCATCC | 9,389 |
|  | or | CTTGAAACATATGGATCGAATGAGCATGGC | 9,996 |
|  | mLC' | CTAGTTCATATGGGGCGGGATTTCG | 10,574 |
|  |  | CGTTCTAAATGACATTGGATCCATGCAAAATAAC | 10,982 |
| mORF10 | mLR' | CTTGTGGGATCCTGGTGATATTAAAGAGAG | 10,777 |
|  |  | CGTCCATCTCATATGTCGTCATCTTCTCC | 11,170 |
|  |  | CCAATTAGCTACCGTCATATGCAGTGTTGG | 11,678 |
|  |  | CCGGCGGTAAGAATCCGAGCTACAC | 12,446 |
| mORF11 | mRL' | CGCAAAATTCGCCCTGGATCCCGCCC | 11,874 |
|  |  | CAAACTCCATATGAGAGCCCTGACTATGGC | 12,666 |
|  |  | CCACTTTAGCCATATGGTAGATTGC | 13,632 |
|  |  | CAAACTATTCGGGATCCTAACTTTTGGTGTG | 14,032 |
| mORF18 | mRL' | CTCTTAAGAGAGGATCCAGTAATTGAGAATTCG | 16,187 |
|  |  | CATCGAGCATATGAGTTATTATTGG | 16,698 |
|  |  | CCCGTAACACGCATATGACAAAATCAGAGCTAGG | 17,118 |
|  |  | CTGATAATGTCCAGGATCCTCCCC | 17,525 |
| mORF19 | mRL' | CAAATTCCGGATCCCAGCGAAGTTG | 16,815 |
|  |  | CCTACTGACATATGTTACAAAAATGTTGTCTC | 17,308 |
|  |  | CAGGGTGGTGTAGCATGCGCACCCCATATGTAATTAACTG | 17,611 |
|  |  | CCATGTTTGCACGGATCCTGATTTCG | 18,073 |
| mORF21 | mRR' | CTGATAATGGATCCTCCCCTCCATC | 17,525 |
|  |  | CCTCAACTGGAAACCCAGCATATGGAGTATAATCGTCC | 17,850 |
|  |  | CGAAAGGCAATCATAtgCAAAATATTGTGTTGAAAATG | 18,564 |
|  |  | CAGGAGCGGATCCTTCATTGTTTG | 19,101 |
| mORF24 | mRR' | CGCGTTTGGATCCGCCTTTCCTCCG | 18,447 |
|  |  | CAGGGGCTTCGCATATGAGGGCGCCGACG | 19,162 |
|  |  | CAGCATCTCCATATGATTTGGTGTATCGAG | 20,128 |
|  |  | CTCAATATAAACAAAGACGGATCCACAAGAAAAAACC | 20,532 |
| mORF25 | mRR' | CAAGGCTATGGATCCATTTCTGAAAAGGCG | 20,218 |
|  |  | CTTCCACACGTGCATATGCCAATTTCTCAGACCTACC | 20,612 |
|  |  | CCCCAAGAATGAGGTGCATATGCATG | 21,878 |
|  |  | CCGCATGGATCCTCACGTGCCATCAC | 22,466 |
| mORF26 | mRR' | CCTGATGAGAGGATCCAACCCGAGG | 21,795 |
|  |  | CCAGTGCAGCCGCATATGGACCTCACGTGCC | 22,462 |
|  |  | CTTGGACAGGTCCATATGTTTGAATGCTGAAACTAC | 23,384 |
|  |  | CTGATGGCAGGATCCATGCGGTTGTAATTC | 23,767 |

TABLE 9

| T9.1 | T9.2 | T9.3 | T9.4 | T9.5 | T9.6 | T9.7 |
|---|---|---|---|---|---|---|
| phaseolin | p8.8 | NRRL B-15393 | BamHI and BglII | Klenow fragment of E. coli DNA polymerase I | 3.8 | mPhas |
| lectin | pPVL134 | ATCC 39181 | PstI | Bacteriophage T4 DNA polymerase | 0.95 | mLec |
| crystal protein | p123/58-10 | NRRL B-15612 | HindIII | Klenow fragment of E. coli DNA polymerase I | 6.6 | mBtCP |

TABLE 10

| T10.1 | T10.2 | T10.3 | T10.4 |
|---|---|---|---|
| mPhas | mPhas' | 5' CTACTCTACATATGATGAGAGCAAGGG 3' | 2.1 |
|  |  | GTAGGTGTAAGAGCTCATATGGAGAGCATGG |  |
| mLec | mLec' | GCATGAATGCATATGATCATGGCTTCCTCC | 0.8 |
|  |  | CCTGCTAATAATGTTCATATGTCACAC |  |
| mBtCP | mBtCP' | GGAGGTAACATATGGATAACAATCCG | 2.8 |

TABLE 10-continued

| T10.1 | T10.2 | T10.3 | T10.4 |
|---|---|---|---|
| | | GCGGCAGAT<u>T</u>AACGTGTTCATA<u>T</u>GCATTCGAG | |

TABLE 11

| | | |
|---|---|---|
| (a) | 5' GGCATCATACATCA<u>TATG</u>GCCGCCACC | 3' |
| (b) | CCTCACGCTCTCCCGCGC<u>ATATGG</u>CCACCTTCGAGATCGTCAACCGC | |
| (c) | CGAGTAAGAGGATGAAGACGGACA<u>TAT</u>GAGGATACGC | |
| (d) | GGGTCACTTTCTGCCCTACTGCC<u>T</u>AAC<u>ATA</u>TCAAGACGACTAAGAGG | |

What is claimed is:

1. A DNA vector comprising a promoter, a non-T-DNA structural gene, and a polyadenylation site, wherein:
   (a) said promoter, said structural gene, and said polyadenylation site are in such position and orientation with respect to each other that said structural gene is expressible in a transformable dicot plant cell under control of said promoter and said polyadenylation site; and
   (b) said promoter having been obtained from a gene of an octopine-type T-DNA of a Ti plasmid, said gene being selected from the group consisting of Open Reading Frames 1, 4, 5, 9, 10, 18, 19, 21, 24, 25, and 26.

2. The DNA vector of claim 1 wherein said octopine-type T-DNA gene is Open Reading Frame 1.

3. The DNA vector of claim 1 wherein said octopine-type T-DNA gene is Open Reading Frame 4.

4. The DNA vector of claim 1 wherein said octopine-type T-DNA gene is Open Reading Frame 5.

5. The DNA vector of claim 1 wherein said octopine-type T-DNA gene is Open Reading Frame 9.

6. The DNA vector of claim 1 wherein said octopine-type T-DNA gene is Open Reading Frame 10.

7. The DNA vector of claim 1 wherein said octopine-type T-DNA gene is Open Reading Frame 18.

8. The DNA vector of claim 1 wherein said octopine-type T-DNA gene is Open Reading Frame 19.

9. The DNA vector of claim 1 wherein said octopine-type T-DNA gene is Open Reading Frame 21.

10. The DNA vector of claim 1 wherein said octopine-type T-DNA gene is Open Reading Frame 24.

11. The DNA vector of claim 1 wherein said octopine-type T-DNA gene is Open Reading Frame 25.

12. The DNA vector of claim 1 wherein said octopine-type T-DNA gene is Open Reading Frame 26.

13. The DNA vector of claim 1 wherein said structural gene encodes Phaseolin protein.

14. The DNA of claim 1 wherein said structural gene encodes a *Phaseolus vulgaris* lectin.

15. The DNA vector of claim 1 wherein said structural gene encodes a protein selected from the group consisting of thaumatin, prothaumatin, prethaumatin and preprothaumatin.

16. A bacterial strain comprising the DNA vector of claim 1.

17. A transformable dicot plant cell comprising a non-T-DNA, foreign structural gene flanked by a promoter and a polyadenylation site, wherein:
   (a) said promoter, said foreign structural gene, and said polyadenylation site are in such position and orientation with respect to each other that said foreign structural gene is expressible in said dicot plant cell under the control of said promoter and said polyadenylation site; and
   (b) said promoter having been obtained from a gene of an octopine-type T-DNA of a Ti plasmid, said gene being selected from the group consisting of Open Reading Frames 1, 4, 5, 9, 10, 18, 19, 21, 24, 25, and 26.

18. The plant cell of claim 17 wherein said structural gene is endogenous to said plant cell.

19. The plant cell of claim 17 wherein said structural gene is exogenous to said plant cell.

20. The plant cell of claim 17 wherein said foreign structural gene encodes phaseolin protein.

21. The plant cell of claim 17 wherein said foreign structural gene encodes a *Phaseolus vulgaris* lectin.

* * * * *

UNITED STATES PATENT AND TRADEMARK OFFICE
CERTIFICATE OF CORRECTION

PATENT NO. : 5,428,147

DATED : June 27, 1995

INVENTOR(S) : Richard F. Barker, et al

Page 1 of 2

It is certified that error appears in the above-indentified patent and that said Letters Patent is hereby corrected as shown below:

Column 4, line 28: Delete "soots," and insert --roots,--
Column 12, line 53: Delete "construction or" and insert --construction of--
Column 14, line 48: Delete "vital" and insert --viral--

Column 17, lines 42-43: Delete "may encode derived" and insert --may be derived--

Column 18, line 27: Delete "pTi15955" and insert --pTi15955.--
Column 20, line 35: Delete "CATATG" and insert --CAT<u>AT</u>G--
Column 20, line 37: Delete "ATCGAT(G)" and insert --ATC<u>GAT(G)</u>--
Column 20, line 38: Delete "CCATGG" and insert --CC<u>ATGG</u>--

Column 25, line 15: Delete "other deposited strains are listed in T.9.3."
Column 28, line 40: Delete "(Mural" and insert --(Murai--
Column 30, line 42: Delete "H. Caroff" and insert --H. Garoff--
Column 31, lines 13-15: Delete "5'CAATAGAAAATTCATAGGGTTTACC3', 5'CCTGTTTAGTATCATAGCGTTATAC3', and 5'CATGTCAATCA-TTTGTACCCCGGTTG3'" and insert --5'CAATAGAAAATTCATA<u>G</u>GG-TTTACC3', 5'CCTGTTTAGTATCATA<u>G</u>CGTTATAC3', and 5'CATGT-CAATCAT<u>TT</u>GTA-CCCCGGTTG3'--
Column 31, line 36: Delete "phospharase" and insert --phosphatase--
Column 31, line 43: Delete "vital" and insert --viral--
Column 34, line 29: Delete "vector ssDNA" and insert --vector, ssDNA--
Column 36, line 63: Delete "HindIII" and insert --HindIII--
Column 37, line 14: Delete "CGGTAAAAAGGAGCCCTGAAAGCG" and insert --CGGTAAAAAGGA<u>G</u>CCCTGAAAGCG--

UNITED STATES PATENT AND TRADEMARK OFFICE
CERTIFICATE OF CORRECTION

PATENT NO. : 5,428,147
DATED : June 27, 1995
INVENTOR(S) : Richard F. Barker, et al It is certified that error appears in the above-indentified patent and that said Letters Patent is hereby corrected as shown below:

Column 37, lines 32-36: Delete "CAAATTCCGGATCCCAGCGAAGTTG, CCTACTGACATATGTTACAAAAATGTTGTCTC, CAGGGTGGTGT-AGCATGCGCACCCCATATGTAATTAACTG, and CCATGTTTGCAC-GGATCCTGATTTCG" and insert --CAAATTCCGGATCCCAGCGAAG-TTG, CCTACTGA<u>C</u>ATATG<u>T</u>TACAAAAATGTTGTCTC, CAGGGTGGT-GTAGCATGCGCACCCCAT<u>AT</u>G<u>T</u>AATTAACTG, and CCATGTTTGCA-CGG<u>A</u>TCCTGATTTCG--.

Column 37, line 68: Delete "GGAGGTAACATATGGATAACAATCCG" and insert--GGAGGTAAC<u>A</u>TATGGATAACAATCCG--

Column 38, line 1: Delete "GCGGCAGATTAACGTGTTCATATGCATTCGAG" and insert --GCGGCAGAT<u>T</u>AACGTGTTCATA<u>T</u>GCATTCGAG--

Table 7, line 2: Delete "CTGTGAGCCAGCGGA<u>G</u>ATGCCATGTTC    7,282"
and insert --CTGTGAGCCAGCGCA<u>G</u>ATGCCATTC    7,282--

Signed and Sealed this

Twenty-fifth Day of June, 1996

Attest:

BRUCE LEHMAN

*Attesting Officer*   Commissioner of Patents and Trademarks